(12) United States Patent
Moehlenbruck et al.

(10) Patent No.: US 6,723,335 B1
(45) Date of Patent: Apr. 20, 2004

(54) METHODS AND COMPOSITIONS FOR TREATING INTERVERTEBRAL DISC DEGENERATION

(76) Inventors: Jeffrey William Moehlenbruck, 6910 Hart La., #705, Austin, TX (US) 78731; John Paul Ranieri, 1406 Molhe Dr., Austin, TX (US) 78703

( * ) Notice: Subject to any disclaimer, the term of this patent is extended or adjusted under 35 U.S.C. 154(b) by 0 days.

(21) Appl. No.: 09/545,441

(22) Filed: Apr. 7, 2000

(51) Int. Cl.[7] .............................. A61F 2/00; A61F 13/00
(52) U.S. Cl. ........................ 424/425; 424/422; 424/423; 424/424
(58) Field of Search ................................ 424/422, 423, 424/424, 425, 548

(56) References Cited

U.S. PATENT DOCUMENTS

| | | | |
|---|---|---|---|
| 4,413,359 A | 11/1983 | Akiama et al. ..................... 3/1 |
| 4,663,358 A | 5/1987 | Hyon et al. ..................... 521/64 |
| 4,772,287 A | 9/1988 | Ray et al. ..................... 623/17 |
| 4,801,299 A | 1/1989 | Brendel et al. ................. 623/1 |
| 4,834,757 A | 5/1989 | Brantigan ..................... 623/17 |
| 4,904,260 A | 2/1990 | Ray et al. ..................... 623/17 |
| 4,932,696 A | 6/1990 | White ..................... 292/336.3 |
| 5,015,255 A | 5/1991 | Kuslich ..................... 623/17 |
| 5,047,055 A | 9/1991 | Bao et al. ..................... 623/17 |
| 5,100,422 A | 3/1992 | Berguer et al. ............. 606/151 |
| 5,147,374 A | 9/1992 | Fernandez ................. 606/151 |
| 5,171,278 A | 12/1992 | Pisharodi ..................... 623/17 |
| 5,192,326 A | 3/1993 | Bao et al. ..................... 623/17 |
| 5,259,043 A | 11/1993 | Stone ..................... 623/66 |
| 5,304,194 A | 4/1994 | Chee et al. ................. 606/191 |
| 5,342,394 A | 8/1994 | Matsuno et al. ............ 606/213 |
| 5,370,660 A | 12/1994 | Weinstein et al. .......... 606/215 |
| 5,390,683 A | 2/1995 | Pisharodi ..................... 128/898 |
| 5,425,772 A | 6/1995 | Brantigan ..................... 623/17 |
| 5,437,288 A | 8/1995 | Schwartz et al. ........... 128/772 |
| 5,464,439 A | 11/1995 | Gendler ..................... 623/16 |
| 5,514,180 A | 5/1996 | Heggeness et al. ........... 623/17 |
| 5,540,715 A | 7/1996 | Katsaros et al. ............. 606/213 |
| 5,545,229 A | 8/1996 | Parsons et al. ................. 623/17 |
| 5,562,736 A | 10/1996 | Ray et al. ..................... 623/17 |
| 5,573,520 A | 11/1996 | Schwartz et al. ........... 604/282 |
| 5,645,597 A | 7/1997 | Krapiva ..................... 623/17 |
| 5,681,310 A | 10/1997 | Yuam et al. .................. 606/61 |
| 5,716,416 A | 2/1998 | Lin ............................. 623/17 |
| 5,741,429 A | 4/1998 | Donadio ........................ 615/8 |
| 5,776,142 A | 7/1998 | Gunderson .................. 606/108 |
| 5,800,549 A | 9/1998 | Bao et al. ..................... 623/17 |
| 5,800,550 A | 9/1998 | Sertich ......................... 623/17 |
| 5,815,904 A | 10/1998 | Clubb et al. .................. 29/418 |
| 5,824,093 A | 10/1998 | Ray et al. ..................... 623/17 |
| 5,827,325 A | 10/1998 | Buttermann ................. 623/17 |
| 5,879,366 A | 3/1999 | Shaw et al. ................. 606/213 |
| 5,911,752 A | 6/1999 | Dustrude et al. ............. 623/1 |
| 5,916,225 A | 6/1999 | Kugel ......................... 606/151 |
| 5,976,174 A | 11/1999 | Ruiz ........................... 606/213 |

(List continued on next page.)

OTHER PUBLICATIONS

Nishimura et al., Percutaneous reinsertion of the nucleus pulposus: An experimental study, SPINE 23:1531–1538, 1998.*

Primary Examiner—James M. Spear
Assistant Examiner—Rachel M. Bennett
(74) Attorney, Agent, or Firm—Williams, Morgan & Amerson, P.C.; Timothy L. Scott

(57) ABSTRACT

A fluid matrix comprising cross-linked remodelable collagen from a donor vertebrate animal is useful for regenerating hydrodynamic function in damaged intervertebral discs in vivo. The matrix may be injectable and may comprise cells and a plurality of purified cell growth factors. The matrix promotes cell growth and elaboration of proteoglycans to facilitate regeneration of native tissues. The collagen in the matrix may be cross-linked using photooxidative catalysis and visible light, and purified cell growth factors are preferably at least partly bone-derived.

11 Claims, 52 Drawing Sheets

A B

•Lane A: Non cross-linked control shows substantial protein extraction
•Lane B: Cross-linked matrix demonstrates reduced protein extraction

U.S. PATENT DOCUMENTS

| | | | |
|---|---|---|---|
| 5,976,186 A | 11/1999 | Bao et al. | 623/17 |
| 6,022,343 A | 2/2000 | Johnson et al. | 604/526 |
| 6,024,754 A | 2/2000 | Engelson | 606/213 |
| 6,027,863 A | 2/2000 | Donadio, III | 430/320 |
| 6,033,394 A | 3/2000 | Vidlund et al. | 604/524 |
| 6,051,648 A * | 4/2000 | Rhee et al. | 525/54.1 |
| 6,080,579 A * | 6/2000 | Hanley, Jr. et al. | 435/366 |
| 6,107,004 A | 8/2000 | Donadio, III | 430/320 |
| 6,110,164 A | 8/2000 | Vidlund | 604/542 |
| 6,132,460 A | 10/2000 | Thompson | 623/1.15 |
| 6,132,461 A | 10/2000 | Thompson | 623/1.15 |
| 6,203,732 B1 | 3/2001 | Clubb et al. | 264/81 |
| 6,245,107 B1 | 6/2001 | Ferree | 623/17 |
| 6,273,876 B1 | 8/2001 | Klima et al. | 604/264 |
| 6,290,692 B1 | 9/2001 | Klima et al. | 604/524 |
| 6,340,369 B1 * | 1/2002 | Ferree | 623/17.11 |
| 6,344,058 B1 * | 2/2002 | Ferree | 623/17.11 |
| 6,352,557 B1 * | 3/2002 | Ferree | 623/17.11 |
| 6,419,702 B1 * | 7/2002 | Ferree | 623/17.11 |

* cited by examiner

Figure 1 – Healthy Nucleus Pulposus Tissue

Figure 1A – Magnified Proteoglycan Aggregate

Figure 2: Cross-linked Matrix

- Lane A: Non cross-linked control shows substantial protein extraction
- Lane B: Cross-linked matrix demonstrates reduced protein extraction

Figure 4: Comparison of Fresh Porcine Nucleus Pulposus versus Cross-linked Matrix
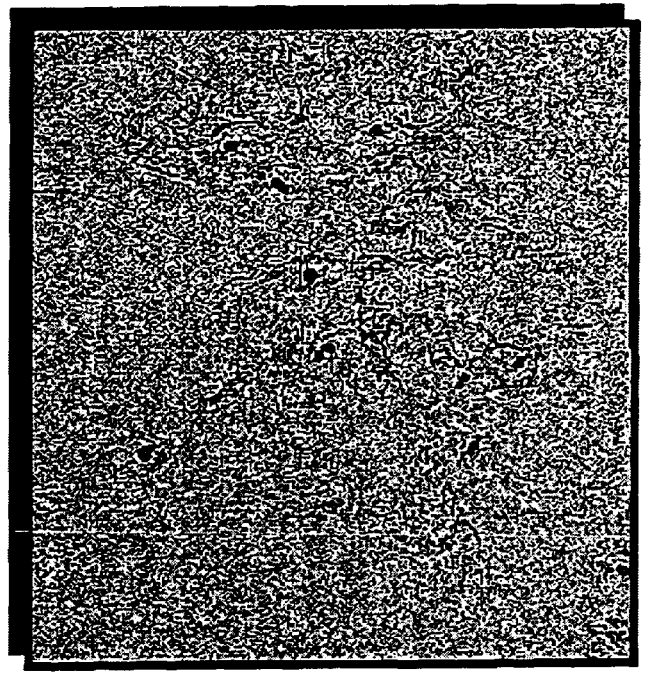
4B: Cross-linked Matrix
- disrupted, crenated cell fragments
- minimal cell membrane material
- further isopropanol sterilization
4A: Fresh Nucleus Pulposus
- round, nucleated chondrocytes
- intact pericellular matrix "nests"

A B

- Lane A: Pepsin digests of non cross-linked control react with Type II collagen antibodies
- Lane B: Pepsin digests of cross-linked matrix does not react with Type II collagen antibodies

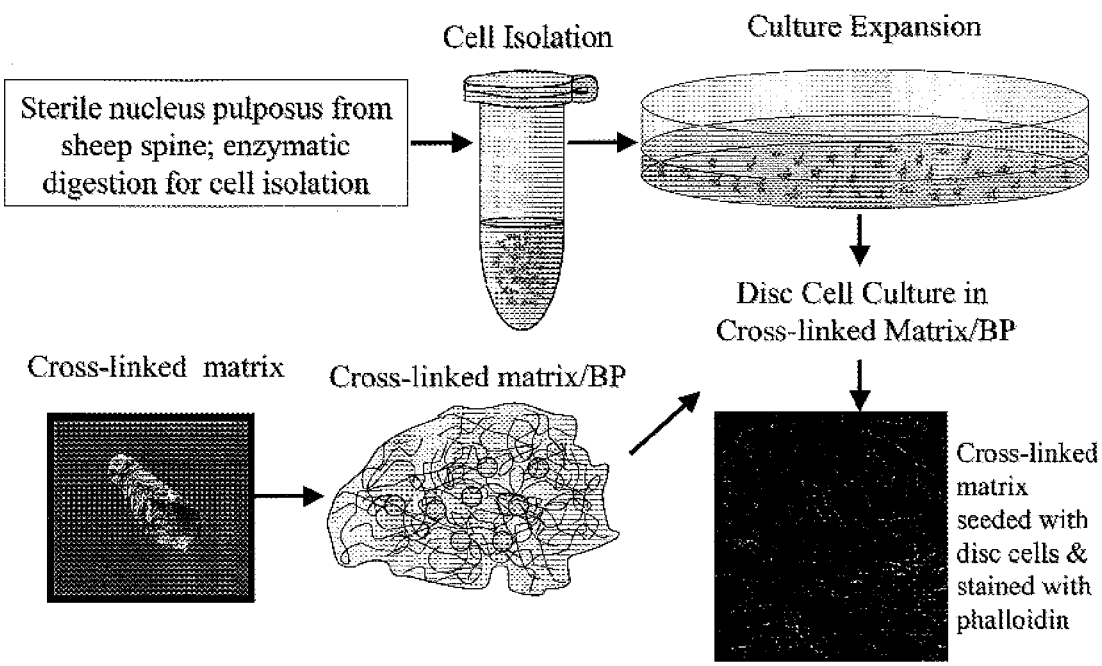
*Figure 7: Growth and Proliferation of Disc cells into Cross-linked Matrix*

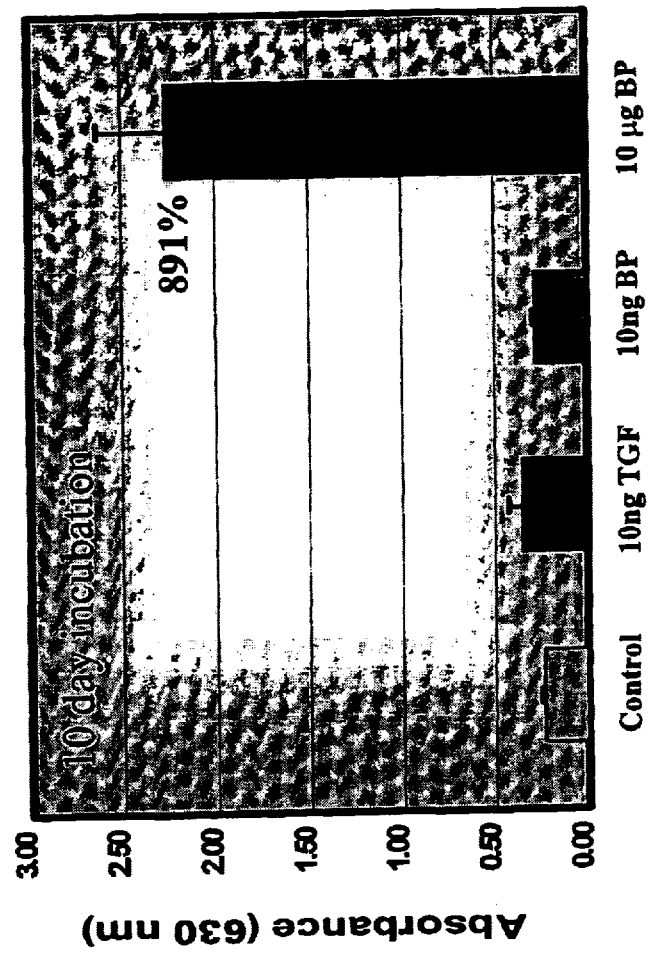
*Figure 8: Growth Factor Stimulation of Matrix Synthesis*
- Significant stimulation of matrix production only at μg BP concentrations

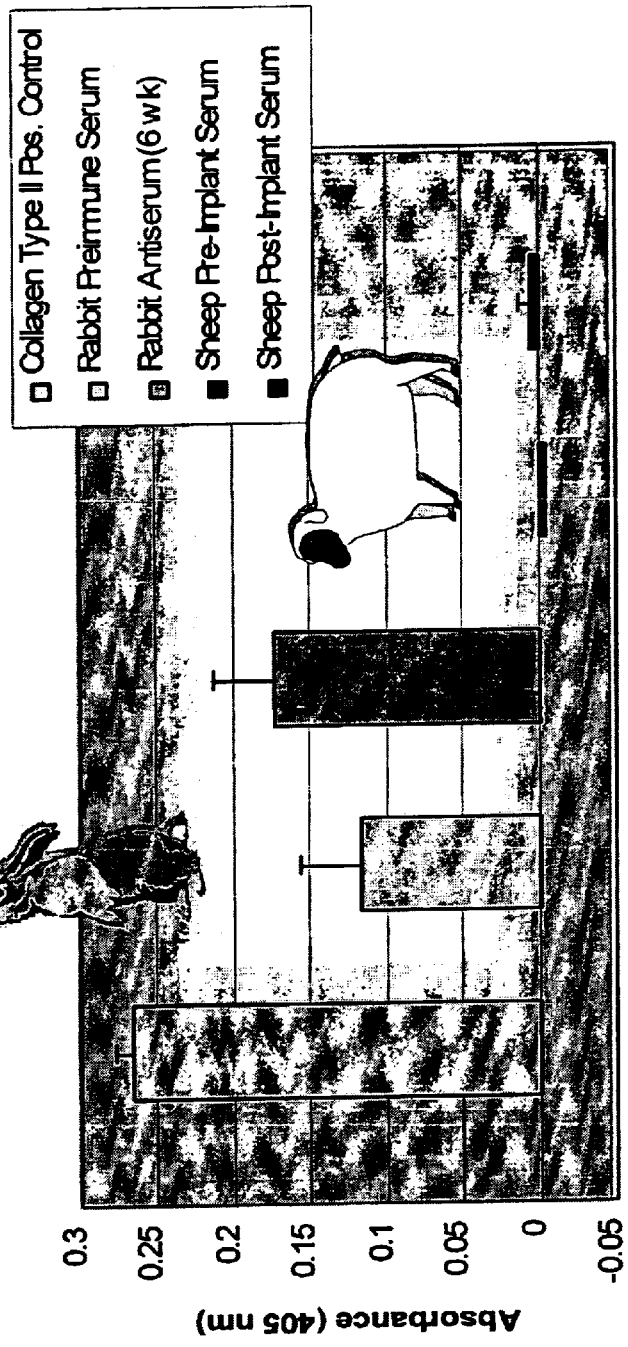
Figure 9: Cross-linked Matrix Immunogenicity
- Low antibody titers to cross-linked matrix in rabbit immunizations
- No serum antibodies to cross-linked matrix *in vivo* (1st sheep)

Figure 10: Pilot Study #1
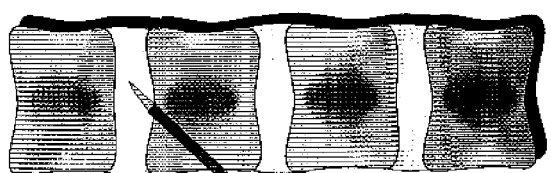
1st operation: annulus stabs to create two degenerative discs
Wait 2 months
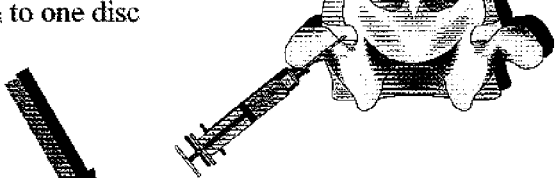
2nd operation: Cross-linked matrix/BP gel treatment injection to one disc
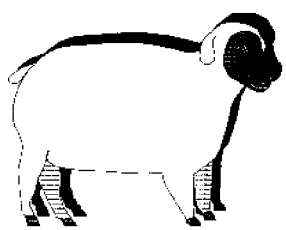
- Histomorphometry
- MRI/radiographs
- Immune response
Sacrifice: 2, 4, and 6 months

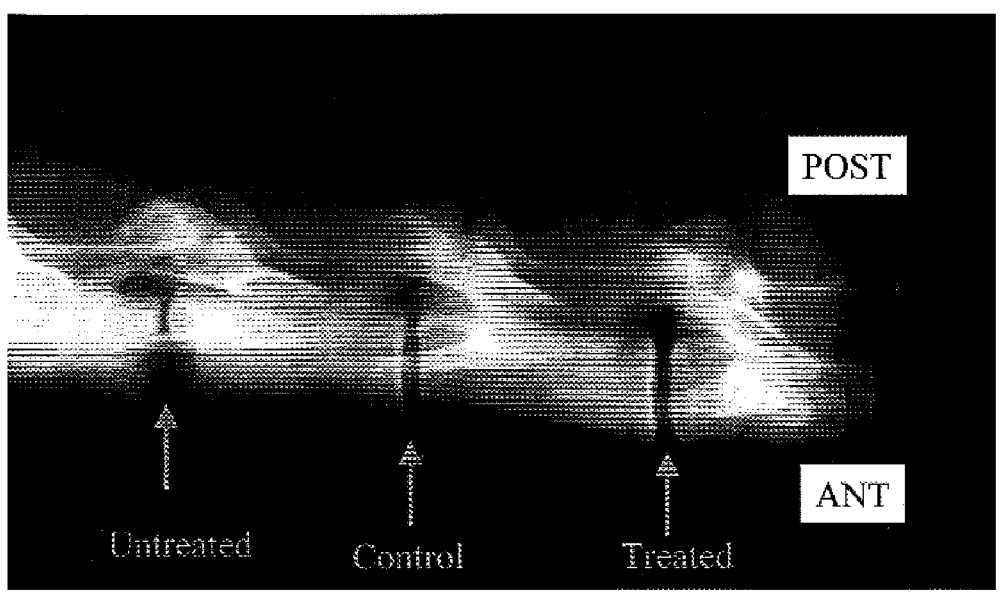
*Figure 11: Radiograph-Pilot Study #1*
*2 Months Post Injection (Cross-linked matrix/BP)*
- Treated and Control discs: normal size and appearance of disc structures
- Untreated disc: disjunct endplates, bone resorption and remodeling

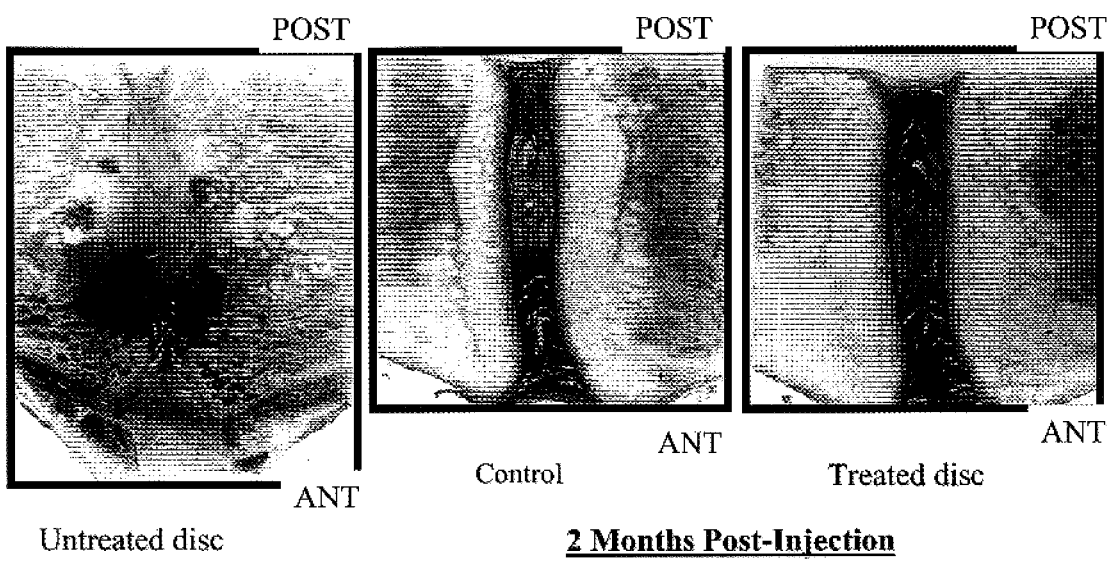
Figure 12: Histology- Pilot Study #1
Untreated disc | Control | Treated disc
2 Months Post-Injection
- Untreated disc exhibits extensive degeneration
- Cross-linked matrix/BP-treated disc retains normal structures similar to Control disc

*Figure 13: Radiograph- Pilot Study #1*
*4 Months Post Injection (Cross-linked matrix/BP)*
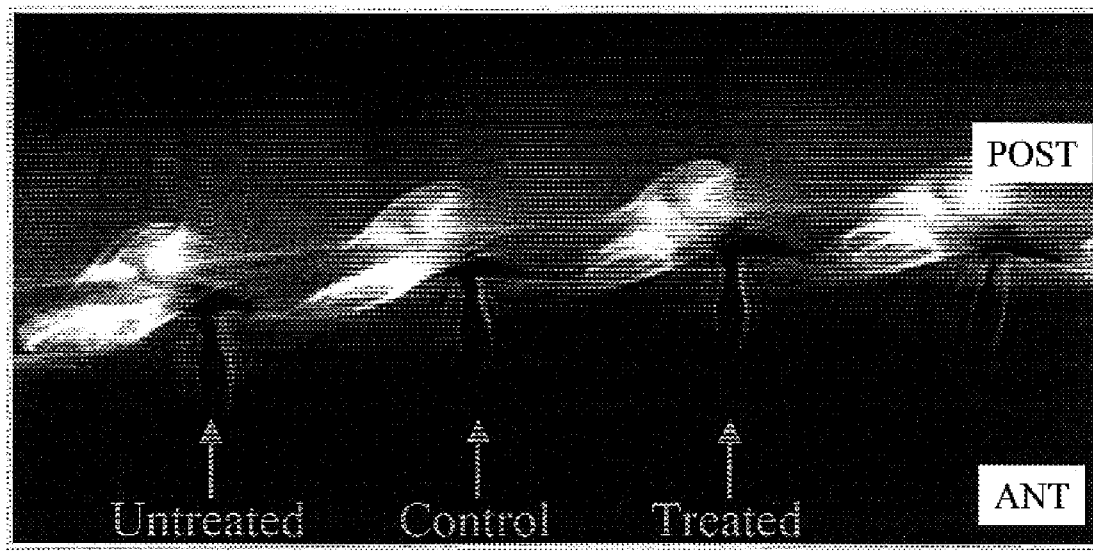
No apparent radiographic differences between discs in 4 month sheep.

*Figure 14:Histology- Pilot Study #1*
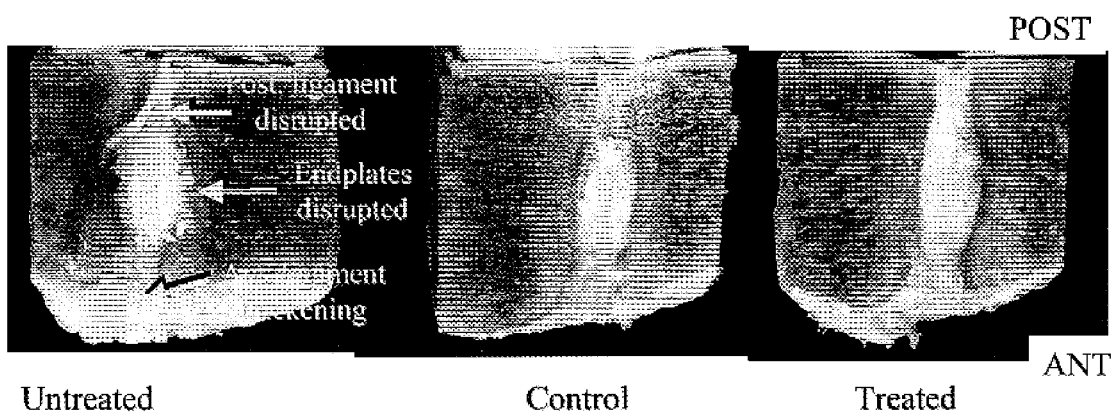
Untreated     Control     Treated
<u>4 Months Post-Injection</u>
• Untreated disc exhibits degenerative changes
• Cross-linked matrix/BP-treated disc similar to control disc: normal gelatinous nucleus, regular annulus, intact endplates Figure 15: Growth Factor Stimulation of Type II Collagen & Chondroitin-6-Sulfate Synthesis

Figure 16: Growth Factor Stimulation of Proteoglycan Synthesis in Human Intervertebral Disc Nucleus Pulposus Cells

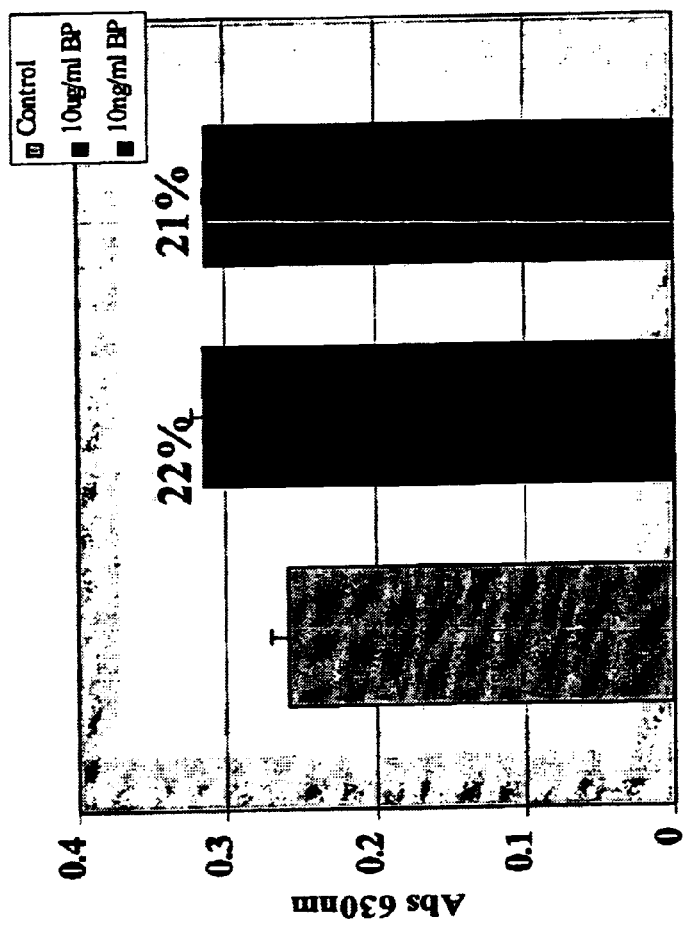
Figure 17: Growth Factor Stimulation of Proteoglycan Synthesis in Baboon Intervertebral Disc Nucleus Pulposus Cells

| Band No. | Identity |
|---|---|
| 1 | Histone H1.c |
| 2 | Histone H1.c |
| 3 | Ribosomal protein RS20 |
| 4 | Similar to ribosomal protein LORP |
| 5 | BMP-3 |
| 6 | α2 macroglobulin RAP and BMP-3 |
| 7 | Similar to ribosomal protein LORP |
| 8 | BMP-3 |
| 9 | BMP-3 |
| 11 | Ribosomal protein RL6 and BMP-3 |
| 18 | TGF-β2 / SPP 24 |
| 20 | Factor H |
| 22 | TGF-β2 |
| 25 | BMP-3 and H1.x |
| 29 | BMP-3 and ribosomal protein RL32 |

| No. | Identity | No. | Identity |
|---|---|---|---|
| 1 | Factor XIII | 11 | TGF-β2/SPP24 |
| 2 | LORP | 12 | SPP24 |
| 3 | LORP | 12 | TGF-β2/SPP24 |
| 4 | | 14 | lysyl oxidase |
| 5 | RL3 | 15 | lysyl oxidase |
| 6 | | 16 | lysyl oxidase |
| 7 | | 17 | lysyl oxidase |
| 8 | | 18 | BMP-3 |
| 9 | | 19 | cathepsin L |
| 10 | | 20 | |
| | | 21 | RS3a |

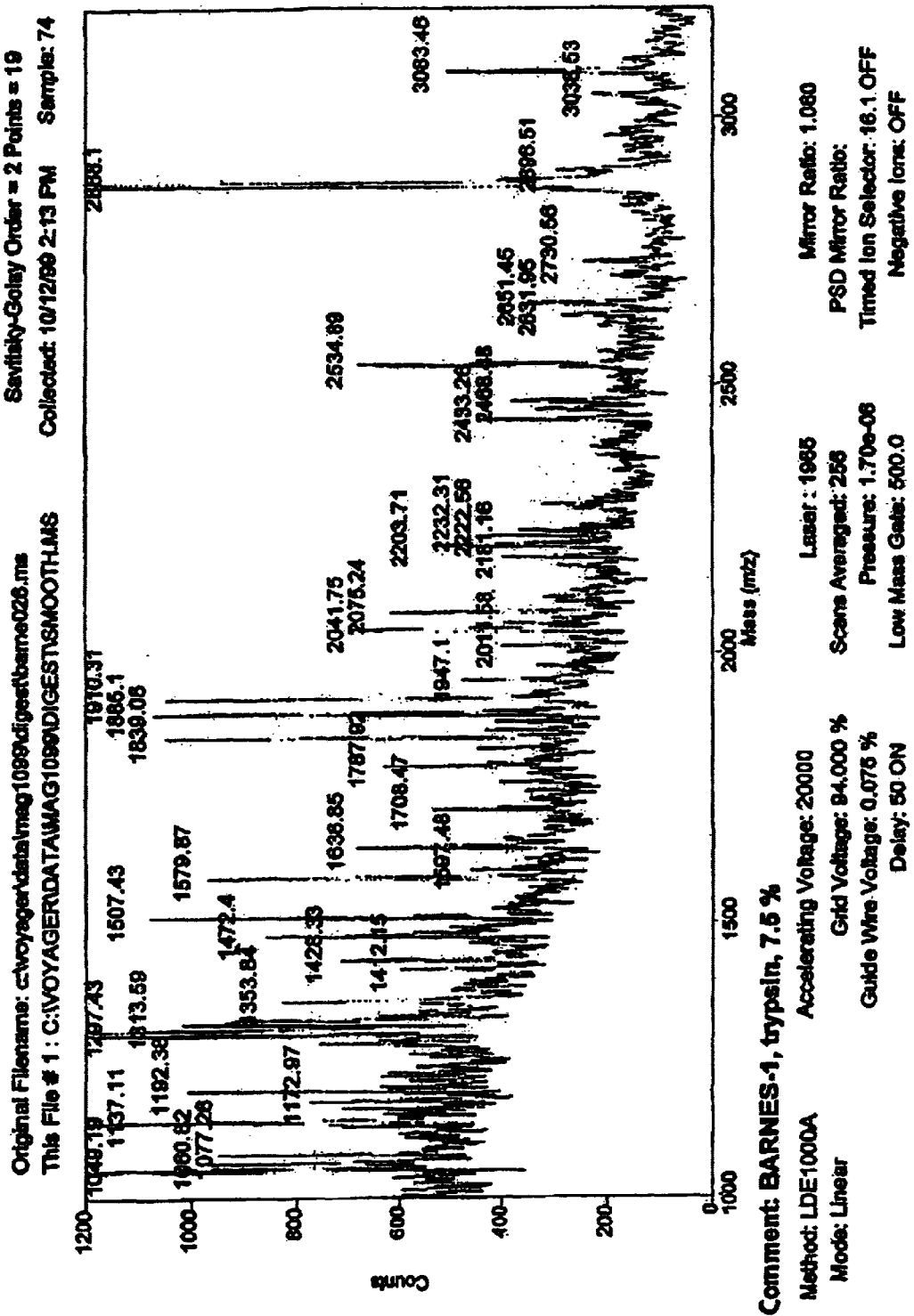
Figure 23A (Band 1)

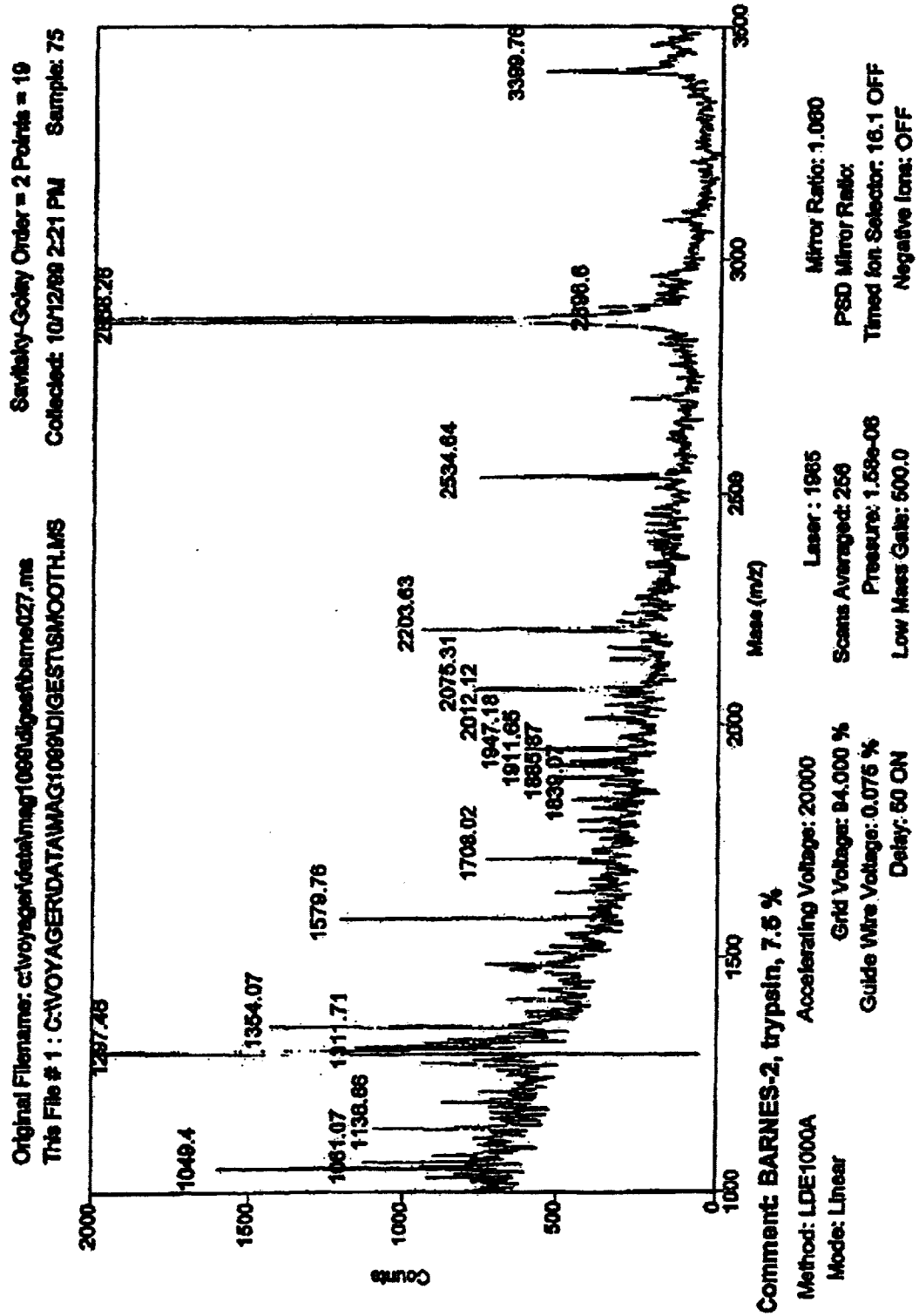
Figure 23B (Band 2)

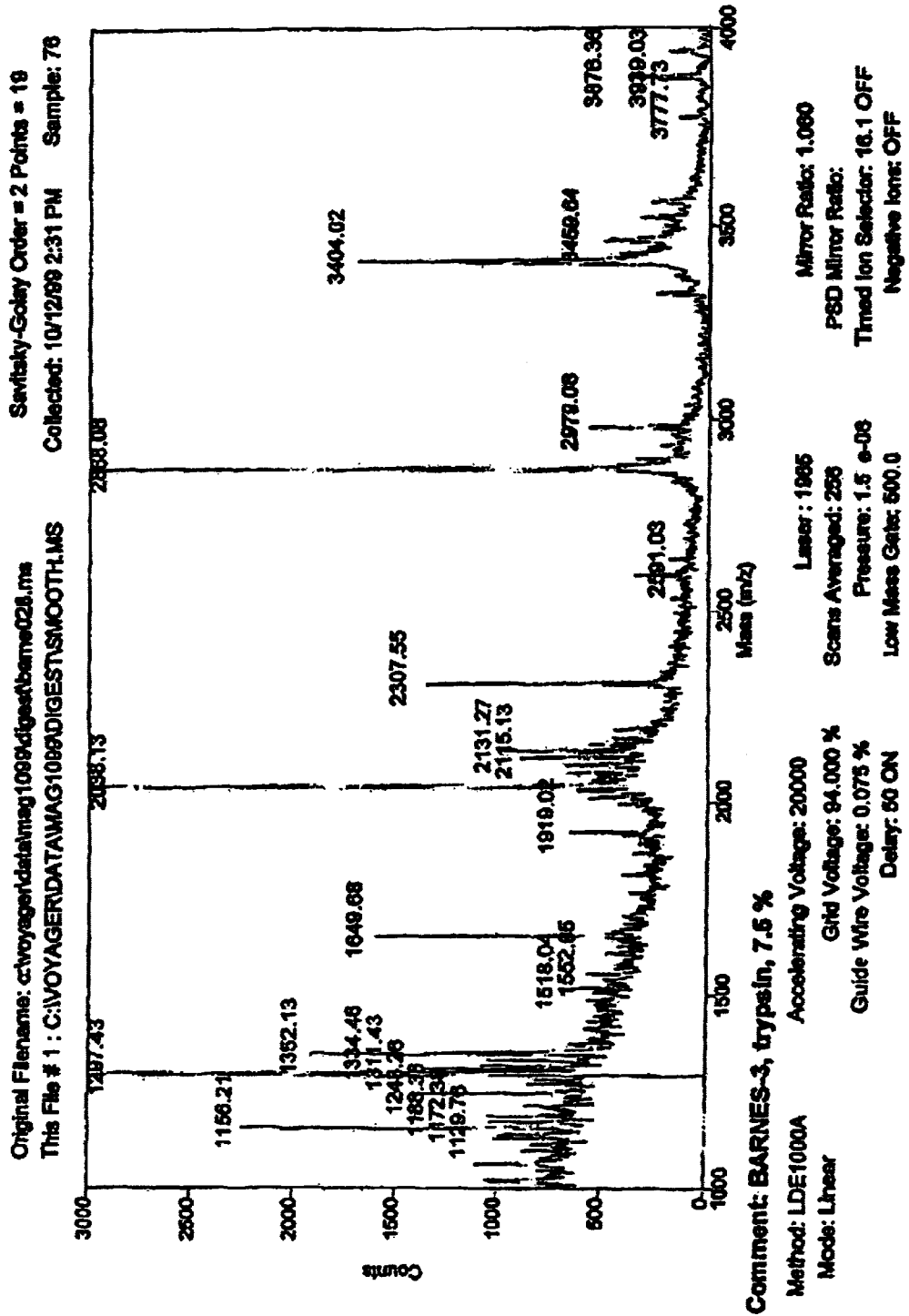
Figure 23C (Band 3)

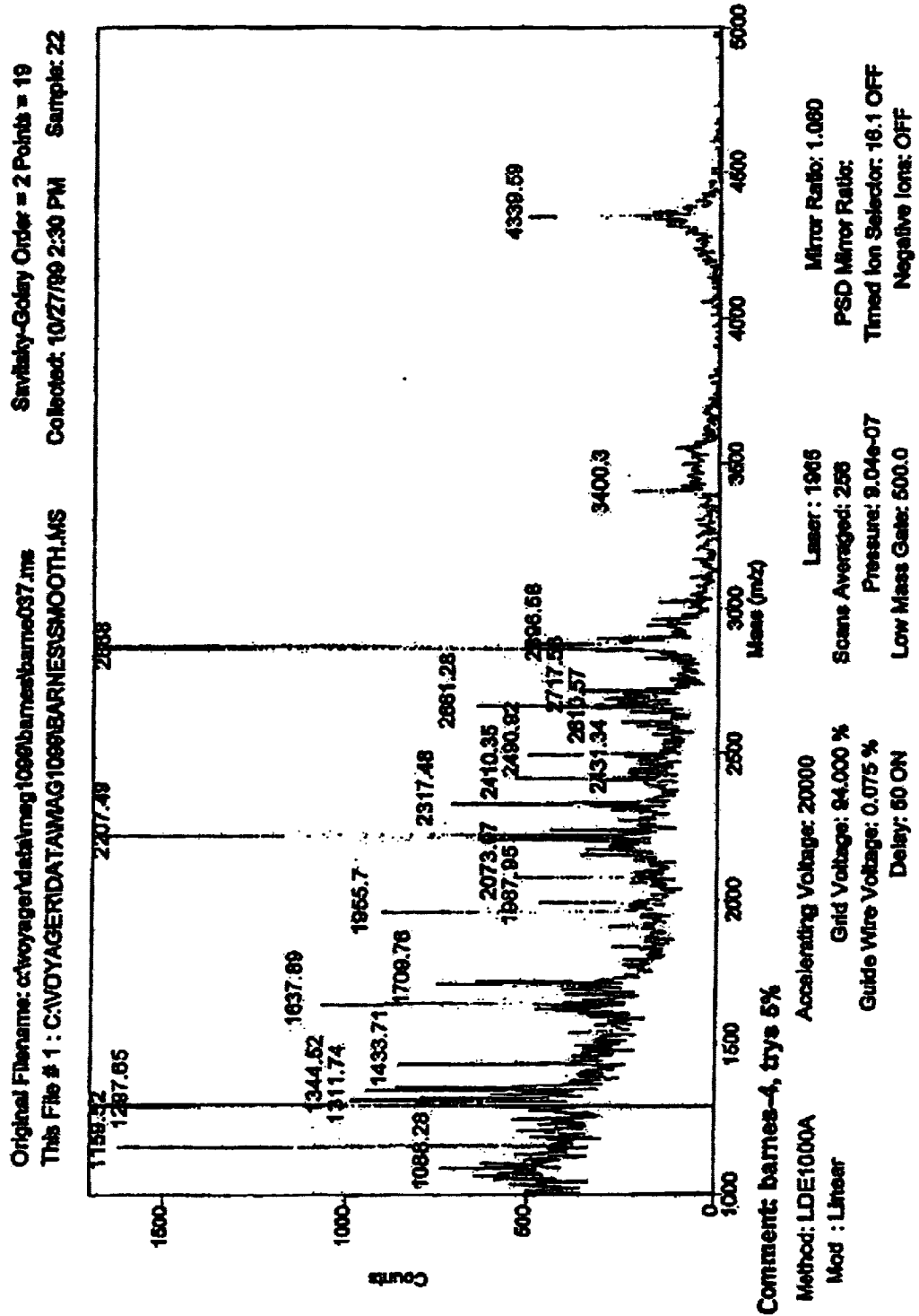
Figure 23D (Band 4)

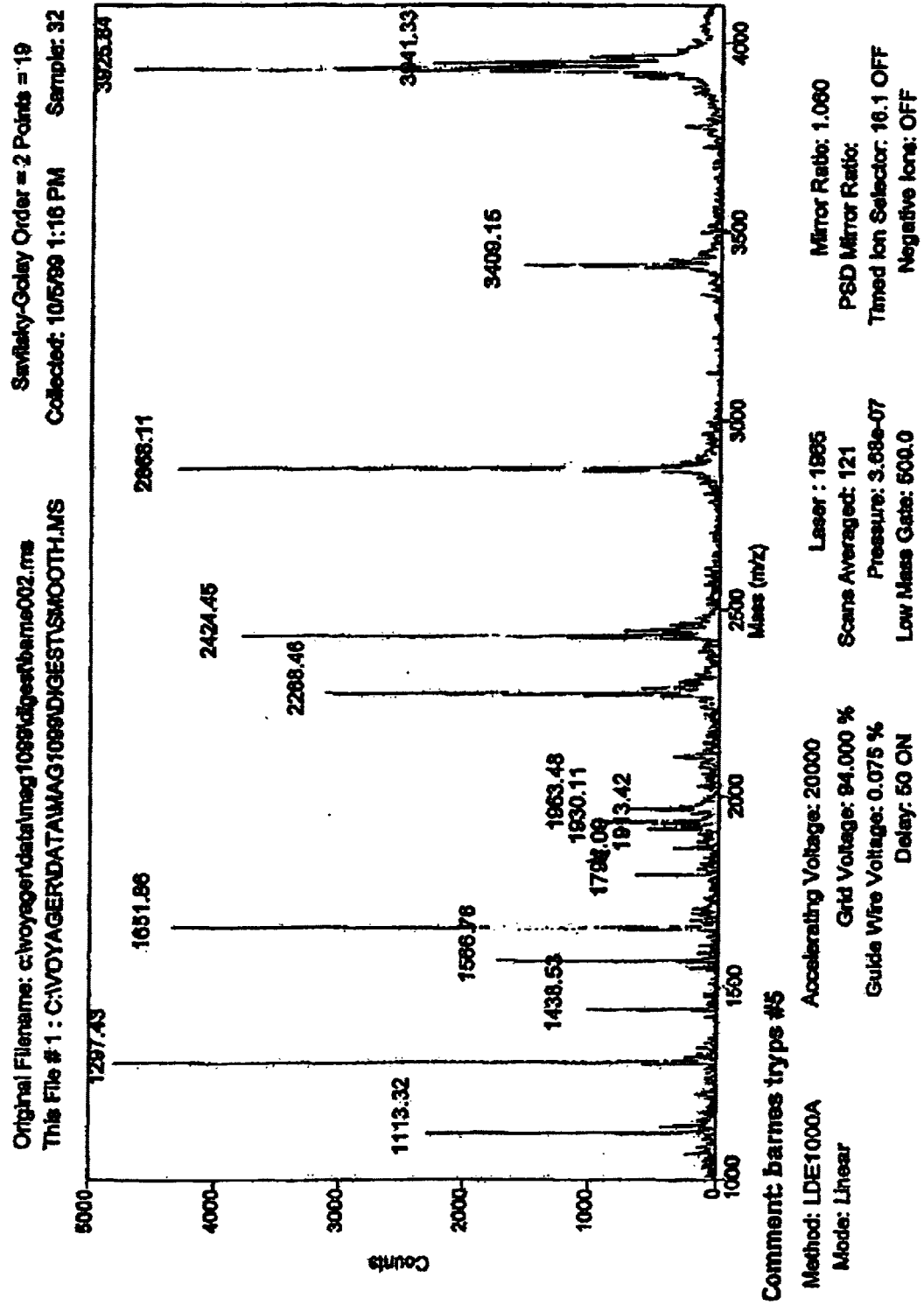
Figure 23E (Band 5)

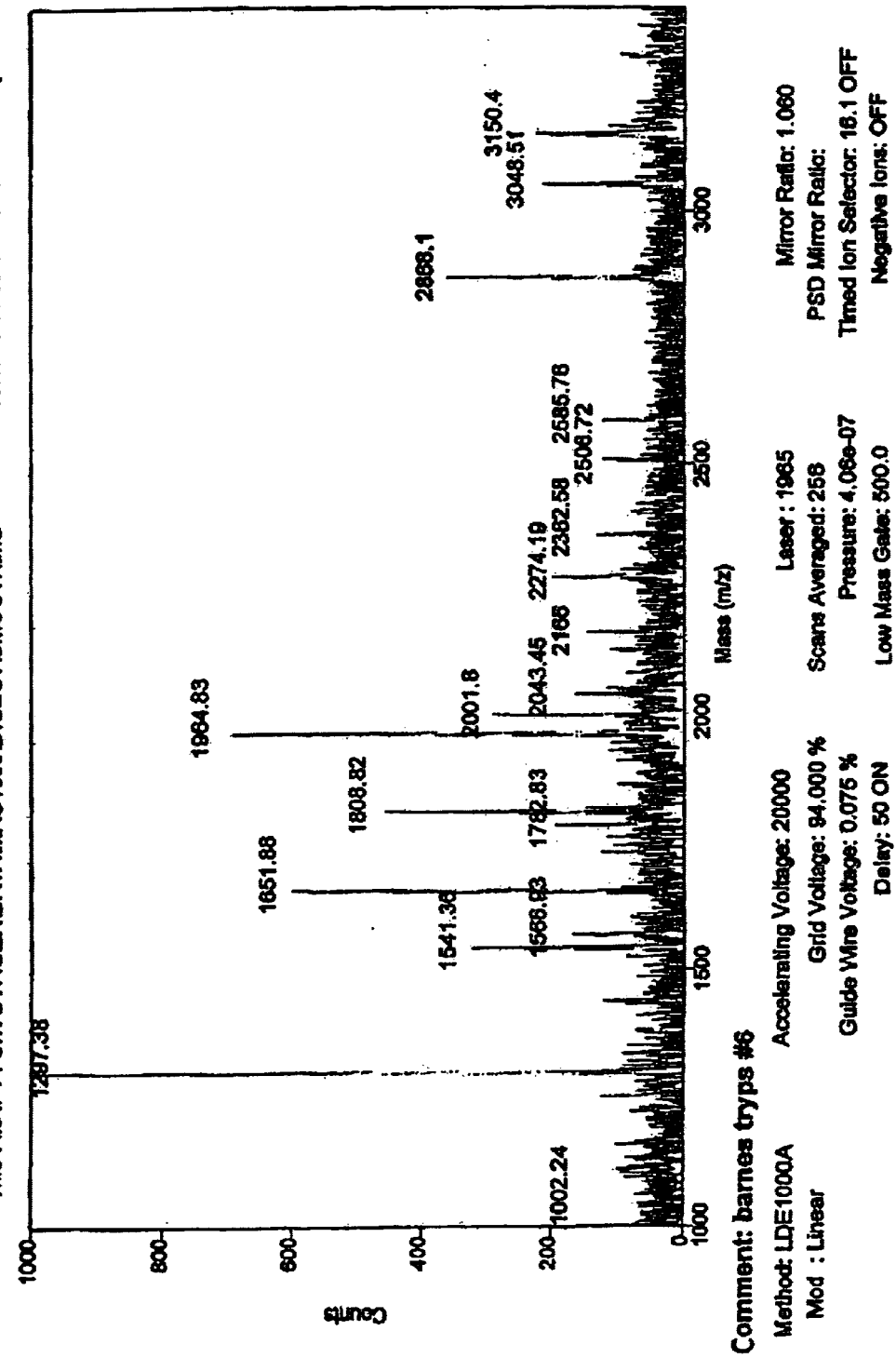
Figure 23F (Band 6)

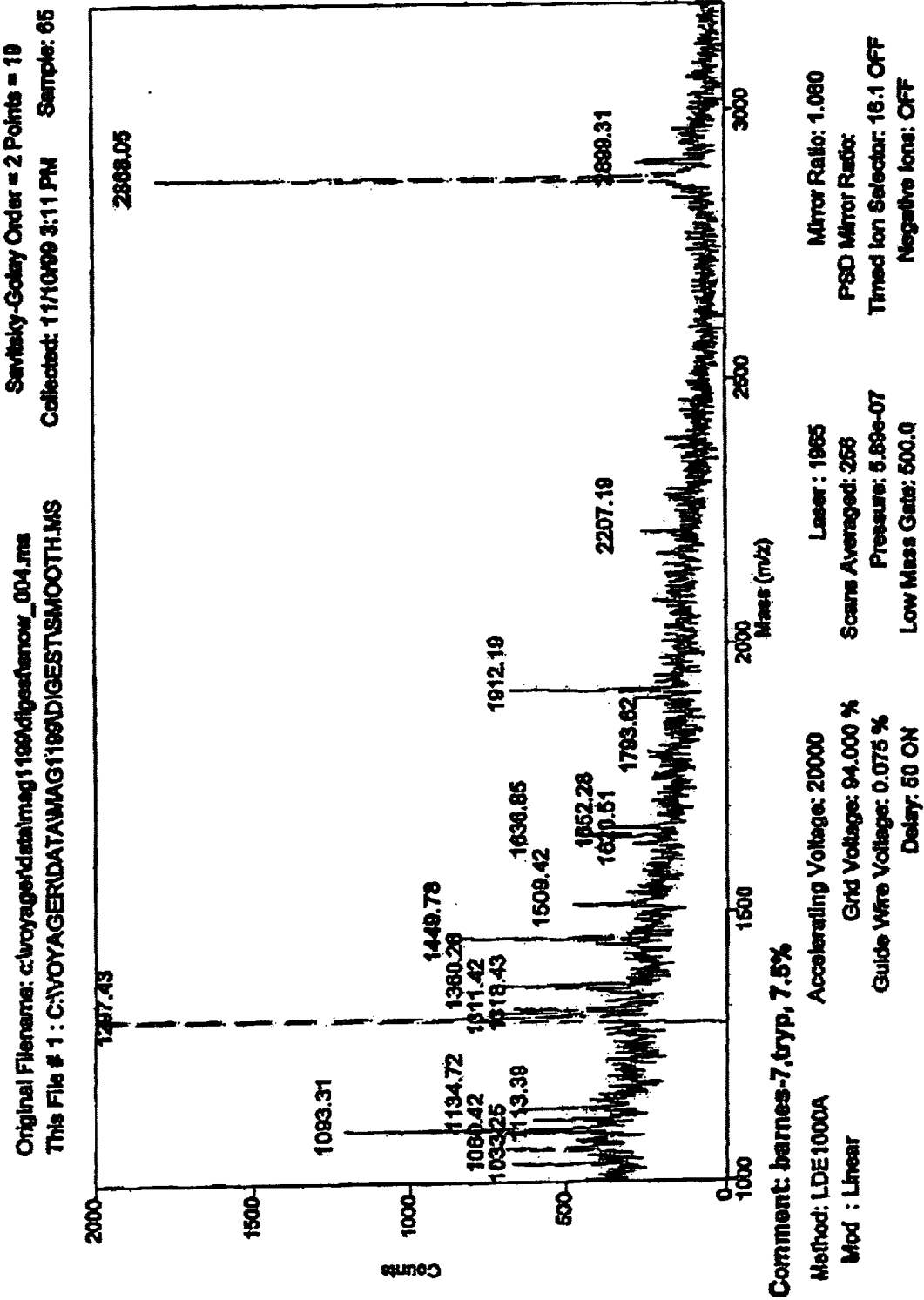
Figure 23G (Band 7)

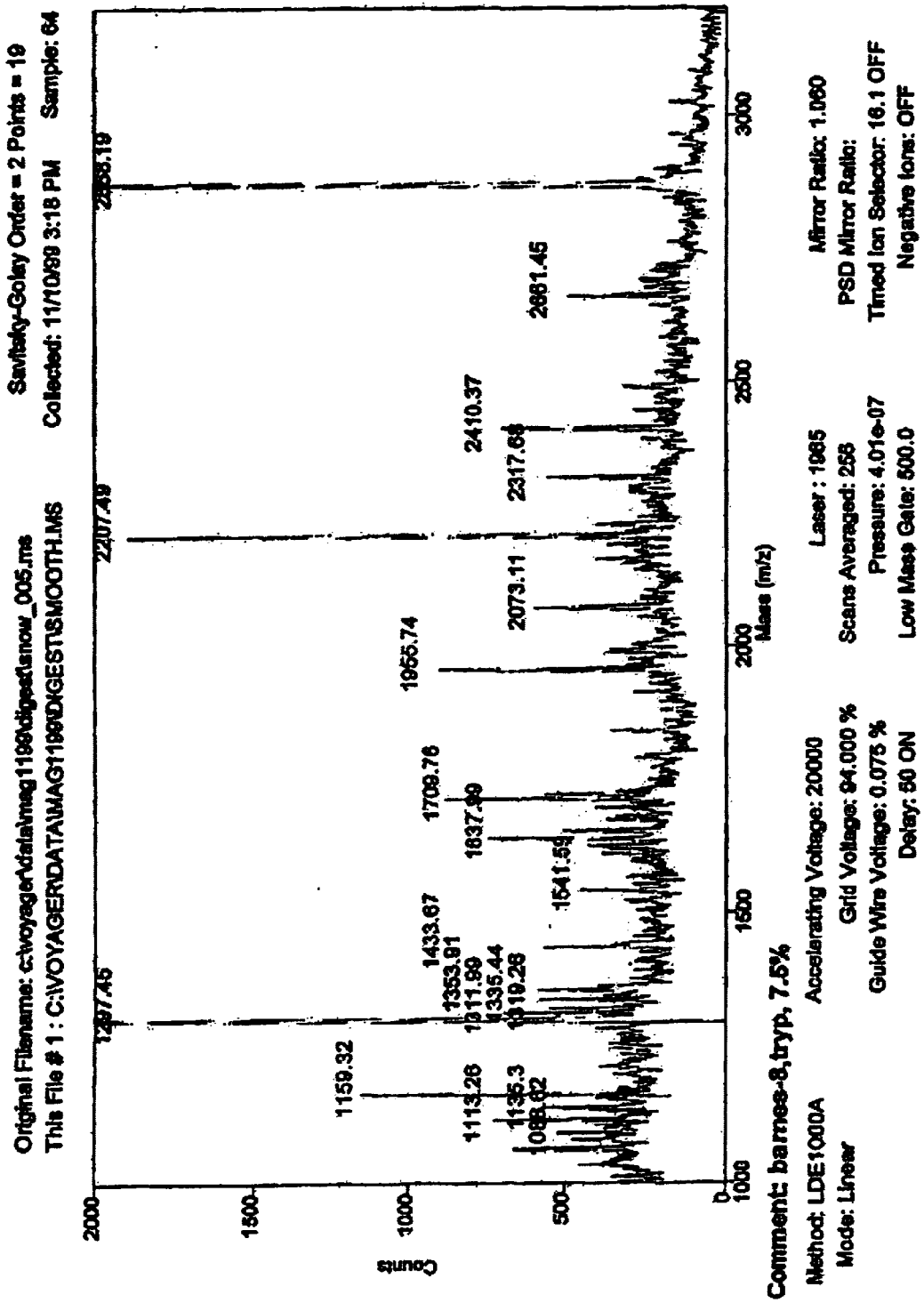
Figure 23H (Band 8)

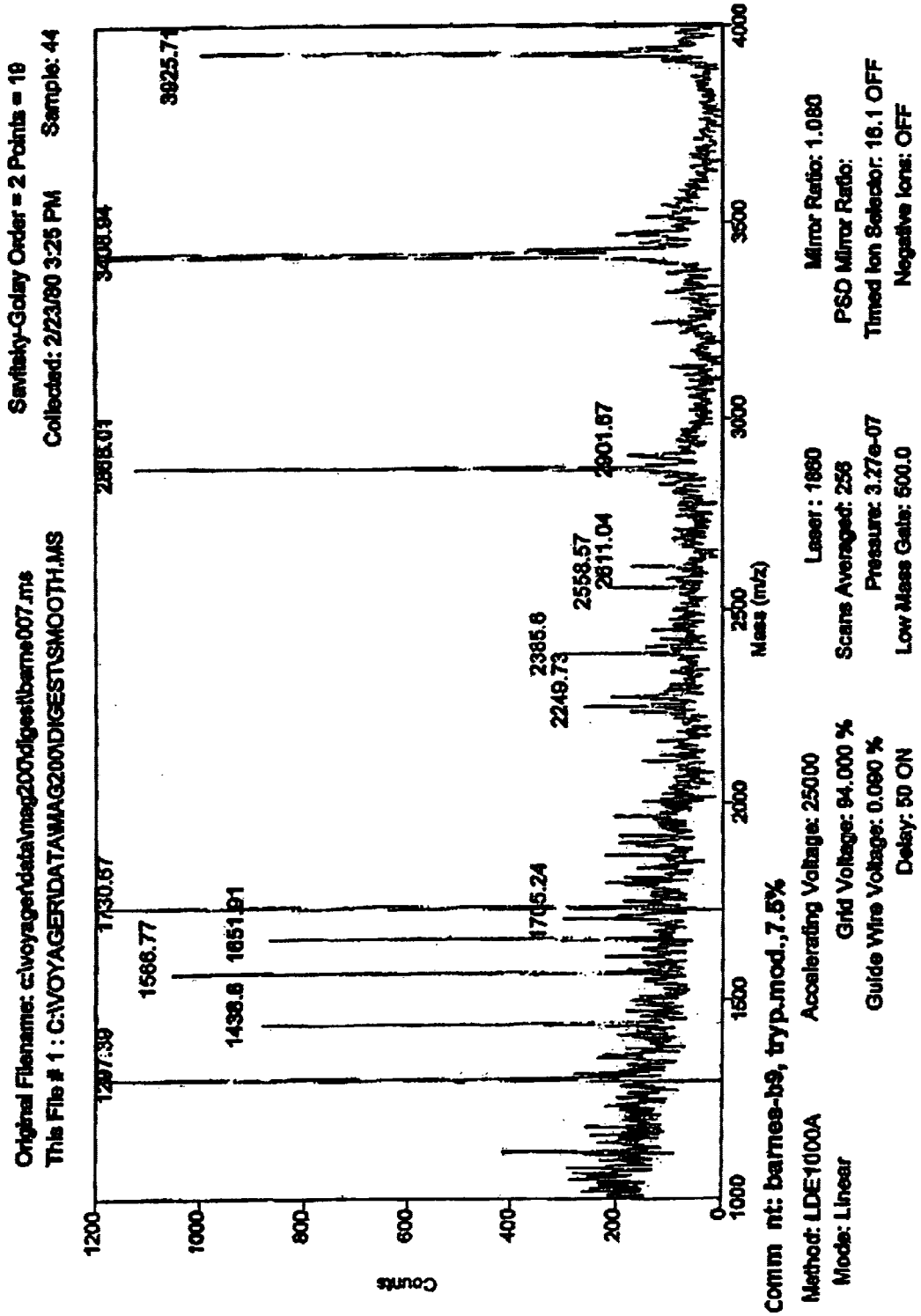
Figure 23I (Band 9)

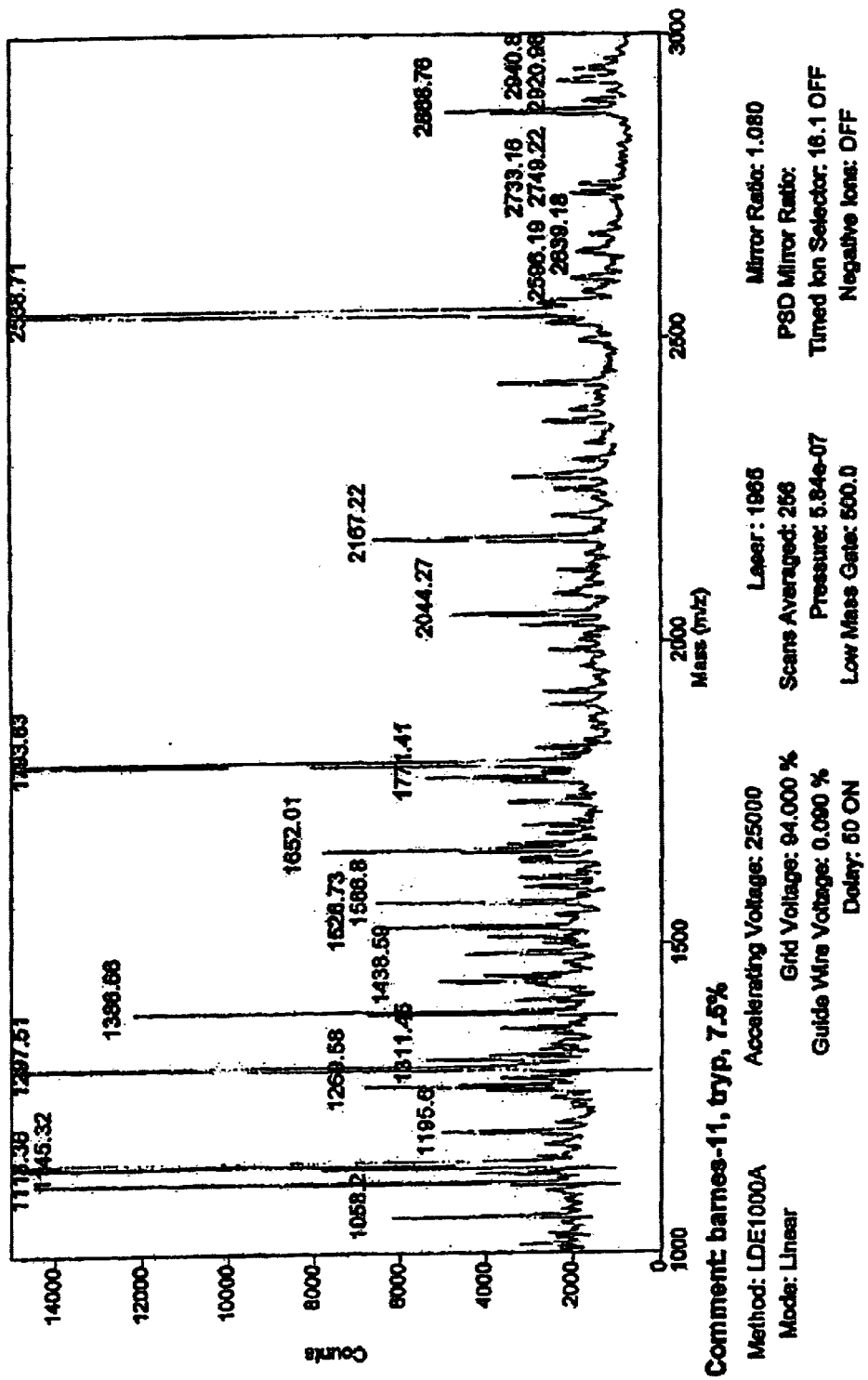
Figure 23J (Band 11)

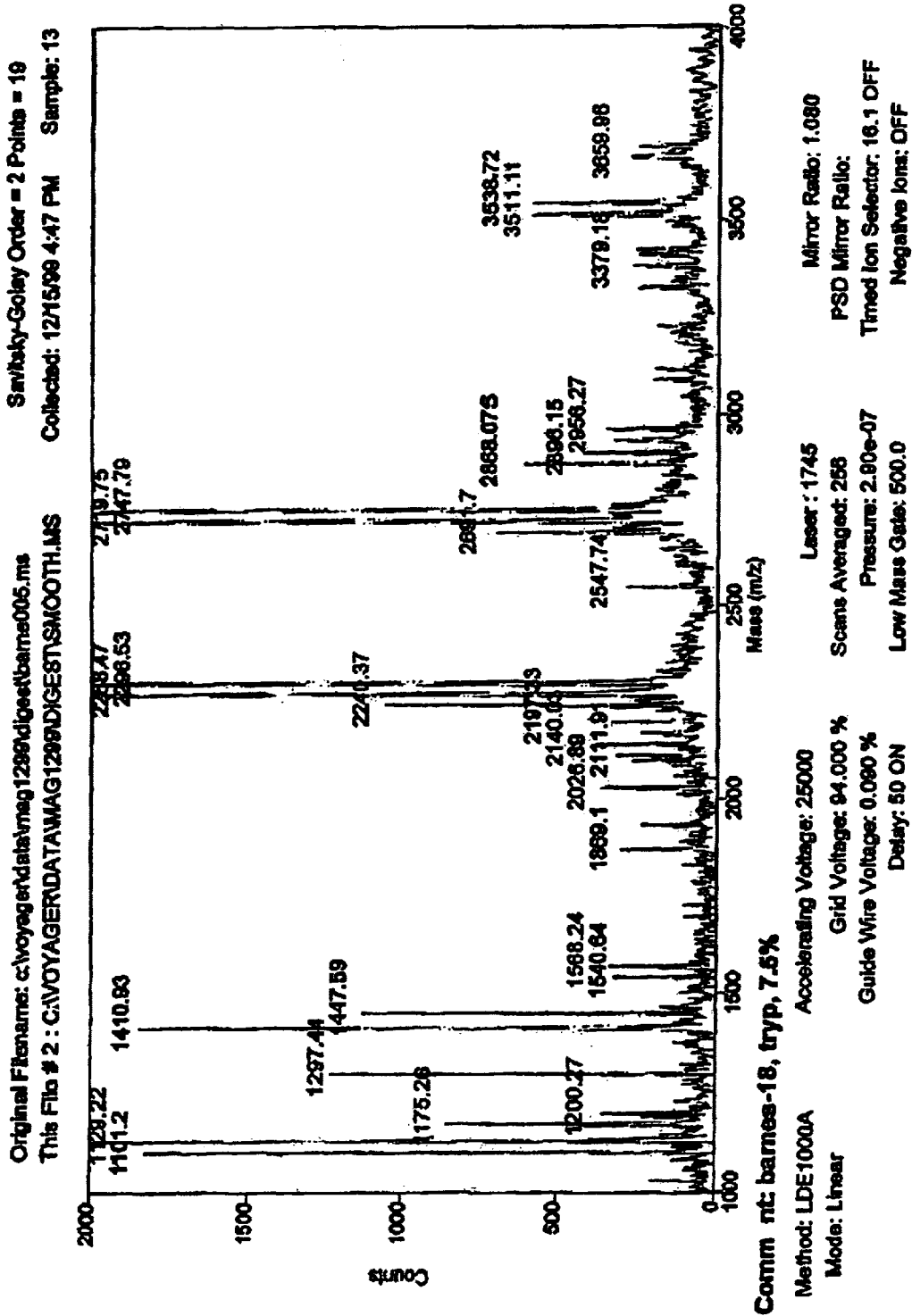
Figure 23K (Band 18)

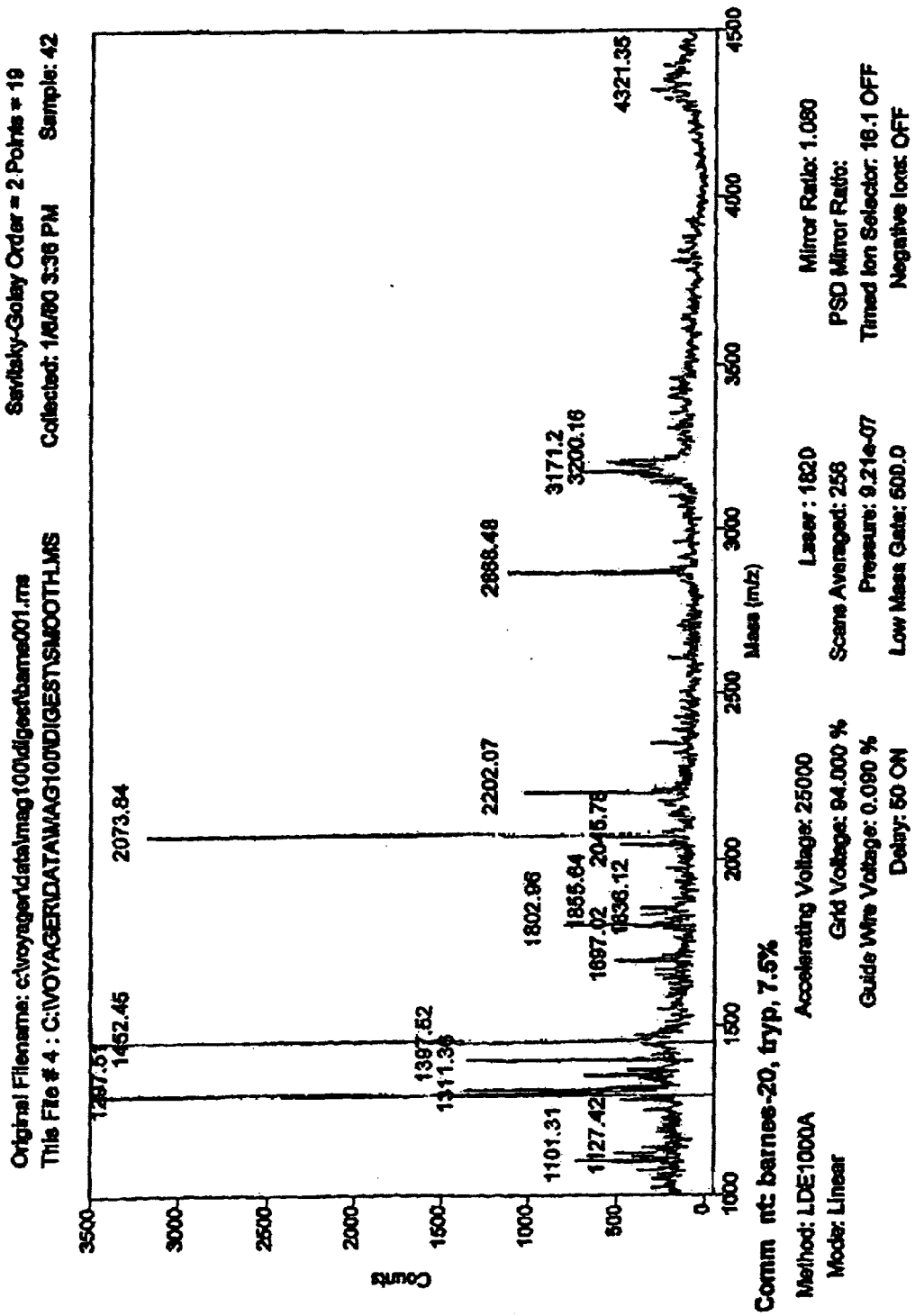
Figure 23L (Band 20)

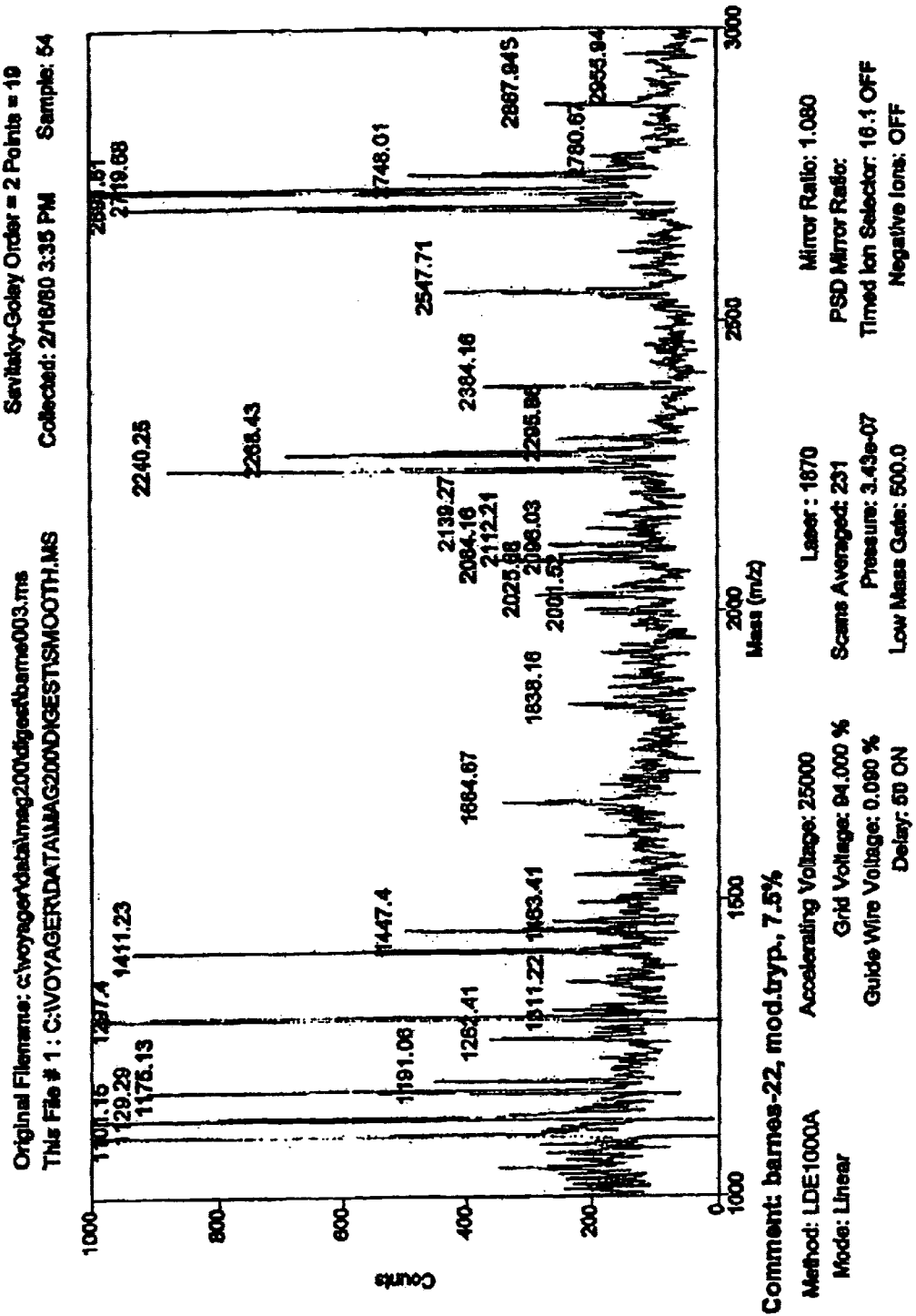
Figure 23M (Band 22)

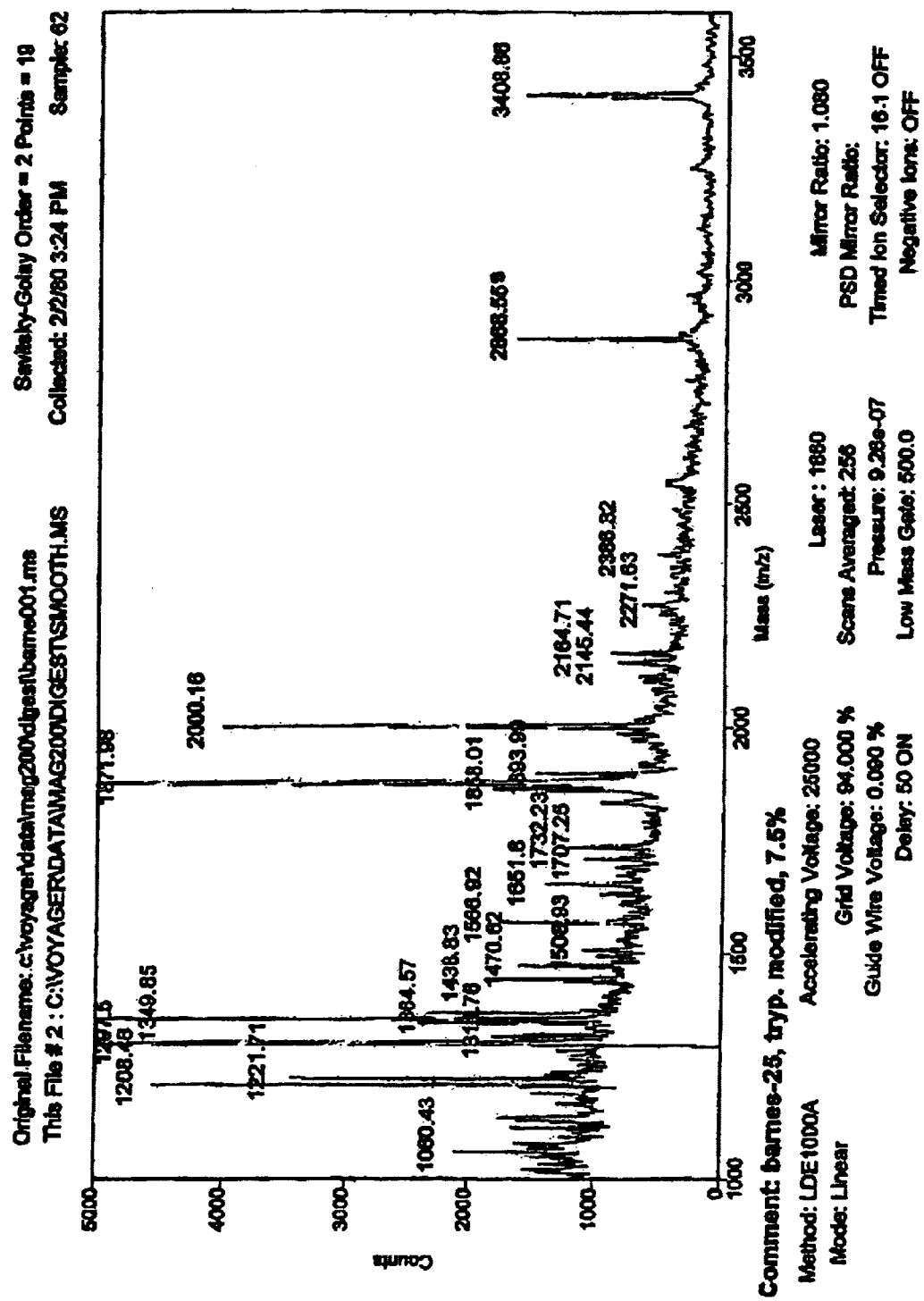
Figure 23N (Band 25)

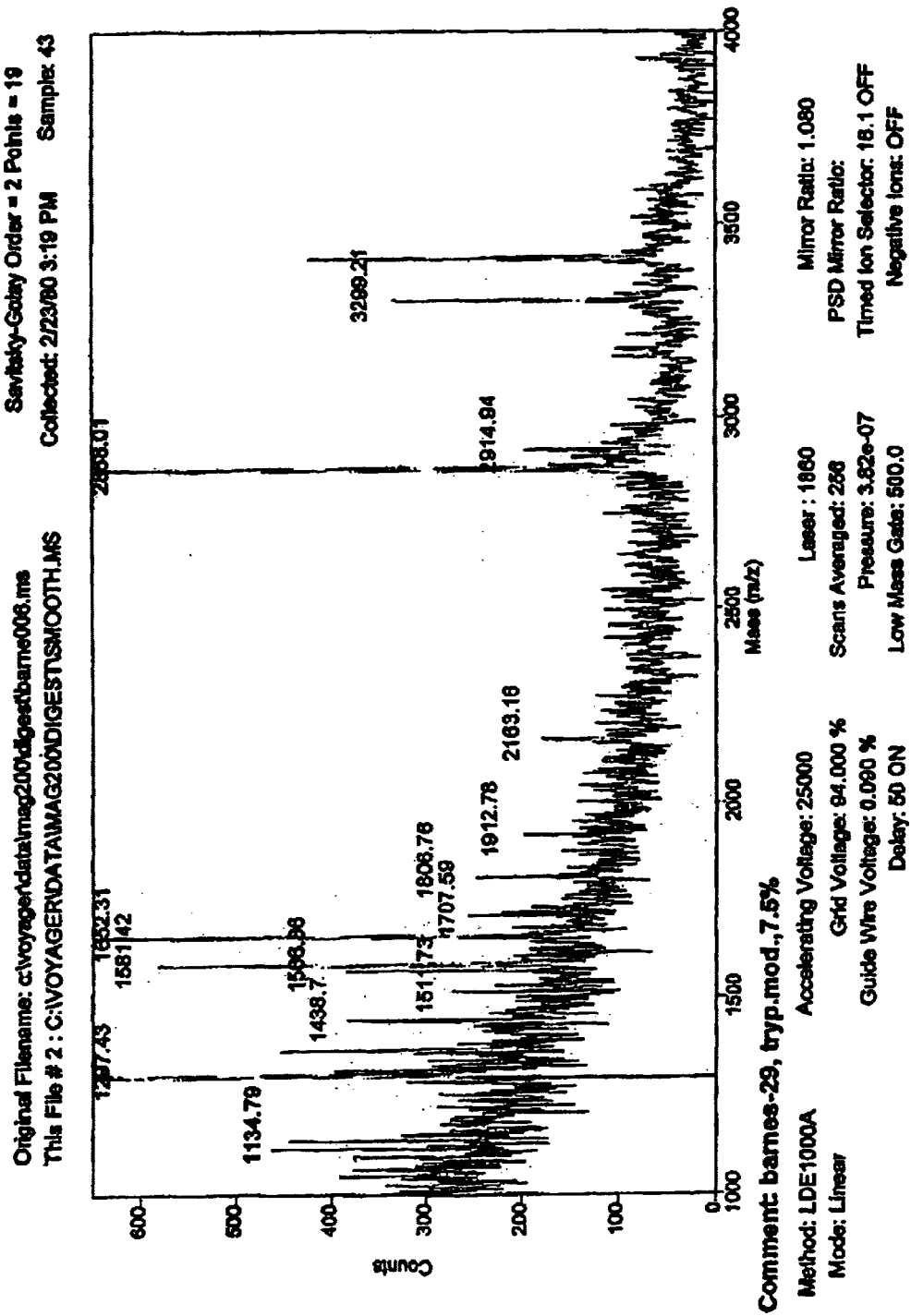
Figure 230 (Band 29)

FIGURE 26
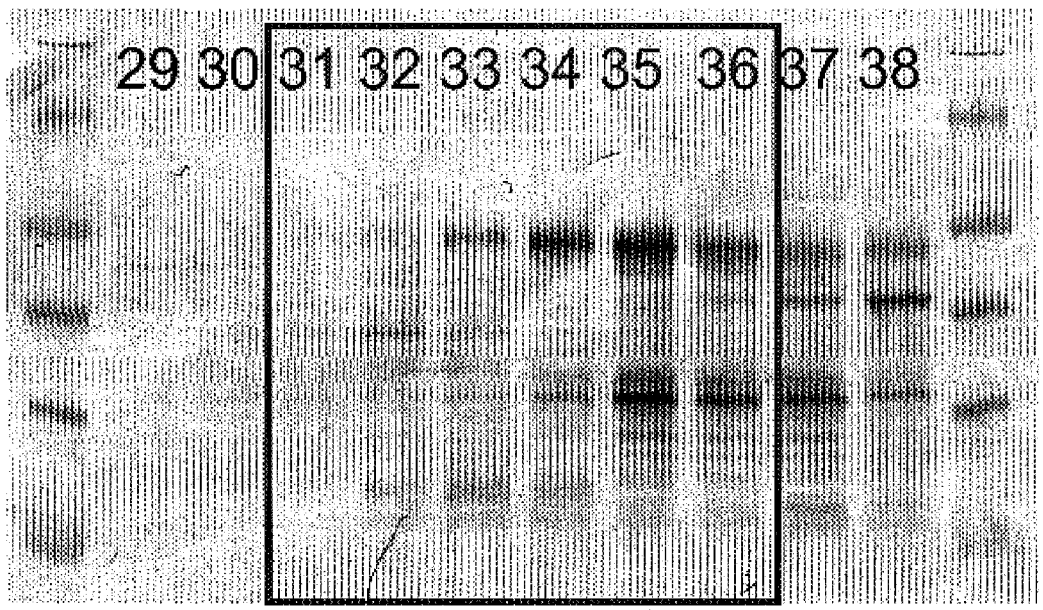
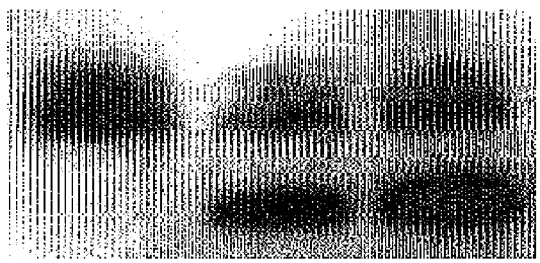
FIGURE 27
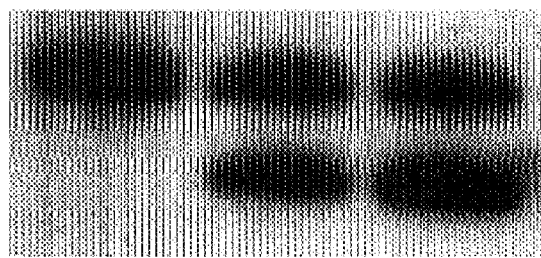
FIGURE 28

FIGURE 30: Antibody Listing

| Specificity | Antigen | Host Species | PC/MC | Source | Catalog No. |
|---|---|---|---|---|---|
| | | | | | |
| TGF-$\beta$1 (human) | Protein | Rabbit | Polyclonal | Promega | G1221 |
| TGF-$\beta$2 (human) | Peptide | Rabbit | Polyclonal | Santa Cruz Biotechnology | sc-90 |
| TGF-$\beta$3 (human) | Peptide | Rabbit | Polyclonal | Santa Cruz Biotechnology | sc-82 |
| | | | | | |
| BMP-2 (human) | Protein | Rabbit | Polyclonal | Austral Biologics | PA-513-9 |
| BMP-3 (human) | Peptide | Chicken | Polyclonal | Research Genetics | NA |
| BMP-4 (human) | Peptide | Goat | Polyclonal | Santa Cruz Biotechnology | sc-6896 |
| BMP-5 (human) | Peptide | Goat | Polyclonal | Santa Cruz Biotechnology | sc-7405 |
| BMP-6 (human) | Peptide | Mouse | Monoclonal | Novocastra Laboratories | NCL-BMP6 |
| BMP-7 (human) | Peptide | Rabbit | Polyclonal | Research Genetics | NA |
| FGF-1 (human) | Peptide | Goat | Polyclonal | Santa Cruz Biotechnology | sc-1884 |
| osteonectin (bovine) | Protein | Mouse | Monoclonal | DSHB | AON-1 |
| osteocalcin (bovine) | Protein | Rabbit | Polyclonal | Accurate Chemicals | A761/R1H |
| serum albumin (bovine) | Protein | Rabbit | Polyclonal | Chemicon International | AB870 |
| transferrin (human) | Protein | Chicken | Polyclonal | Chemicon International | AB797 |
| apo-A1 lipoprotein (human) | Protein | Goat | Polyclonal | Chemicon International | AB740 |

Figure 31A. Identification of Proteins by Amino Acid Sequencing of Tryptic Fragments

| Band | Sample | Sequence Data | Best Database Match | Match | Identification | Species | Acc. No. | AAs |
|---|---|---|---|---|---|---|---|---|
| 1 | | | | | | | | |
| 2 | fx 49 (1579) | XLAAAGYDVEK | ALAAAGYDVEK | 11/11 | histone H1.c | human | 87668 (NCBI) | 65-75 |
| 3 | fx 67 (1346) | SLEKVCADLIR | SLEKVCADLIR | 11/11 | 40s Ribosomal Protein S20 | rat | R3RT20 (PIR) | 31-41 |
| 4 | fx 65 0 | (V)VCGMLGFPSEAPV | VVCGMLGFPGEKRV | 11/14 | LORP | mouse | AAC95338 (NCBI) | 213-226 |
| 5 | N terminal seq | STGVLLPLQNNELPG | STGVLLPLQNNELPG | 15/15 | BMP-3 | human | 4557371 (NCBI) | 290-304 |
|  | fx 72 (3925) | STGVLLPLQNNELPGA EYQY | STGVLLPLQNNELPGA AEYQY | 20/20 | BMP-3 | human | 4557371 (NCBI) | 290-309 |
|  | fx 74 (3409) | STGVLLPLQ | STGVLLPLQ | 9/9 | BMP-3 | human | 4557371 (NCBI) | 290-298 |
| 6 | fx 55 (1566) | (S)QTLQFXE | SQTLQFDE | 7/8 | BMP-3 | human | 4557371 (NCBI) | 346-353 |
|  | fx 47 | VYAF | no match | | ??? | | | |
|  | N terminal seq | HAGKYSREKNT(P)A(P) | HGGKYSREKNQPKP | 11/14 | α2-Macroglobulin Receptor Assoc. Pro. | human | P30533 (Swiss-Prot) | 31-46 |
|  | fx 57 (1438) | SQTLQFDEQ | SQTLQFDEQ | 9/9 | BMP-3 | human | 4557371 (NCBI) | 346-354 |
|  | fx 57 (1652) | SLKPSNHA | SLKPSNHA | 8/8 | BMP-3 | human | 4557371 (NCBI) | 410-417 |
| 7 | fx 51 (1093) | AALRPLVKP | AALRPLVKP | 9/9 | 60s Ribosomal Protein L32 | mouse | P17932 (Swiss-Prot) | 1-9 |
|  | fx 37 (no MS) | A(H)I(Q)VERYV | AIVER | 5/5 | 60s Ribosomal Protein L32 | mouse | P17932 (Swiss-Prot) | 109-113 |
|  | fx 37 (no MS) | A(H)I(Q)VERYV | HQSDRYV | 5/7 | 60s Ribosomal Protein L32 | mouse | P17932 (Swiss-Prot) | 22-28 |
| 8 | fx 78 0 | XALF(G)AQLGXALGPI | no match | | ??? | | | |
| 9 | fx 56 (1567) | SQTLQFDEQT | SQTLQFDEQT | 10/10 | BMP-3 | human | P12645 (Swiss-Prot) | 346-355 |

Figure 31B. Identification of Proteins by Amino Acid Sequencing of Tryptic Fragments

| Band | Sample | Sequence Data | Best Database Match | Match | Identification | Species | Acc. No. | AAs |
|---|---|---|---|---|---|---|---|---|
| 11 | fx 55 (1311) | SQTLXF | SQTLQF | 5/6 | BMP-3 | human | 4557371 (NCBI) | 346-351 |
|  | fx 47 (1772) | VLATVTKPVGGDK | VLATVTKPVGGDK | 13/13 | 60s Ribosomal Protein L6 | human | Q02878 (Swiss-Prot) | 87-99 |
|  | fx 76 (1795) | xVFAL | VFAL | 4/4 | 60s Ribosomal Protein L6 | human | Q02878 (Swiss-Prot) | 273-276 |
|  | fx 61 (1145) | AVPQLQGYLR | AIPQLQGYLR | 9/10 | 60s Ribosomal Protein L6 | human | Q02878 (Swiss-Prot) | 262-271 |
| 18 |  |  |  |  |  |  |  |  |
| 22 | fx 58 (1101) | ALDAAYCFR | ALDAAYCFR | 9/9 | TGF-β2 | human | P08112 (Swiss-Prot) | 303-311 |
|  | fx 69 (no match) | GYNANFCAGACPYL | GYNANFCAGACPYL | 14/14 | TGF-β2 | human | P08112 (Swiss-Prot) | 340-353 |
|  | fx 66 (1411.71) | VNSQSLSPY | VNSQSLSPY | 9/9 | SPP24 | bovine | Q27967 (Swiss-Prot) | 42-50 |
| 25 | fx 39 (1470) | KAAKPSV(P) | KAAKPSVP | 8/8 | Histone H1.x | human | JC4928 (PIR) | 199-206 |
| 29 |  |  |  |  |  |  |  |  | fx = fraction number (molecular weight of fragment, as measured by SDS-PAGE)

Figure 32A. Identification of Proteins by Mass Spectrometry of Tryptic Fragments

| Band | Mass Spec Profile | Species | Acc. No. | Mass Spec Data | Mass Spec Database | Mass Difference | AAs | % Coverage | Comments |
|---|---|---|---|---|---|---|---|---|---|
| 1 | 4 peaks match with histone H1.c | human | 87668 (NCBI) | 1172.97 | 1172.37 | 0.60 | 110-121 | 22 | 15 MS peaks match with Band 2 |
|  |  |  |  | 1579.87 | 1579.71 | 0.16 | 65-79 |  |  |
|  |  |  |  | 1708.47 | 1707.89 | 0.58 | 64-79 |  |  |
|  |  |  |  | 2011.58 | 2012.32 | -0.74 | 35-54 |  |  |
| 2 | 3 peaks match with histone H1.c | human | 87668 (NCBI) | 1579.76 | 1579.71 | 0.05 | 65-79* | 16 | identification of starred peptide confirmed by sequence analysis |
|  |  |  |  | 1708.02 | 1707.89 | 0.13 | 64-79 |  |  |
|  |  |  |  | 2012.12 | 2012.32 | -0.20 | 35-54 |  |  |
| 3 | 7 peaks match with ribosome S20 | rat | R3RT20 (PIR) | 1129.76 | 1129.40 | 0.36 | 50-59 | 62 | 15 MS peaks match with Band 1 |
|  |  |  |  | 1156.21 | 1156.30 | -0.09 | 76-83 |  |  |
|  |  |  |  | 1334.46 | 1334.62 | -0.16 | 56-66 |  |  |
|  |  |  |  | 1352.13 | 1351.58 | 0.55 | 88-99 |  |  |
|  |  |  |  | 1518.04 | 1517.77 | 0.27 | 9-21 |  |  |
|  |  |  |  | 1919.02 | 1919.19 | -0.17 | 5-21 |  |  |
|  |  |  |  | 3404.02 | 3404.87 | -0.85 | 88-119 |  |  |
| 4 | 3 peaks match with Lysyl Oxidase RP | human | NP002309 (Swiss-Prot) | 1987.95 | 1988.27 | -0.32 | 150-167 | 8 | 12 MS peaks match with Band 8 |
|  |  |  |  | 2410.35 | 2410.63 | -0.28 | 648-669 |  |  |
|  |  |  |  | 2610.57 | 2610.10 | 0.47 | 455-478 |  |  |

Figure 32B. Identification of Proteins by Mass Spectrometry of Tryptic Fragments

| Band | Mass Spec Profile | Species | Acc. No. | Mass Spec Data | Mass Spec Database | Mass Difference | AAs | % Coverage | Comments |
|---|---|---|---|---|---|---|---|---|---|
| 5 | 9 peaks match with BMP-3 | human | 4557371 (NCBI) | 1113.32 | 1113.31 | 0.01 | 361-368 | 48 | % coverage calculation is relative to the mature BMP-3, 183 AAS (290-472) |
| | | | | 1438.53 | 1438.58 | -0.05 | 346-357 | | |
| | | | | 1566.76 | 1566.76 | 0.00 | 345-357 | | |
| | | | | 1651.86 | 1651.91 | -0.05 | 410-424 | | |
| | | | | 1794.09 | 1794.02 | 0.07 | 346-360 | | |
| | | | | 2268.46 | 2268.63 | -0.17 | 374-392 | | |
| | | | | 2424.45 | 2424.81 | -0.36 | 373-392 | | |
| | | | | 3409.15 | 3407.77 | 1.38 | 290-318* | | identification of starred peptide confirmed by sequence analysis |
| 6 | 3 peaks match with α2-Macroglobulin RAP | human | P30533 (Swiss-Prot) | 1002.24 | 1002.15 | 0.09 | 283-290 | 17 | |
| | | | | 2362.58 | 2362.43 | 0.15 | 129-150 | | |
| | | | | 3048.51 | 3048.52 | -0.01 | 257-282 | | |
| | 2 peaks match with BMP-3 | human | 4557371 (NCBI) | 1566.93 | 1566.75 | 0.18 | 346-357 | 15 | % coverage calculation is relative to the mature BMP-3, 183 AAS (290-472) |
| | | | | 1651.88 | 1651.91 | -0.03 | 410-424 | | |

Figure 32C. Identification of Proteins by Mass Spectrometry of Tryptic Fragments

| Band | Mass Spec Profile | Species | Acc. No. | Mass Spec Data | Mass Spec Database | Mass Difference | AAs | % Coverage | Comments |
|---|---|---|---|---|---|---|---|---|---|
| 7 | 4 peaks match with ribosome L32 | mouse | P17932 (Swiss-Prot) | 1033.25 | 1033.17 | 0.08 | 67-75 | 33 | |
| | 5 peaks match with BMP-3 | human | 4557371 (NCBI) | 1093.31 | 1093.40 | -0.09 | 1-10* | 21 | % coverage calculation is relative to the mature BMP-3, 183 AAS (290-472) |
| | | | | 1134.72 | 1134.28 | 0.44 | 65-74 | | |
| | | | | 1449.78 | 1449.66 | 0.12 | 19-29 | | |
| | | | | 1060.42 | 1060.20 | 0.22 | 102-111 | | |
| 8 | 1 peak matches with Lysyl Oxidase RP | human | NP002309 (Swiss-Prot) | 1113.39 | 1113.31 | 0.08 | 361-368 | 3 | 12 MS peaks match with Band 4 |
| | | | | 1360.26 | 1360.58 | -0.32 | 190-200 | | |
| | | | | 1652.28 | 1651.91 | 0.37 | 410-424 | | |
| | | | | 1793.62 | 1794.02 | -0.40 | 346-360 | | |
| | | | | 2410.37 | 2410.63 | -0.26 | 648-669 | | |
| 9 | 6 peaks match with BMP-3 | human | 4557371 (NCBI) | 1113.14 | 1113.31 | -0.17 | 361-368 | 36 | % coverage calculation is relative to the mature BMP-3, 183 AAS (290-472) |
| | | | | 1438.60 | 1438.58 | 0.02 | 346-357 | | |
| | | | | 1566.77 | 1566.76 | 0.01 | 345-357 | | |
| | | | | 1651.91 | 1651.61 | 0.30 | 410-424 | | |
| | | | | 2901.67 | 2901.19 | 0.48 | 41-66 | | |
| | | | | 3408.94 | 3407.77 | 1.17 | 290-318 | | |

Figure 32 D. Identification of Proteins by Mass Spectrometry of Tryptic Fragments

| Band | Mass Spec Profile | Species | Acc. No. | Mass Spec Data | Mass Spec Database | Mass Difference | AAs | % Coverage | Comments |
|---|---|---|---|---|---|---|---|---|---|
| 11 | 5 peaks match with BMP-3 | human | 4557371 (NCBI) | 1113.23 | 1113.31 | -0.08 | 361-368 | 48 | % coverage calculation is relative to the mature BMP-3, 183 AAS (290-472) |
| | | | | 1651.73 | 1651.91 | -0.18 | 410-424 | | |
| | | | | 1793.58 | 1794.02 | -0.44 | 346-360 | | |
| | | | | 2424.24 | 2424.81 | -0.57 | 373-392 | | |
| | | | | 3408.34 | 3407.77 | 0.57 | 290-318 | | |
| | 5 peaks match with ribosome L6 | human | Q02878 (Swiss-Prot) | 1140.38 | 1140.23 | 0.15 | 114-122 | 16 | |
| | | mouse | P47911 | 1526.88 | 1526.86 | 0.02 | 141-155 | | |
| | | | | 1059.15 | 1059.12 | 0.03 | 10-20 | | |
| 18 | 4 peaks match with TGF-β2 | human | P08112 (Swiss-Prot) | 1145.36 | 1145.35 | 0.01 | 262-271 | 52 | |
| | | | | 1386.74 | 1386.68 | 0.06 | 260-271 | | |
| | | | | 1101.20 | 1101.26 | -0.06 | 303-311 | | |
| | | | | 1175.26 | 1175.42 | -0.16 | 400-409 | | |
| | | | | 2240.37 | 2240.60 | -0.23 | 312-328 | | |
| | | | | 2691.70 | 2691.91 | -0.21 | 340-362 | | |
| | 5 peaks match with SPP24 | bovine | Q27967 (Swiss-Prot) | 1410.93 | 1411.60 | -0.67 | 42-53 | 30 | |
| | | | | 1447.59 | 1447.65 | -0.06 | 113-124 | | |
| | | | | 1540.64 | 1540.60 | 0.04 | 86-98 | | |
| | | | | 1869.10 | 1869.05 | 0.05 | 62-77 | | |
| | | | | 2268.47 | 2268.57 | -0.10 | 33-53 | | |

Figure 32 E.  Identification of Proteins by Mass Spectrometry of Tryptic Fragments

| Band | Mass Spec Profile | Species | Acc. No. | Mass Spec Data | Mass Spec Database | Mass Difference | AAs | % Coverage | Comments |
|---|---|---|---|---|---|---|---|---|---|
| 22 | 5 peaks match with TGF-β2 | human | P08112 (Swiss-Prot) | 1101.15 | 1101.26 | -0.11 | 303-311 | 63 | |
| | | | | 1175.13 | 1175.42 | -0.29 | 400-409 | | |
| | | | | 2084.16 | 2084.42 | -0.26 | 312-347 | | |
| | | | | 2240.25 | 2240.60 | -0.35 | 312-328 | | |
| | | | | 2691.61 | 2691.91 | -0.30 | 340-362 | | |
| | 2 peaks match with SPP24 | bovine | Q27967 (Swiss-Prot) | 1411.23 | 1411.60 | -0.37 | 42-53 | 11 | |
| | | | | 1447.40 | 1447.65 | -0.25 | 113-124 | | |
| | 5 peaks match with histone H1.x | human | JC4928 (PIR) | 1208.46 | 1208.40 | 0.06 | 48-57 | 14 | |
| | | | | 1221.71 | 1222.35 | -0.64 | 107-118 | | |
| | | | | 1349.85 | 1350.52 | -0.67 | 107-119 | | |
| | | | | 1364.57 | 1364.59 | -0.02 | 48-58 | | |
| | | | | 1732.23 | 1732.97 | -0.74 | 43-57 | | |
| 25 | 5 peaks match with BMP-3 | human | 4557371 (NCBI) | 1060.43 | 1060.20 | 0.23 | 102-111 | 31 | % coverage calculation is relative to the mature BMP-3, 183 AAS (290-472) |
| | | | | 1438.83 | 1438.58 | 0.25 | 346-357 | | |
| | | | | 1566.92 | 1566.76 | 0.16 | 345-357 | | |
| | | | | 1651.80 | 1651.91 | -0.11 | 410-424 | | |
| | | | | 3408.86 | 3407.77 | 1.09 | 290-318 | | |

Figure 32F.  Identification of Proteins by Mass Spectrometry of Tryptic Fragments

| Band | Mass Spec Profile | Species | Acc. No. | Mass Spec Data | Mass Spec Database | Mass Difference | AAs | % Coverage | Comments |
|---|---|---|---|---|---|---|---|---|---|
| 29 | 4 peaks match with BMP-3 | human | 4557371 (NCBI) | 1113.22 | 1113.31 | -0.09 | 361-368 | 27 | % coverage calculation is relative to the mature BMP-3, 183 AAS (290-472) |
| | | | | 1438.70 | 1438.58 | 0.12 | 346-357 | | |
| | | | | 1566.86 | 1566.75 | 0.11 | 345-357 | | |
| | | | | 3409.04 | 3407.77 | 1.27 | 290-318 | | |

FIGURE 34: Quantitation of Identified BP proteins

| Identified Protein | Percentage of Total Protein |
|---|---|
| LORP | 2 |
| BMP-3 | 11 |
| BMP-3 and A2-MG | 3 |
| RL6 & BMP-3 | 4 |
| Histone | 3 |
| Histone | 3 |
| Histone & BMP-3 | 4 |
| BMP-3 | 8 |
| RL32 & BMP-3 | 8 |
| RS2D | 5 |
| SPP24 & TGF-$\beta$2 | 6 |
| Total | 58% |

METHODS AND COMPOSITIONS FOR TREATING INTERVERTEBRAL DISC DEGENERATION

FIELD OF THE INVENTION

This invention relates generally to methods and compositions useful in treating intervertebral disc impairment in humans and other mammals. More particularly, this invention concerns compositions useful in restoring hydrodynamic function and stimulating cell proliferation and extracellular matrix production in intervertebral discs that have been compromised by injury, degenerative disease, congenital abnormalities, and/or the aging process.

Compositions of the invention may be injectable, and may include growth factors, bioactive agents, and living cells. The compositions are useful for restoring, improving, or augmenting hydrodynamic function of the intervertebral disc, increasing intervertebral disc height, and stimulating cell proliferation and/or extracellular matrix production in intervertebral discs.

BACKGROUND

The human vertebral column (spine) comprises a plurality of articulating bony elements (vertebrae) separated by soft tissue intervertebral discs. The intervertebral discs are flexible joints which provide for flexion, extension, and rotation of the vertebrae relative to one another, thus contributing to the stability and mobility of the spine within the axial skeleton.

The intervertebral disc is comprised of a central, inner portion of soft, amorphous mucoid material, the nucleus pulposus, which is peripherally surrounded by an annular ring of layers of tough, fibrous material known as the annulus fibrosus. The nucleus pulposus and the annulus fibrosus together are bounded on their upper and lower ends (i.e., cranially and caudally) by vertebral end plates located at the lower and upper ends of adjacent vertebrae. These end plates, which are composed of a thin layer of hyaline cartilage, are directly connected at their peripheries to the lamellae of the inner portions of the annulus fibrosus. The lamellae of the outer portions of the annulus fibrosus connect directly to the bone at the outer edges of the adjacent vertebrae.

The soft, mucoid nucleus pulposus contains chondrocytes, which produce fibrils of collagen (primarily Type II collagen, but also Types IX, XI, and others) and large molecules of negatively charged, sulfated proteoglycans, as depicted in FIGS. 1 and 1A. The term matrix as used herein refers to a composition which provides structural support for, and which facilitates respiration and movement of nutrients and water to and from, an intervertebral disc. The collagenous components of the nucleus pulposus extracellular matrix comprise a scaffold that provides for normal cell (i.e., chondrocyte) attachment and cell proliferation. The negatively charged proteoglycan component of the nucleus pulposus extracellular matrix attracts water to form a hydrated gel, which envelops the collagen fibrils and chondrocyte cells. In the normal healthy nucleus pulposus, water comprises between 80–90% of the total weight.

The nucleus pulposus thus plays a central role in maintaining normal disc hydrodynamic function. The large molecular weight proteoglycans are contained within the nucleus pulposus by the annulus fibrosus and by the vertebral end plates, and they attract water into the nucleus through sieve-like pores in the end plates. The resulting osmotic pressure within each disc tends to expand it axially (i.e., vertically), driving the adjacent vertebrae further apart. On the other hand, mechanical movements resulting in axial compression, flexion, and rotation of the vertebrae exert forces on the intervertebral discs, which tends to drive water out of the nucleus pulposus. Water movements into and out of an intervertebral disc under the combined influence of osmotic gradients and mechanical forces constitute hydrodynamic functions important for maintaining disc health.

Movement of solutes in the water passing between discs and vertebrae during normal hydrodynamic function facilitates chondrocyte respiration and nutrition within the discs. This function is critical to chondrocyte survival since nucleus pulposus tissues of intervertebral discs are avascular (the largest such avascular structures in the human body). Maintaining sufficient water content in the nucleus pulposus is also important for absorbing high mechanical (shock) loads, for resisting herniation of nucleus pulposus matter under such loads, and for hydrating the annulus fibrosus to maintain the flexibility and strength needed for spine stability.

Normal hydrodynamic functions are compromised in degenerative disc disease (DDD). DDD involves deterioration in the structure and function of one or more intervertebral discs and is commonly associated with aging and spinal trauma. Although the etiology of DDD is not well understood, one consistent alteration seen in degenerative discs is an overall decrease in proteoglycan content within the nucleus pulposus and the annulus fibrosus. The loss in proteoglycan content results in a concomitant loss of disc water content. Reduced hydration of disc structures may weaken the annulus fibrosus, predisposing the disc to herniation. Herniation frequently results in extruded nucleus pulposus material impinging on the spinal cord or nerves, causing pain, weakness, and in some cases permanent disability.

Because adequate disc hydration is important for stability and normal mobility of the spine, effective treatment of DDD would ideally restore the disc's natural self-sustaining hydrodynamic function. Such disc regeneration therapy may require substantial restoration of cellular proteoglycan synthesis within the disc to maintain the hydrated extracellular matrix in the nucleus pulposus. Improved hydrodynamic function in such a regenerated disc may result in restoration and reestablishment of intervertebral disc height. It may also provide for improved hydration of the annulus fibrosus, making subsequent herniation less likely.

Prior art approaches to intervertebral disc problems fail to restore normal self-sustaining hydrodynamic function, and thus may not restore normal spinal stability and/or mobility under high loads. One approach to reforming intervertebral discs using a combination of intervertebral disc cells and a bioactive, biodegradable substrate is described in U.S. Pat. No. 5,964,807 to Gan et al., incorporated herein by reference. The biodegradable substrate disclosed in Gan et al., including bioactive glass, polymer foam, and polymer foam coated with sol gel bioactive material, is intended to enhance cell function, cell growth and cell differentiation. The bioactive glass contains oxides of silicon, sodium, calcium and phosphorus. The polymer foam is described as biocompatible and includes polyglycolide (PGA), poly (D,L-lactide) (D,L-PLA), poly(L-lactide) (L-PLA), poly(D,L-lactide-co-glycolide) (D,L-PLGA), poly(L-lactide-co-glycolide) (L-PLGA), polycaprolactone (PCL), polydioxanone, polyesteramides, copolyoxalates, and polycarbonates. Gan et al. describes application of this approach to intervertebral disc reformation in mature New Zealand rabbits, concluding with ingrowth of cells and concurrent degradation of implanted material with little or no inflammation. However, degradation of portions of the implanted material, such as acidic breakdown of PLAs, PGAs and PLGAs, may adversely affect cell growth, cell function and/or cell differentiation.

A somewhat analogous disclosure relating to tissues for grafting describes matrix particulates comprising growth factors that may be seeded with cells; see U.S. Pat. No. 5,800,537 to Bell, incorporated herein by reference. The matrix and cells are applied to scaffolds, which include biodegradable polymers, microparticulates, and collagen which has been cross-linked by exposure to ultraviolet radiation and formed to produce solids of foam, thread, fabric or film. The matrix particulates are derived from tissue from which cells and cell remnants have been removed without removing factors necessary for cell growth, morphogenesis and differentiation. Bell specifically avoids the use of reagents like high salt, or deliysidation reagents such as butanol/ether or detergents. Such reagents are unfavorably characterized as being responsible for removing from the source tissue factors essential for stimulating repair and remodeling processes. Alternative approaches, in which such factors are obtained from other sources rather than being retained in the tissue, are not addressed.

Still another disclosure related to regeneration of cartilage is found in U.S. Pat. No. 5,837,235 to Mueller et al., incorporated herein by reference. Mueller et al. describes committing small particles of autologous omentum or other fatty tissue for use as a carrier, and adding to the carrier growth factors such as Transforming Growth Factor Beta and Bone Morphogenic Protein. Mueller et al. does not teach cross-linking tissues to create a cross-linked matrix.

The Gan et al. patent above is representative of past attempts to restore or regenerate substantially natural hydrodynamic disc function to intervertebral discs, but such techniques have not been proven in clinical trials. Similarly, the approaches of Bell and Mueller et al. have not been widely adapted for disc regeneration, and better approaches are still needed because low back pain sufficient to prevent the patient from working is said to affect 60% to 85% of all people at some time in their life. In the absence of safer and more efficacious treatment, an estimated 700,000 discectomies and 550,000 spinal fusions are performed worldwide each year to treat these conditions. Several prosthetic devices and compositions employing synthetic components have also been proposed for replacement of degenerated discs or portions thereof. See, for example, U.S. Pat. Nos. 4,772,287, 4,904,260, 5,047,055, 5,171,280, 5,171,281, 5,192,326, 5,458,643, 5,514,180, 5,534,028, 5,645,597, 5,674,295, 5,800,549, 5,824,093, 5,922,028, 5,976,186, and 6,022,376.

A portion of the disc prostheses referenced above comprise hydrogels which are intended to facilitate hydrodynamic function similar in some respects to that of healthy natural discs. See, for example, U.S. Pat. No. 6,022,376 (Assell et al.). These prosthetic hydrogels, however, are not renewed through cellular activity within the discs. Thus, any improvement in disc hydrodynamic function would not be self-sustaining and would decline over time with degradation of the prosthetic hydrogel. Healthy intervertebral discs, in contrast, retain their ability to hydrodynamically cushion axial compressive forces in the spine over extended periods because living cells within the discs renew the natural hydrogel (i.e., extracellular matrix) component.

Restoration of a clinically useful degree of normal hydrodynamic function in degenerated intervertebral discs is an object of the present invention, and the methods and compositions described herein have been shown to induce and/or enhance such regeneration.

SUMMARY OF THE INVENTION

The present invention comprises methods and compositions for intervertebral disc regeneration. In preferred embodiments, the compositions comprise a three-dimensional fluid matrix of digestion-resistant, cross-linked nucleus pulposus tissue from a donor vertebrate. The donor may be the patient or another animal of the same or different species. Cross-linking of donor nucleus pulposus tissue for the present invention is preferably achieved through use of one or more photooxidative catalysts which selectively absorb visible light. See U.S. Pat. Nos. 5,147,514, 5,332,475, 5,817,153, and 5,854,397, all incorporated herein by reference. Other cross-linking approaches may be used without departing from the scope of the invention, however.

Prior to cross-linking the tissues, chondrocytes of the donor vertebrate are preferably destroyed, fragmented, and/or removed (i.e., decellularized). A preferred decellularization approach involves soaking the tissue in a solution having high concentrations of salt (preferably NaCl) and sugar (preferably sucrose). Such high-salt, high-sugar solutions are referred to as HSHS solutions. Other decellularization approaches may be used, however. After the tissues are decellularized and cross-linked, the resulting fluid matrix may be lyophilized for sterilization and storage, and then rehydrated prior to use. FIG. 2 illustrates a process for producing a preferred embodiment of the fluid matrix of the present invention.

The fluid matrix of the present invention is biocompatible, substantially non-immunogenic, and resistant to degradation in vivo. As such, it is capable of providing important internal structural support for an intervertebral disc undergoing regeneration during a period of accelerated proteoglycan synthesis. The cross-linked matrix may be delivered to the intervertebral disc space by injection through a syringe (as depicted in FIG. 2), via a catheter, or other methods known in the art.

The three-dimensional fluid matrix of the present invention may be used alone or in combination with growth factors and/or living cells to facilitate regeneration of the structures of a degenerated disc. In patients having sufficient viable endogenous disc cells (chondrocytes) and cell growth factors, the three-dimensional cross-linked matrix alone may substantially contribute to the regeneration of hydrodynamic function in an intervertebral disc in vivo by providing improved mechanical stability of the disc and a more favorable environment for cellular growth and/or metabolism. Conversely, in another embodiment of the invention, a combination of the three-dimensional matrix and one or more purified, preferably bone-derived, cell growth factors may also be used to treat DDD in discs containing viable chondrocytes in a depleted proteoglycan hydrogel matrix. In this case, the cross-linked collagen provides an expanded remodelable three-dimensional matrix for the existing (native) chondrocytes within a disc, while the cell growth factors induce accelerated proteoglycan production to restore the hydrogel matrix of the patient. The combination of the three-dimensional matrix and one or more purified cell growth factors is referred to as a cell growth medium. The present invention may also comprise an injectable cell growth medium. Individual purified cell growth factors may be obtained by recombinant techniques known to those skilled in the art, but a preferred plurality of bone-derived purified cell growth factors for the present invention is disclosed in U.S. Pat. Nos. 5,290,763, 5,371,191 and 5,563,124, all incorporated herein by reference. Bone-derived cell growth factors produced according to these patents are hereinafter referred to as "BP."

Disc regeneration occurs as the cross-linked collagen and proteoglycan matrix supports living cells (which may include exogenous cells as well as native disc or other autologous cells) having inherent capability to synthesize Type II collagen fibrils and proteoglycans in vivo, among other extracellular matrix molecules. Where the patient's native disc cells have been removed or are otherwise insufficient to cause such proliferation, living cells may be added to the three-dimensional matrix of cross-linked nucleus pulposus material to further promote disc regeneration. Accordingly, in another embodiment, the present invention comprises a three-dimensional matrix of cross-linked nucleus pulposus tissue to which exogenous and/or autologous living cells have been added. The injectable combination of three-dimensional matrix material and exogenous and/or autologous living cells is termed herein an injectable cell matrix. Suitable cells for such an injectable cell matrix may be obtained, for example, from the nucleus pulposus of a mammalian vertebral disc, from cartilage, from fatty tissue, from muscle tissue, from bone marrow, or from bone material (i.e., mesenchymal stem cells), but are not limited to these tissue types. These cells are preferably cultured in vitro to confirm their viability and, optionally, to increase the cells' proliferation and synthesis responses using cell growth factors.

Growth factors may optionally be added to cell cultures to stimulate cellular development and elaboration of Type II collagen fibrils and proteoglycans suitable for maintaining an effective disc hydrogel matrix in vivo. An injectable fluid combining purified cell growth factors and a plurality of living cells is termed an injectable cell suspension, and is useful in treating DDD. While an injectable cell matrix alone (i.e., without growth factors) may substantially regenerate hydrodynamic function in an intervertebral disc in vivo if sufficient native cell growth factors are present in the disc, purified (exogenous) cell growth factors may be added to an injectable cell matrix of the present invention to form yet another embodiment of the present invention.

BRIEF DESCRIPTION OF THE DRAWINGS

FIG. 1A is a diagram illustrating an enlarged proteoglycan aggregate.

FIGS. 4A and 4B provide a photographic comparison of H & E (hematoxylin and eosin) stained sections of fresh porcine nucleus pulposus tissue (FIG. 4A) and a cross-linked matrix of the present invention (FIG. 4B), both at 300× magnification.

FIG. 7 is a diagram of an experimental process used to demonstrate stimulation of sheep cell ingrowth, proliferation, and new matrix synthesis in an embodiment of the present invention comprising a cross-linked matrix combined with bone protein growth factors (BP).

FIG. 8 is a graph and a photograph indicating the results of an Alcian blue assay for matrix production in sheep nucleus pulposus cells stimulated by growth factors.

FIG. 9 is a graph indicating the results of immunogenicity tests for a cross-linked matrix of the present invention in rabbit immunizations and sheep serum.

FIG. 10 is a diagram of the protocol for an in vivo study of a matrix and growth factor combination of the present invention.

FIG. 11 is a radiograph of a vertebral column from a sheep sacrificed at 2 months after an injection of a matrix and growth factor combination in an in vivo study of an embodiment of the present invention.

FIG. 12 is a photographic reproduction of histology slides of vertebral discs of a sheep sacrificed at 2 months after an injection of a matrix and growth factor combination of the present invention.

FIG. 13 is a radiograph of a vertebral column of a sheep sacrificed at 4 months after an injection of a matrix and growth factor combination in an in vivo study of the present invention.

FIG. 14 is a photographic reproduction of histology slides of vertebral discs of a sheep sacrificed at 4 months after an injection of a matrix and growth factor combination of the present invention.

FIG. 17 is a graph depicting the results of an Alcian blue assay for proteoglycan synthesis in baboon intervertebral disc cells stimulated by growth factor.

FIGS. 23A–23O are Mass Spectrometer results for tryptic fragments.

FIG. 26 is a PAS (periodic acid schiff) stained SDS-PAGE gel of HPLC fractions.

FIG. 27 is an anti-BMP-7 stained SDS-PAGE gel of PNGase F treated BP.

FIG. 28 is an anti-BMP-2 stained SDS-PAGE gel of PNGase F treated BP.

FIG. 30 is a chart showing antibody listing and reactivity.

FIGS. 31A–31B together comprise a chart showing tryptic fragment sequencing data.

FIGS. 32A–32F together comprise a chart showing tryptic fragment mass spectrometry data.

FIG. 34 is a chart illustrating the relative mass of major components of BP.

DETAILED DESCRIPTION OF ILLUSTRATIVE EMBODIMENTS

Figure 1:
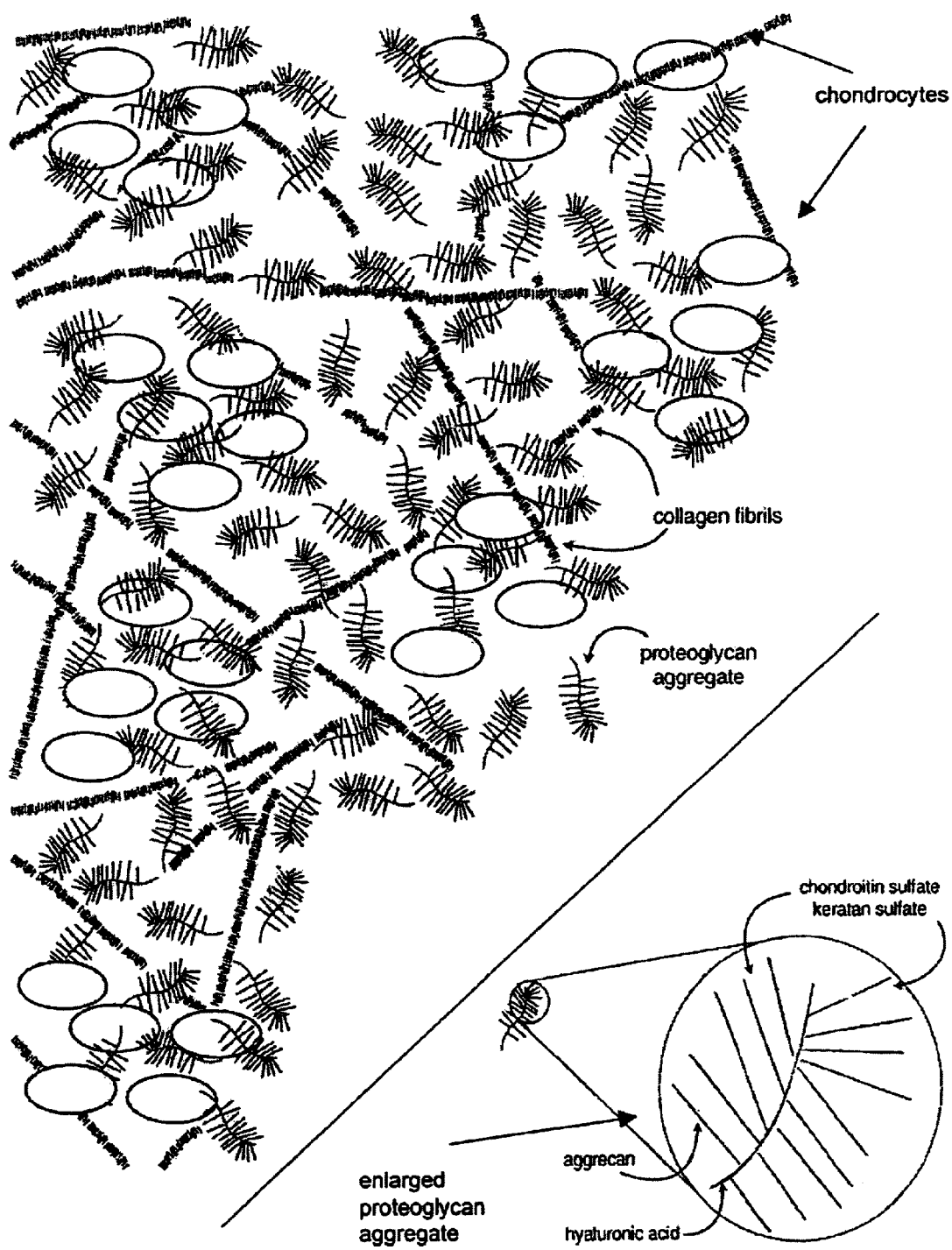
FIG. 1 is a diagram illustrating components of healthy nucleus pulposus tissue in a vertebrate.

In a preferred embodiment, the invention comprises a biodegradable matrix, which is delivered as an incompressible fluid to induce and/or enhance regeneration or repair of tissues in the intervertebral disc. The biodegradable matrix comprises hydrophilic molecules, which will maintain and/or increase the "captured" water content in intervertebral disc tissues. The biodegradable matrix may also serve as a carrier substrate for added growth factors and/or appropriate living cell types.

Since the biodegradable matrix of the present invention is a viscous fluid, it furnishes incompressible support when delivered within a closed, secure disc space. Moreover, because it is distributed uniformly within a disc, the present fluid matrix has a force distribution effect, hydraulically transmitting forces evenly inside the disc. The matrix thus provides resistance against axial compression and annulus collapse, whereas other matrix materials (for example, polymer sponges and collagen sponges) will rapidly collapse under the axial compressive forces within the disc. Solid matrix materials, in contrast, will concentrate forces from end plates directly onto implants, leading to rapid deterioration of implants and/or end plates.

In a preferred embodiment, the biodegradable matrix of the present invention is injectable. Clinical application to a patient can thus be accomplished using minimally invasive techniques, significantly reducing both the cost of treatment and the likelihood of complications relative to procedures such as partial discectomy or vertebral fusion. Similarly, the present invention avoids the requirement for boring a hole into the annulus to implant a prosthetic replacement nucleus pulposus device, such as a relatively solid biodegradable matrix, or to evacuate nucleus tissue to create space for an implanted biodegradable substrate.

The matrix of the present invention is a natural material, preferably prepared from normal, healthy nucleus tissue of animals and/or humans. Accordingly, the matrix is comprised of proteins and matrix molecules especially adapted for efficient hydrodynamic function in intervertebral discs. Such a matrix remains biodegradable under normal circumstances in the presence of specific cellular enzymes, albeit at a slower rate than endogenous disc matrix. It is an important feature of the invention that matrix breakdown products associated with the present invention are digestible by disc cells. In comparison, some matrix materials previously taught (e.g. polyvinyl alcohol) do not break down by physiological processes. In addition, some synthetic polymer substrates create acidic degradation byproducts, in particular PGA and PLA.

Immediate (substantially homogeneous) dispersion of cells within the present matrix is another advantage of the invention. The viscous fluid formulation preferred for injection can be mixed directly with cells of the appropriate type(s) and then delivered immediately to treat an intervertebral disc. In the matrix of the present invention it is not necessary to culture cells and matrix together for some days or weeks before implantation, as it is for certain matrix materials such as PGA and collagen sponges.

The matrix of the present invention is an appropriate substrate for cells, uniquely suited to the ingrowth, proliferation, and residence of intervertebral disc cells. Intervertebral disc cells preferentially grow into and survive in the matrix of the present invention, compared to type I collagen sponges fixed with formalin or glutaraldehyde.

The following examples illustrate the preparation of preferred embodiments of the invention and demonstrate its non-immunogenic and disc regenerative properties.

EXAMPLE 1

Preparation of a Cross-Linked, Fluid Matrix Suitable for Treatment of Degenerative Disc Disease A three-dimensional fluid matrix of cross-linked nucleus pulposus tissue in accordance with an embodiment of the present invention may be prepared from donor vertebrates. Although porcine donors were used in a particularly preferred embodiment, nucleus pulposus tissues from other vertebrates may also be used, although mammalian vertebrates are preferred (e.g., human, porcine, bovine, ovine, etc.).

Although nucleus pulposus tissues may be harvested by a variety of methods from many vertebral donors, in a preferred embodiment nucleus pulposus tissues were dissected aseptically from spinal intervertebral discs of pigs. In a sterile environment (i.e., a laminar flow hood), the annulus fibrosus of porcine donors was sliced radially and the vertebral end plates separated to expose the nucleus pulposus. The latter material was curetted out of the central portion of the disc, devoid of annulus and end plate tissues.

The nucleus pulposus tissues thus harvested were inserted into sterile dialysis (filter) tubing having a preferred molecular weight cutoff of about 3500 Daltons to substantially prevent loss of low molecular weight proteoglycans from the tissues while substantially reducing bacterial or other contamination. Other semipermeable membranes or filtering membrane types may be used to perform these functions.

The nucleus pulposus tissues to be cross-linked are also preferably treated to destroy and remove donor cells and/or cell fragments. To this end, dialysis tubing containing nucleus pulposus tissues was submerged in a high-salt, high-sucrose (HSHS) solution of about 2.2%: 8.4% w/v (respectively) for about 48 hours. Concentration ranges for the HSHS solution may be from 1% to 50%, but a preferred HSHS solution contains 220 grams NaCl and 837.5 grams of sucrose in 10L water. Preferred HSHS incubation times are from about 24 to about 72 hours, although shorter or longer times may also advantageously be used. Exposure to this HSHS solution results in osmotic destruction and fragmentation of native chondrocyte cells (decellularization), and further results in denaturation of soluble cellular proteins and nucleic acids. The HSHS solution may also contain other reagents which further degrade nucleic acids (including but not limited to sulfones and nucleases), and other reagents which can extract membrane lipids (including but not limited to alcohol, chloroform, and methanol). Although native cells of the donor may be retained in other embodiments of the invention, decellularization and denaturation are preferred where exogenous (particularly xenogeneic) tissues are used, so as to reduce the potential for immunogenic responses. Processes other than exposure to HSHS solutions may be used for his purpose.

Cross-linking of the nucleus pulposus tissues is preferably accomplished by a photo-mediated process in accordance with U.S. Pat. Nos. 5,147,514, 5,332,475, 5,817,153, and/or 5,854,397. In one such process, a photoactive dye (methylene blue) was dissolved in the HSHS solution at a preferred dye concentration of about 20 mg/liter. The photoactive dye was allowed to permeate the nucleus tissues within the dialysis tubing during the initial storage/decellularization process in HSHS. A wide range of photoactive dyes and concentrations, as taught in the foregoing patents, may be used to obtain cross-linked fluid matrices suitable for use in regenerating mammalian disc tissues. Preferred dyes include methylene blue and methylene green at concentrations of about 0.001% to about 1.0% w/v.

Figure 2:
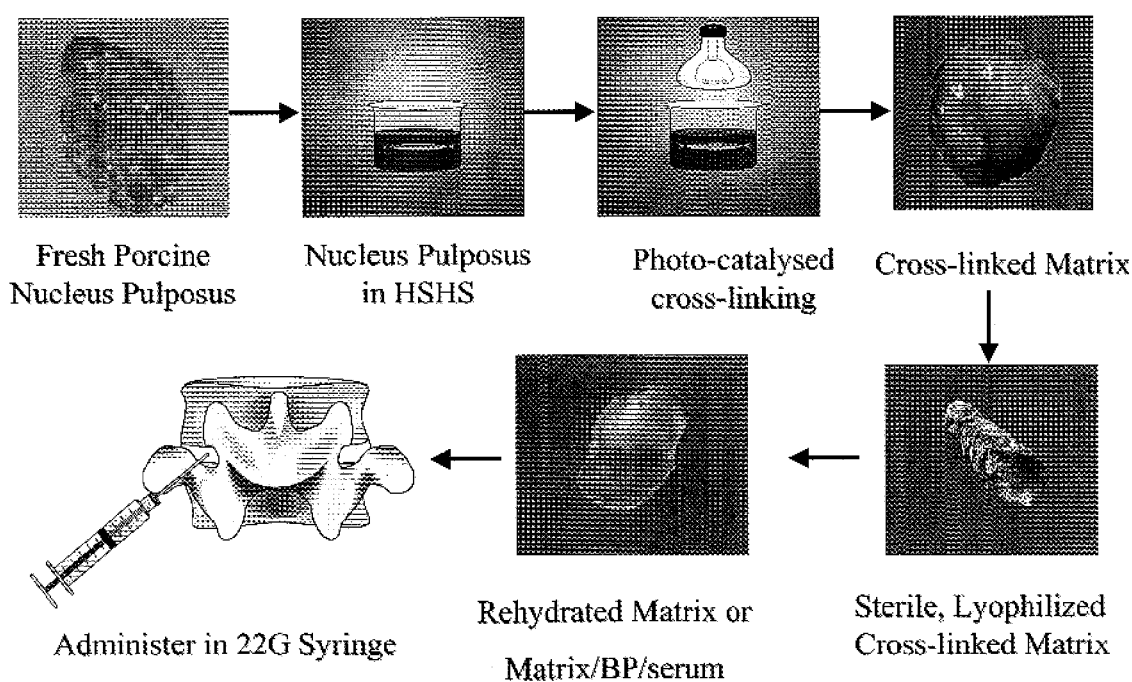
FIG. 2 is a diagram illustrating a process for preparation and use of a cross-linked matrix of porcine nucleus pulposus tissue in a preferred embodiment of the invention.

To cross-link the collagen within the nucleus tissues, the dialysis tubing containing the dye-permeated nucleus tissues was placed in a photooxidation chamber and exposed to broad-spectrum visible light for 48 hours. In preferred embodiments of the invention, the tissues may be cross-linked from about 24 to about 72 hours. A solution of methylene blue in phosphate buffered saline (PBS) was maintained under controlled temperature at 10° C. and circulated around the dialysis tubing within the photooxidation chamber to provide substantially constant temperature regulation of the nucleus tissues. Precise temperature control is not critical to the practice of the invention; however, maintaining a relatively cooler temperature is preferred to avoid damaging the tissues. Following photo-cross-linking of the collagen, the treated nucleus tissues were collected, lyophilized in a vacuum under centrifugation, and finely pulverized in a freezer-mill under liquid nitrogen. The cross-linked matrix product thus prepared can be sterilized using gamma radiation, ethylene oxide (or other sterilants) and stored at −80° C. until rehydrated for use. A preferred process for preparing a matrix according to the present invention is illustrated in FIG. 2.

In addition to preparation of the cross-linked matrix, control (non-crosslinked) tissues were prepared following the above procedures, except that they were not exposed to light. These control, non-crosslinked tissues were used for comparison purposes.

Figure 6:
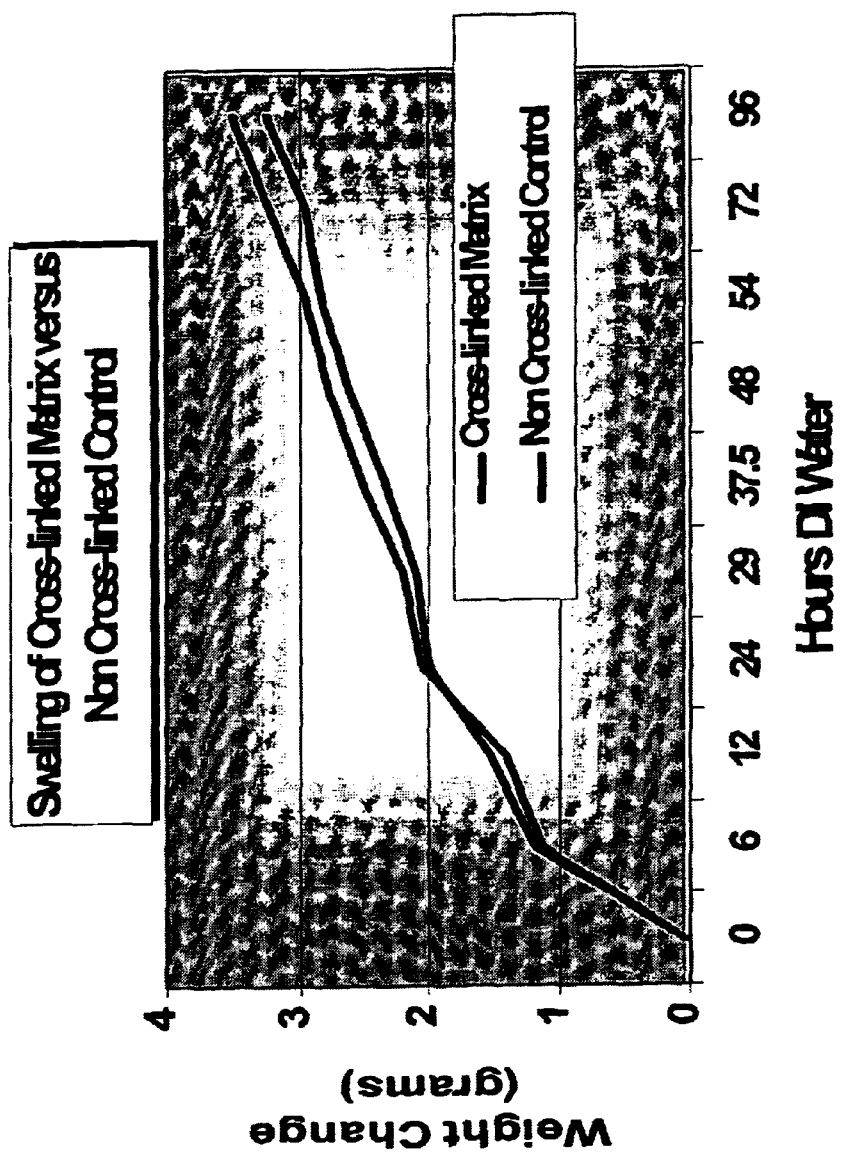
FIG. 6 is a comparison graph of the hydraulic/swelling capacity of a cross-linked matrix of the present invention and a non-cross-linked control.

To investigate the swelling capacity of cross-linked matrix versus non-crosslinked control, lyophilized samples of cross-linked matrix and non-crosslinked control were suspended in water and the increase in weight due to water absorption was measured at various times from 0 to 96 hours. As illustrated in FIG. 6, the cross-linked matrix retained 95% of the hydraulic capacity of the non-crosslinked control.

EXAMPLE 2

Testing of Fluid Matrix to Evaluate Protein Modification Induced by the Cross-Linking Process One half gram of the matrix material obtained prior to the lyophilization step of EXAMPLE 1 was placed in 15 mls of a solution of 4 M guanidine hydrochloride and agitated on a shaker for 24 hours to solubilize proteoglycans. After centrifugation, the supernatant was discarded and the pellet washed in distilled water 3 times for 5 minutes each. The pelleted matrix material was then removed and blot-dried on filter paper.

One hundred mg of the blot-dried matrix was placed in a 1.5 ml microcentrifuge tube with 1000 μl of 1% sodium dodecyl sulfate (SDS) containing 5% beta-mercaptoethanol (BME). The matrix in SDS/BME was boiled for one hour to extract proteins (e.g., collagens). Samples were then centrifuged at 12000 rpm for 1 hour and aliquots of the supernatant were subjected to electrophoresis in gradient polyacrylamide gels.

Figure 3:
FIG. 3 is a photographic reproduction of an SDS-PAGE (sodium dodecyl sulfate polyacrylamide gel electrophoresis) analysis comparing the amount of proteins extracted from a cross-linked matrix of the present invention with a non-cross-linked control.

Gels were stained with Coomassie blue or silver to visualize proteins extracted by the SDS/BME and heat treatment. As illustrated in FIG. 3, collagen bands stained prominently in control, non-cross-linked tissues but exhibited only faint staining in cross-linked matrix. These results demonstrated that in the cross-linked matrix material, collagen proteins were not easily extracted by the above treatment, indicating that cross-linking had occurred. In contrast, stained gels of the control tissues demonstrated that collagen proteins were readily extracted from non-crosslinked material by the above treatment. See FIG. 3.

EXAMPLE 3

Matrix Histology to Evaluate Cellular Debris and Residual Membranous Material

Cross-linked matrix material obtained prior to the lyophilization step of Example 1 was placed in 4% paraformaldehyde for tissue fixation. Standard histology techniques of embedding, sectioning, and staining of sections with hematoxylin & eosin dyes were performed. Visualization of cross-linked matrix in H & E-stained sections demonstrated that the matrix preparation process facilitates destruction of cellular membranes and intracellular elements, with minimal membrane material remaining as compared to fresh porcine nucleus pulposus material as well as non-crosslinked tissue decellularized by HSHS treatment, freeze-thaw cycles, and HSHS treatment plus freeze-thaw cycles. See FIGS. 4A and 4B.

EXAMPLE 4

Evaluation of Matrix Antigenic Reactivity Using Monoclonal Antibodies to Type II Collagen Cross-linked matrix material obtained prior to the lyophilization step of Example 1 was also subjected to pepsin digestion to cleave Type II collagen proteins. The protein digests were run on SDS/PAGE and then transferred to a nitrocellulose membrane. Total protein transferred to the membrane was visualized using Colloidal Gold.

Figure 5:
FIG. 5 is a photographic reproduction of a stained nitrocellulose membrane comparing the reactivity of Type II collagen digested from a cross-linked matrix of the present invention and a non cross-linked control.

The visualized nitrocellulose membranes were incubated with a mouse monoclonal antibody to Type II collagen and a secondary antibody (anti-mouse) conjugated with alkaline phosphatase. The antibody reactivity was visualized through addition of alkaline phosphatase substrate. As depicted in FIG. 5, the antibodies toward Type II collagen did not react with pepsin digests of the cross-linked matrix as much as with the pepsin digests of the non-crosslinked control tissue. The results indicate that the matrix of the invention may have reduced antigenic epitopes for Type II collagen, and thus have less immunogenicity than non-crosslinked tissues. See FIG. 5.

EXAMPLE 5

Evaluation of Matrix Immunogenicity in Rabbit Antisera Production

One gram of the lyophilized and pulverized matrix material prepared according to EXAMPLE 1 was dispersed in PBS (i.e., rehydrated) and centrifuged. The protein concentration of the supernatant was then determined using the BCA assay and the supernatant was diluted with PBS to a final concentration of 200 µg of protein per ml of PBS. The diluted supernatant was then sterilized for injection protocols. Three rabbits were immunized with 100 µg of protein from the sterilized supernatant. Each rabbit received 9 immunizations over a 14 week period and sera was collected from the rabbits on a regular schedule.

Antisera production against the protein extract was measured using an enzyme-linked immunosorbent assay (ELISA). Type II collagen was included as a positive control in the ELISA. Colorimetric evaluation of antisera directed against the matrix material demonstrated very low immunogenicity in rabbits. See FIG. 9.

EXAMPLE 6

Matrix Formulation Including Serum and Other Fluids For Injections And Delivery One gram of the lyophilized and pulverized matrix material prepared according to EXAMPLE 1 was sterilized with 70% ethanol and the ethanol was removed by successive PBS rinses. The dispersed matrix was centrifuged and the pellet was suspended in heat-inactivated sheep serum at a ratio of 0.5 g lyophilized matrix to 1 ml serum to prepare a viscous fluid matrix which can be loaded into a standard syringe and delivered via a small gauge needle. In preferred embodiments of the invention, the serum is collected from the vertebrate animal or human patient to be treated, heat-inactivated to destroy unwanted protein components (complement proteins), and passed through a 0.2 micron sterile filtration unit. Different matrix/serum ratios may also be advantageously employed. Ratios ranging from 0.1 g to 2.0 g of lyophilized matrix to 1 ml of serum are preferred.

Serum is a preferred fluid for mixture and delivery of the cross-linked matrix of the present invention because it contains various intrinsic growth factors that are beneficial to intervertebral disc cells. Serum also serves as a suitable carrier for extrinsic protein growth factors and/or small molecules. The beneficial effects of extrinsic growth factors on intervertebral disc cells are enhanced by the addition of serum.

Other fluids are also suitable for mixture and delivery of the viscous fluid matrix. For example, sterile saline or sterile water may also be used. The examples herein are not meant to be limiting as to the variety of carrier fluids which may be used to mix and deliver the matrix in the present invention.

EXAMPLE 7

Injection of Matrix Formulation To Intervertebral Discs Using Pressure-Mediated Syringe Matrix material was prepared according to EXAMPLE 6 (mixed with serum) to form a viscous fluid and loaded into a standard syringe having a small gauge needle (e.g., 18–31 gauge) attached. Syringe injection pressure can be controlled simply by the fingers of the hand. In other embodiments of the invention, pressure to inject the viscous fluid can be controlled by an external device which concomitantly measures (e.g., via a pressure transducer) and delivers (e.g., by compressed air) a predetermined force to the syringe plunger.

In one preferred embodiment of this device, a thermal element is included in the needle. By providing a needle having a thermal element, it is possible to deliver heat to the outer layers of the annulus fibrosus at the end of the treatment and during removal of the syringe needle in order to shrink collagen fibers around the needle and effectively seal the site of needle penetration.

It is further contemplated that the matrix of the present invention can be delivered to the disc space of a patient transpedicularly (i.e., through the pedicle of the vertebrae). In particular, the cross-linked matrix can be administered percutaneously via a biopsy cannula inserted through a channel in the pedicle. After delivery of the matrix, the channel can then be filled with bone cement or other like material to seal the channel.

EXAMPLE 8

Isolation of Human, Sheep, and Baboon Intervertebral Disc Nucleus Pulposus Cells Human intervertebral nucleus pulposus tissues were collected during surgery, suspended in Dulbecco's Modified Eagle Medium/ Nutrient Mixture F-12 (DMEM/F12) in a 1:1 v/v mixture supplemented with antibiotics. The tissues were kept on ice until dissection, at which time they were rinsed 2–3 times in sterile Dulbecco's Phosphate Buffer Saline (DPBS) to remove any blood. In a laminar flow hood, the nucleus tissues were isolated and diced into small (2 mm) cubes, and then placed in a Tissue Culture Medium (hereinafter referred to as "TCM") comprising DMEM/F-12 culture media supplemented with 10% heat inactivated fetal bovine serum, 0.25% penicillin, 0.4% streptomycin, 0.001% amphotericin B, and 50 µg/ml ascorbic acid. Only tissues clear of blood and other anomalous elements were used. Placed on a shaker at 37° C., the tissues were digested with 0.01% hyaluronidase (Calbiochem) in TCM for 2 hours, 0.01% protease (Sigma) in TCM for 1 hour, and 0.1% collagenase Type II (Sigma) in TCM overnight to obtain a suspension of human intervertebral disc nucleus pulposus cells.

The foregoing procedure was also applied to sheep and baboon intervertebral disc nucleus pulposus tissues to obtain suspensions of sheep and baboon intervertebral disc nucleus pulposus cells, respectively.

EXAMPLE 9

Primary Culture and Expansion of Human, Sheep, and Baboon Intervertebral Disc Nucleus Pulposus Cells Human intervertebral disc nucleus pulposus cells from EXAMPLE 8 were expanded by culturing in TCM at 37° C. in 5% $CO_2$ atmosphere and 95% relative humidity. The TCM was changed every 2–3 days and the cells were passaged with trypsin to another container, when 80–90% confluent, for continued expansion.

The foregoing procedure was also applied to sheep and baboon intervertebral disc nucleus pulposus tissues to obtain an expanded supply of sheep and baboon intervertebral disc nucleus pulposus cells.

EXAMPLE 10

Alcian Blue Assay of Disc Cell Matrix Production in Human, Sheep, and Baboon Intervertebral Disc Nucleus Pulposus Cells Human intervertebral disc cells from EXAMPLE 9 were seeded and grown in 24 well plates in TCM in the presence or absence of exogenous growth factors. At various time points, TCM was aspirated out from the wells and the wells washed 3 times with PBS. The cells were then fixed with 4% paraformaldehyde (pH 7.4) for 10 min. The fixed cells were washed 2 times with PBS and then stained overnight with 0.5% Alcian blue in 0.1N hydrochloric acid (pH 1.5). After overnight staining, excess stain was rinsed out with 3 rinses of PBS. The remaining Alcian blue stain (bound to proteoglycans) was dissolved overnight into 6M guanidine hydrochloride and the absorbance at 630 nm was measured using a spectrophotometer, providing an indication of the induction of matrix production by exogenous growth factors in human nucleus pulposus cells.

The foregoing procedure was also applied to sheep and baboon intervertebral nucleus pulposus cells from EXAMPLE 9 to obtain an indication of the induction of matrix production by exogenous growth factors in sheep and baboon nucleus pulposus cells.

EXAMPLE 11

Enzyme Linked Immunosorbent Assay (ELISA) on Ovine Intervertebral Disc Nucleus Pulposus Cells To detect specific antigenic epitopes in the synthesized matrix, sheep intervertebral nucleus pulposus cells from EXAMPLE 9, seeded and grown in monolayer, were fixed in 2% glutaraldehyde for 1 hour at room temperature. The fixed cells were washed 3 times with TBS for 5 min. each. To block non-specific antibody binding, the cells were incubated in a solution of Tris buffered saline (TBS) containing 1 mM ethylene-diamine-tetraacetic acid (EDTA), 0.05% Tween-20, and 0.25% bovine serum albumin for 1 hour. The blocking step was followed by 3 washes with TBS for 5 min. each. The cells were incubated with the primary antibody at room temperature for 2.5 hours, and the excess primary antibody was removed by 3 washes with TBS for 5 min. each. A second incubation with blocking buffer was performed for 10 min., followed by 3 washes with TBS. The cells were then incubated with the secondary antibody, which was conjugated with alkaline phosphatase enzyme, for 3 hours at room temperature. The unbound secondary antibodies were removed by 3 washes of TBS for 5 min each. The bound primary and secondary antibodies were detected by addition of an enzyme-specific substrate which produced a colored reaction. The calorimetric measurement was performed using a spectrophotometer, providing a quantitative measure of the presence of the bound antibodies.

EXAMPLE 12

Effect of Exogenous Growth Factors on Proteoglycan Synthesis in Ovine Intervertebral Disc Nucleus Pulposus Cells Transforming growth factor-$\beta 1$ (TGF$\beta 1$) and a mixture of bone-derived protein growth factors (BP) produced according to U.S. Pat. Nos. 5,290,763, 5,371,191 and 5,563,124, were tested for their effects on stimulation of proteoglycan synthesis in ovine nucleus pulposus cells. Sheep intervertebral disc nucleus cells were collected and cultured as described in EXAMPLES 8 and 9. Sheep cells were seeded in micromass (200,000) into the wells of a 24 well plate. Growth factor dilutions were prepared in TCM supplemented with 0.5% heat-inactivated fetal bovine serum. TGF$\beta 1$ and BP were both tested at 10 ng/ml; BP was also tested at a concentration of 10 $\mu$g/ml. Control wells without growth factors contained TCM supplemented with 0.5% and 10% heat-inactivated fetal bovine serum. The cells were incubated in continuous exposure to the various growth factors for 7 and 10 days. At these time points, the cells were fixed and the amount of proteoglycan synthesis was measured by the Alcian blue assay as described in EXAMPLE 10.

At both 7 and 10 day time points, proteoglycan synthesis was significantly greater in the 10% fetal bovine serum control cultures than in the 0.5% fetal bovine serum control cultures. At the 7 day time point, BP at the higher 10 $\mu$g/ml concentration produced a significant (93%) increase in proteoglycan synthesis above the level in 10% serum control culture and a greater (197%) increase above the 0.5% serum control. Slight increases in proteoglycan synthesis above the 0.5% serum control were observed in the 10 ng/ml TGF$\beta 1$ and BP cultures, but these increases were not significant.

At the 10 day time point (FIG. 8), 10 $\mu$g/ml BP produced a significant increase (132%) in proteoglycan synthesis over the 10% serum control, while 10 ng/ml TGF$\beta 1$ produced a significant increase (52%) above the 0.5% serum control. At 10 ng/ml, BP exhibited a modest 20% increase in proteoglycan synthesis over the 0.5% serum control, while at the 10 $\mu$g/ml concentration, BP produced an 890% increase above the 0.5% serum control.

EXAMPLE 13

Effect of Exogenous Growth Factors on Type II Collagen and Chondroitin-6-Sulfate Produced by Ovine Intervertebral Disc Nucleus Pulposus Cells TGF$\beta 1$ and BP were tested for their effects on stimulation of Type II collagen and chondroitin-6-sulfate synthesis in sheep intervertebral disc nucleus pulposus cells. The cells were obtained and cultured as described in EXAMPLES 8 and 9 and seeded into tissue culture dishes. The TGF$\beta 1$ and BP growth factors were prepared in TCM supplemented with 0.5% heat inactivated fetal bovine serum. TGF$\beta 1$ was tested at a concentration of 10 ng/ml; BP was tested at a concentration of 10 $\mu$g/ml. Control cultures were incubated in TCM supplemented with 0.5% serum alone.

After incubation with growth factors for 7 days, cell cultures were fixed in 2% glutaraldehyde and the quantity of Type II collagen and chondroitin-6-sulfate produced in the cell cultures was detected by ELISA according to the procedure described in EXAMPLE 11. The primary antibodies used were mouse anti-human Type II collagen and mouse anti-human chondroitin-6-sulfate.

Figures 15A, 15B:
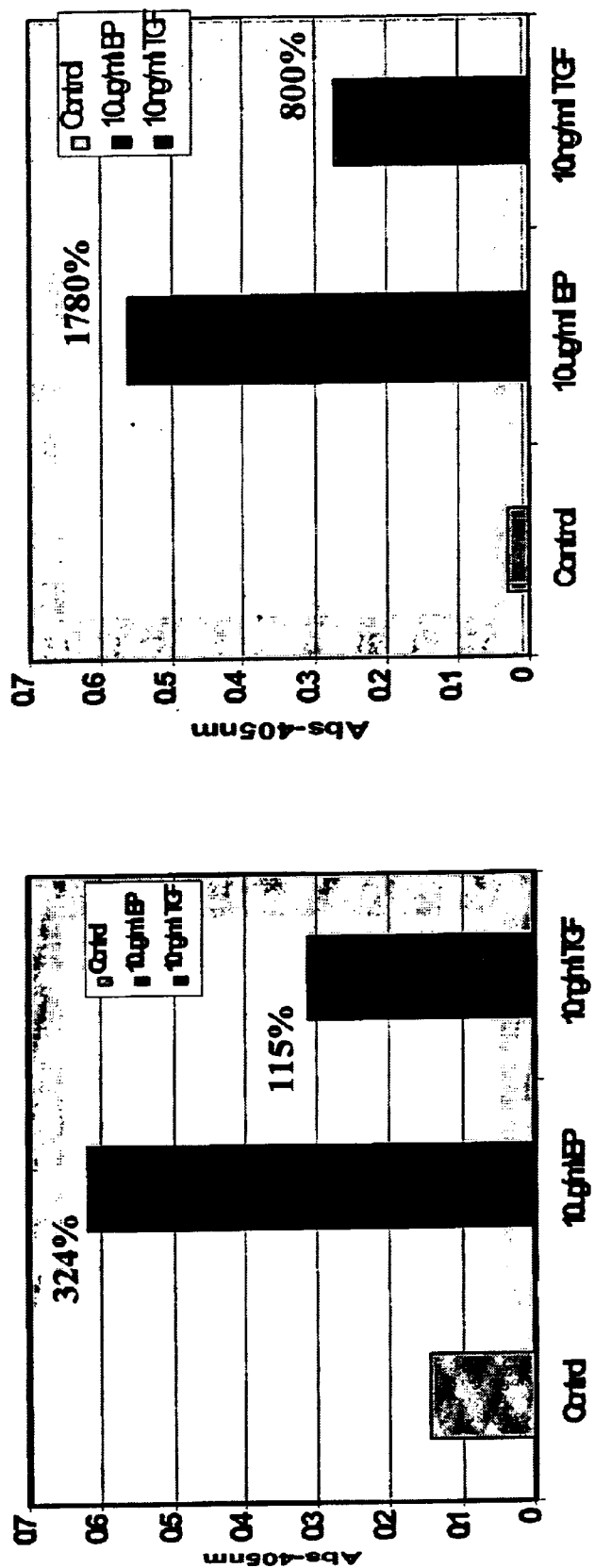
FIGS. 15A and 15B are graphs representing the results of an ELISA performed to measure the synthesis of Type II collagen (FIG. 15A) and Chondroitin-6-sulfate (FIG. 15B) under growth factor stimulation.

At 7 days, cell cultures incubated with 10 $\mu$g/ml BP produced 324% more Type II collagen and 1780% more chondroitin-6-sulfate than control cultures. 10 ng/ml TGF$\beta 1$ increased production of Type II collagen by 115% and chondroitin-6 sulfate by 800% over controls. See FIGS. 15A and 15B.

EXAMPLE 14

Effect of Exogenous Growth Factors on Proteoglycan Synthesis in Human Intervertebral Disc Nucleus Pulposus Cells TGF$\beta 1$ and BP were tested for their effects on stimulation of proteoglycan synthesis in human nucleus cells. Human intervertebral disc nucleus pulposus cells obtained from Disc L5-S1 of a 40yr old female patient were cultured as described in EXAMPLES 8 and 9 and seeded into 24 well plates. After the cells adhered to the well surface, multiple dilutions of different growth factors were added. The concentrations of growth factors tested were 10 ng/ml TGFβ1, and 10 and 20 µg/ml of BP. The dilutions were prepared in TCM. The cells were fixed after 5 and 8 days of continuous exposure to growth factors and proteoglycans synthesized were detected by the Alcian blue assay as described in EXAMPLE 10.

At 5 days only BP produced a significant increase in Alcian blue staining over controls. At 10 µg/ml BP there was a 34% increase over the control while at 20µg/ml there was a 23% increase over the control. The difference between the averages of 10 and 20 µg/ml BP was not significant.

Figure 16A:
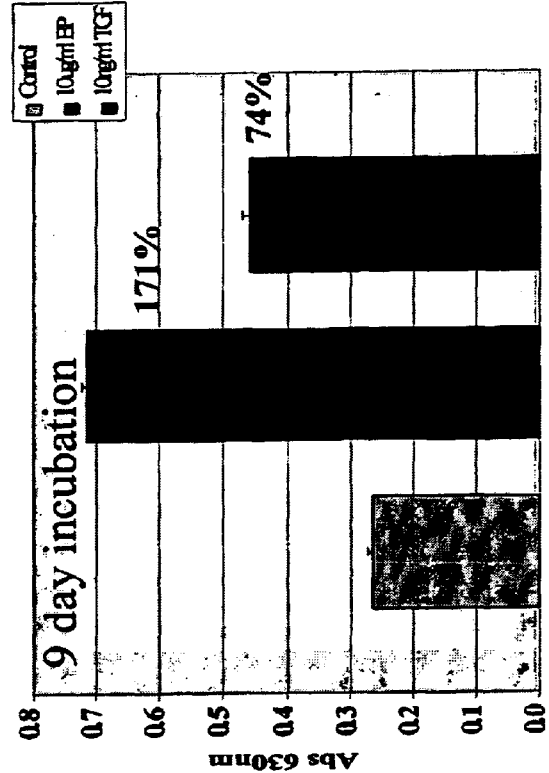
FIG. 16a is a graph indicating the results of an Alcian blue assay for proteoglycan synthesis in human intervertebral disc cells stimulated by growth factor.

At 8 days (FIG. 16a), both growth factors exhibited a significant increase in Alcian blue staining over the control. TGFβ1 at 10 ng/ml had a 42% increase over the control. BP had a 60% increase at 10 µg/ml and 66% increase at 20 µg/ml over the control.

EXAMPLE 15

Effect of Exogenous Growth Factors on Proteoglycan Synthesis in Human Intervertebral Disc Nucleus Pulposus Cells A second experiment to test the effects of TGFβ1 and BP on proteoglycan synthesis was performed on a different human patient from that described in EXAMPLE 14. Human intervertebral disc cells obtained from another 40-year-old female patient were cultured as described in EXAMPLES 8 and 9 and seeded into 24 well plates. Growth factors were added after the cells were allowed to adhere overnight. TGFβ1 was tested at a concentration of 10 ng/ml; BP was tested at 10 µg/ml. After 6 and 9 days the cells were fixed and the amount of proteoglycans synthesized was measured by the Alcian blue assay as described in EXAMPLE 10.

Figure 16B:
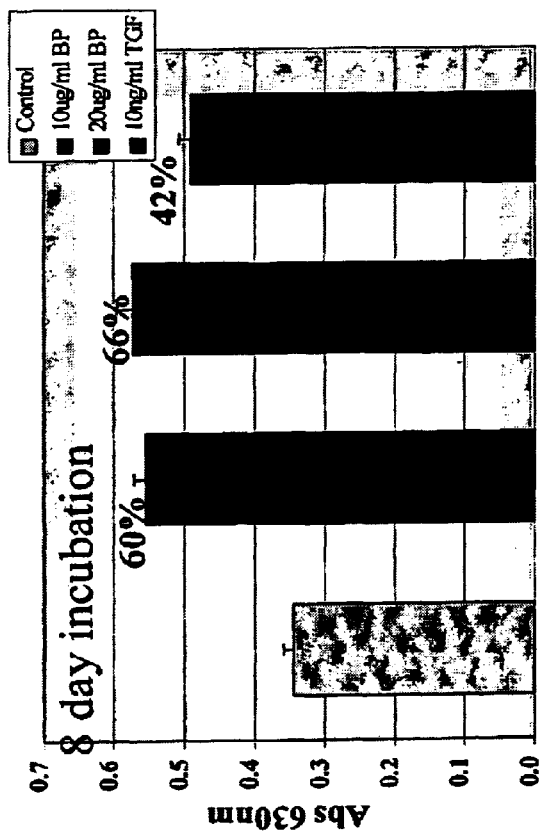
FIG. 16b is a graph indicating the results of an Alcian blue assay for proteoglycan synthesis in another human intervertebral disc cells stimulated by growth factor.

At 6 days cells stimulated with 10 ng/ml TGFβ1 produced 54% more proteoglycans than control, and 10 µg/ml BP increased production by 104% over the control. At 9 days (FIG. 16b), 10 ng/ml TGFβ1 increased production by 74% over controls, and 10 µg/ml BP increased production by 171% over the control.

EXAMPLE 16

Effect of Exogenous Growth Factors on Proteoglycan Synthesis in Baboon Intervertebral Disc Nucleus Pulposus Cells TGFβ1 and BP were tested for their effects on stimulation of proteoglycan synthesis in baboon nucleus cells. Baboon intervertebral disc nucleus pulposus cells were obtained from a 7 year old male baboon, cultured as described in EXAMPLES 8 and 9, and seeded into a 24 well plate. The cells were allowed to adhere to the well surface before the addition of growth factors. The concentrations of growth factors tested were 10 µg/ml BP and 10 ng/ml TGFβ1. The dilutions were prepared in TCM. The cells were fixed after 4 and 8 days of continuous exposure to growth factors, and proteoglycan synthesis was detected by the Alcian blue assay as described in EXAMPLE 10.

At 4 days there was no significant increase in proteoglycan synthesis between the different growth factors and the control. At 8 days (FIG. 17), TGFβ1 and BP significantly increased proteoglycan synthesis over the control, but the increase was only marginal. In particular, TGFβ1 produced a 21% increase over the control while BP produced a 22% increase over the control.

EXAMPLE 17

Staining of Seeded Matrix Material with Phalloidin

Cross-linked matrix seeded with living cells was stained with phalloidin to indicate the growth and proliferation of living cells into the matrix. The media was rinsed from the matrix with 3 PBS washes of 5 min each. The matrix was fixed for 1 hour at room temperature with 4% parafornaldehyde. The 4% paraformaldehyde was washed off with 3 PBS rinses. The matrix was treated with 0.1% Triton-X 100 for 3 min and then washed with 3 PBS rinses. The matrix was then stained with phalloidin-conjugated rhodamine, made up in PBS, for 45 min. Excess phalloidin was washed off with PBS. The matrix was mounted on slides and viewed under fluorescence with filter of X range 530–550 nm.

EXAMPLE 18

Growth and Proliferation of Sheep Intervertebral Disc Nucleus Pulposus Cells into Non-Homogenized Matrix with BP Growth Factor Ingrowth and proliferation of growth factor stimulated sheep intervertebral disc nucleus pulposus cells into the matrix of the present invention was investigated. Cross-linked matrix material obtained prior to the lyophilization step of Example 1 was cut into square pieces 75 mm on each side and sterilized in 70% ethanol for 3 hours. Remaining steps in the protocol were performed under aseptic conditions.

Ethanol was removed from the matrix with two 1-hour washes in sterile PBS, followed by a one hour wash in TCM. The matrix pieces were then suspended overnight in TCM having BP concentrations of 20 ng/ml and 20 µg/ml. The control was cross-linked matrix suspended in 20 µg/ml BSA (bovine serum albumin). Each matrix piece was then placed in a well of a 24 well plate and seeded with TCM containing sheep intervertebral disc nucleus cells at 40,000 cells/ml. The cells were allowed to grow into the matrix and the TCM was changed every 2–3 days. Sample matrix pieces were fixed at 3, 6 and 9 days and stained with phalloidin as described in EXAMPLE 17. The process is illustrated in FIG. 7.

Infiltration of sheep nucleus pulposus cells into the matrix was observed at all of the 3, 6 and 9 day timepoints, indicating that the matrix is biocompatible. The number of cells observed per field was higher at 6 and 9 days, indicating that the cells were proliferating into the matrix. More cells were observed in matrix pieces that had been suspended in TCM containing BP than in controls having no growth factor. BP at 20 µg/ml produced the greatest infiltration and proliferation of cells into the matrix.

EXAMPLE 19

Growth and Proliferation of Sheep Intervertebral Disc Nucleus Pulposus Cells into Homogenized Matrix with BP Growth Factor A further investigation of the ingrowth and proliferation of growth factor stimulated sheep intervertebral disc nucleus pulposus cells into the matrix of the present invention was made using homogenized matrix, as opposed to the nonhomogenized matrix in EXAMPLE 18. Cross-linked matrix material obtained prior to the lyophilization step of Example 1 was homogenized using a tissue homogenizer, and sterilized in 70% ethanol for 3 hours. All subsequent steps in the protocol were under aseptic conditions.

The homogenized matrix was centrifuged at 3200 rpm for 10 min and the supernatant was discarded. The pelleted matrix was rinsed with two 1-hour PBS washes, followed by a 1-hour TCM wash. Between each wash the matrix was centrifuged, and the supernatant was discarded. The pelleted matrix was then suspended overnight in TCM having BP concentrations of 20 ng/ml and 20 µg/ml. The control was cross-linked matrix suspended in 20 µg/ml BSA The TCM/matrix mixture was then centrifuged and the supernatant was discarded. The matrix pellet was resuspended in TCM containing sheep intervertebral disc nucleus cells, obtained according to the procedure in EXAMPLES 8 and 9. The matrix/cell suspension was pipetted into wells of a 24 well plate. The TCM was changed every 2–3 days. The homogenized matrix seeded with cells was fixed at 4 days and stained with phalloidin as described in EXAMPLE 17. The process is illustrated in FIG. 7.

After 4 days, the layer of cross-linked matrix soaked in 20 µg/ml BP and seeded with cells had contracted to form a rounded clump of compact tissue. This tissue was comprised of both the original cross-linked matrix and the newly synthesized matrix produced by the infiltrated cells. There were very few cells adherent to the well surface, indicating that most cells had infiltrated the matrix. This conclusion was reinforced by the dense infiltration of cells into the matrix as visualized by phalloidin staining. The cells had assumed a rounded morphology which is characteristic of nucleus chondrocytic cells, indicating reversion to their original morphology. Cells had also grown into matrix soaked in 20 ng/ml BP by 4 days, but cell ingrowth was not as dense as in the matrix soaked in 20 µg/ml BP.

The control matrix suspended in BSA also had cells infiltrating into it, but it was the least populated among the different dilutions.

EXAMPLE 20

In Vivo Evaluation of Cross-linked Matrix and Bone Protein (BP) Growth Factor for Nucleus Pulposus Regeneration in an Ovine Lumbar Spine Model Pilot studies were conducted to evaluate preparative and surgical methods for the implantation of the cross-linked matrix containing BP growth factors into the intervertebral disc space of the sheep lumbar spine, to evaluate whether implantation of the matrix with growth factors arrests degeneration and/or stimulates regeneration of nucleus pulposus in a sheep disc degeneration model over a period of six months, and to assess the antibody- and cell-mediated immune response in sheep to the matrix/BP combination.
Study #1

One-half gram (0.5 g) of cross-linked, lyophilized and pulverized matrix prepared as described in EXAMPLE 1 was rehydrated and sterilized by two 4 hour rinses in 70% isopropanol. The matrix was centrifuged and pelleted, and then rinsed in sterile PBS three times for 2 hours each to remove the isopropanol. The rehydrated matrix was again centrifuged and pelleted.

Bone Protein (BP) prepared according to U.S. Pat. Nos. 5,290,763 and 5,371,191 was obtained from Sulzer Biologics, Inc. (Wheat Ridge, Colo.) in a lyophilized form. Two milligrams (2 mg) of BP was suspended in 100 µl dilute 0.01M hydrochloric acid to produce a 20 mg/ml BP stock solution. The BP stock solution was diluted to 100 µg/ml in sheep serum and the BP/serum suspension was sterile-filtered through a 0.2 micron filter. Next, 1.0 ml of the sterile BP/serum suspension was added to 1.0 ml of the rehydrated matrix described above to obtain a final concentration of 50 µg BP per ml of cross-linked, rehydrated matrix/serum suspension. At the time of surgery, one aliquot (0.5 ml) of the rehydrated matrix/BP/serum suspension was loaded into a sterile 3 ml pressure control syringe with an 18 or 20 gauge needle for injection.

Three sheep were anesthetized and the dorsolateral lumbar area prepared for surgery. Blood was drawn from each sheep pre-operatively, centrifuged, and serum collected for immunology studies. A ventrolateral, retroperitoneal approach was made through the oblique abdominal muscles to the plane ventral to the transverse processes of the lumbar spine. The annuli fibrosi of intervertebral discs L3-4, L4-5, and L5-6 were located, soft tissues retracted, and a discrete 5 mm deep by 5 mm long incision was made into both L3-4 and L5-6 discs. The intervening, middle L4-5 disc remained intact to serve as an intra-operative control. Following annulus stab procedures, the musculature and subcutaneous tissues were closed with absorbable suture. After postoperative recovery, sheep were allowed free range in the pasture.

Two months after the annulus stab surgical procedures, the sheep were operated upon a second time. After anesthesia and preparation for surgery, the three operated lumbar spine levels were again exposed. Two hundred microliters (200 µl) of the prepared test material (i.e., rehydrated matrix/BP/serum suspension) was injected into the intradiscal space of one (L5-6) of the experimentally-damaged discs. The second operated disc (L3-4) served as a sham-treated degenerative disc; the syringe needle punctured the annulus but no material was injected. After disc treatments, the musculature and subcutaneous tissues were closed with absorbable suture. Following postoperative recovery, sheep were allowed free range of movement. The study design is diagrammatically represented in FIG. 10.

The sheep were sacrificed at 2, 4, and 6 months after the second surgery. The radiograph from the 2 month sheep showed a degenerative appearance of the untreated disc but a normal appearance in the control and treated discs (FIG. 11). Histological analysis of the 2 month sheep as illustrated in FIG. 12 confirmed extensive degeneration within the sham-treated, stab-induced degenerative disc. In both the control disc and the matrix/BP-treated disc, a normal sized gelatinous nucleus and regular, compact annulus were observed. In the 4 month and 6 month sheep, no obvious changes were seen in the radiograph of the three discs. A radiograph of the 4 month sheep is shown in FIG. 13. However, on gross dissection in the 4 month sheep, the sham-treated disc exhibited obvious gross degeneration while the control and treated discs were normal in appearance (FIG. 14). In the 6 month sheep, there were no gross differences between the sham-treated, control, and treated discs.

Although there was some variation in the rate of degeneration using the annulus stab technique (i.e., the absence of clear degeneration in the 6 month sheep), these results suggest that the cross-linked matrix/BP treatment may protect against or impede the progress of stab-induced degeneration in sheep intervertebral discs.
Study #2

For the second study, matrix material was rehydrated and combined with BP and serum to produce a matrix/BP/serum suspension as described in Study #1.

Twelve sheep were anesthetized and the dorsolateral lumbar area prepared for surgery. Blood was drawn from each sheep pre-operatively, centrifuged, and serum collected for immunology studies. A ventrolateral, retroperitoneal approach was made through the oblique abdominal muscles to the plane ventral to the transverse processes of the lumbar spine. The annuli fibrosi of intervertebral discs L1-2, L2-3, L3-4, L4-5, and L5-6 were located, soft tissues retracted, and a small diameter hole punched through the annulus using a syringe needle in 4 of the 5 discs. A small curette was then placed through the hole into the intradiscal space to remove a discrete portion of nucleus pulposus from each of the four discs in each sheep. In 2 of the 4 damaged discs, 0.5 ml of the matrix/BP/serum suspension was injected into the intradiscal spaces and the needle punctures were sealed off with ligament sutured over them. The immediate injection of this suspension was considered an "acute" treatment protocol. The 2 other damaged discs were left untreated at that time but were sealed off with ligament sutured over the needle punctures. The intervening, middle L3-4 disc remained intact in all sheep spines to serve as an intraoperative control. Following these procedures, the musculature and subcutaneous tissues were closed with absorbable suture. After postoperative recovery, sheep were allowed free range.

Six weeks after the first surgery to remove portions of the nucleus pulposus, the sheep were operated upon a second time. After anesthesia and preparation for surgery, the five operated lumbar spine levels were again exposed. In one of the two remaining nontreated discs which had been damaged six weeks before, 0.5 milliliters of the prepared test material (i.e., rehydrated matrix/BP/serum suspension) was injected into the intradiscal space of the disc. The injection of this suspension six weeks later into a damaged disc was considered a "delayed" treatment protocol. The second nontreated damaged disc served as a sham-treated degenerative disc; the syringe needle punctured the annulus but no material was injected. The treatment method used in each of the four experimentally-damaged discs was randomized for location within the spines. That is, except for the intact control disc (L3-4), the locations of an "acute" treatment disc, a "delayed" treatment disc, or a nontreated, damaged disc, were randomly assigned to one of the four different lumbar disc levels. After disc treatments, the musculature and subcutaneous tissues were closed with absorbable suture. Following postoperative recovery, sheep were allowed free range.

The sheep were sacrificed at 2, 4, and 6 months after matrix/BP/serum injections and the spines were fixed for histology in formalin. Cross-sections were taken from plastic-embedded discs, stained with H & E and Saffranin-O, and evaluated for chondrocyte proliferation (cloning), proteoglycan staining intensity, level of fibrosis, and level of ossification. An evaluation of the "acute" treatment discs, "delayed" treatment discs, sham-treated, and control discs was made in a blinded fashion and ranked +1, +2, or +3 (low, medium, or high) for each parameter listed above. Semiquantitative evaluation of the histological results was compared in 2 month, 4 month, and 6 month sheep for both the "acute" and "delayed" (6 week) treatments.

The results demonstrated overall that injected matrix+BP stimulated chondrocyte cloning and accumulation of Saffranin-O staining of glycosaminoglycans in the nucleus matrix of damaged discs. In particular, the extent of regenerative repair was much greater in both "acute" treatment discs and "delayed" treatment discs, compared to that observed in non-treated, damaged discs. This greater level of repair in matrix/BP-treated discs was statistically significant at the 0.01 level of confidence. There was also less fibrosis and ossification seen in the acute and delayed treatment discs compared to the non-treated discs.

A significant difference was also noted between the "delayed" treatment discs and the "acute" treatment discs in the level of proteoglycan staining. For example, Saffranin-O staining as an index to proteoglycan synthesis and content in the nucleus matrix was greater in the "delayed" matrix/BP-treatment discs than in the "acute" matrix/BP-treatment discs. Additional benefits apparent in the histological evaluation, which were associated with "delayed" treatment with matrix/BP, were an overall lack of bony transformation (ossification) or fibrous tissue accumulation (fibrosis) within the treated discs compared to the non-treated, damaged discs. In general, the results in Study #2 support and elaborate earlier indications from Study #1 that treatment of damaged discs with the cross-linked matrix/BP may protect against or impede the progress of degeneration in experimentally-damaged sheep intervertebral discs.

Example 21

Characterization of BP

Figure 18:
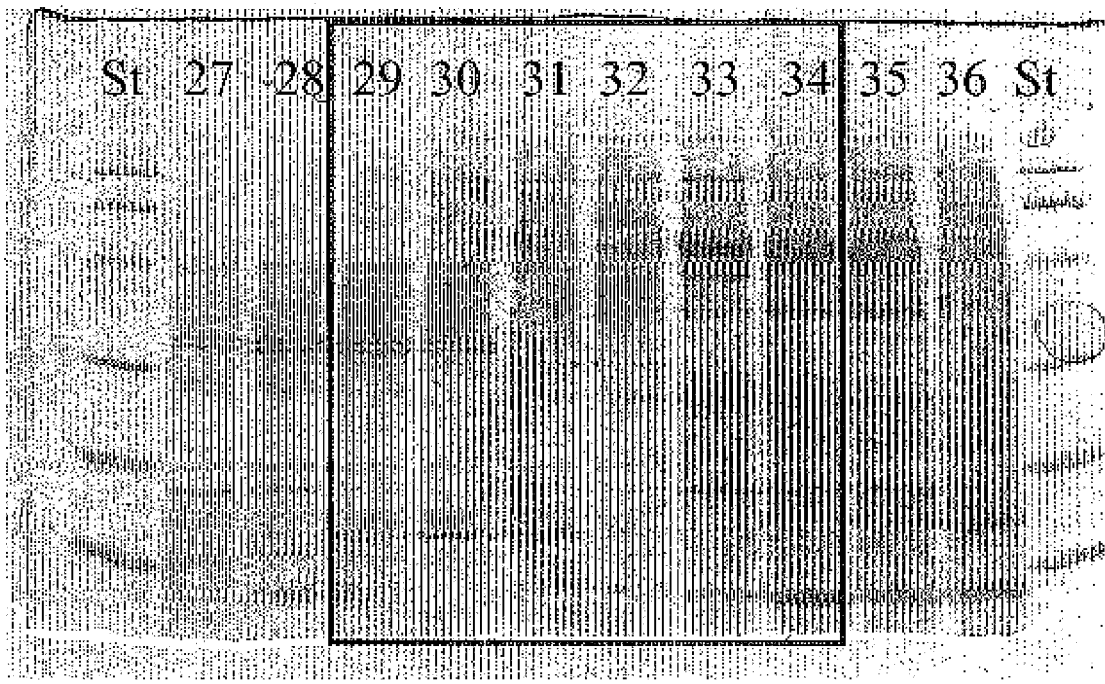
FIG. 18 is an SDS-PAGE gel of HPLC fractions 27-16 from a sample of BP.
Figure 19:
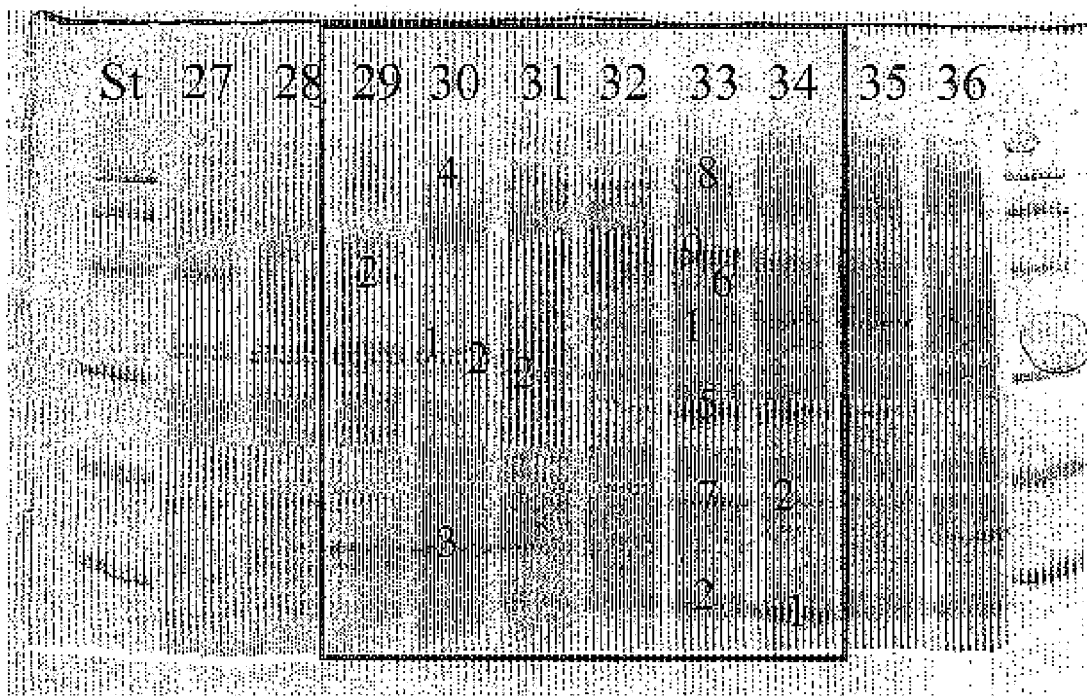
FIG. 19 is an SDS-PAGE gel of HPLC fractions 27-16 with identified bands indicated according to the legend of FIG. 20.

Specific growth factors present in the mixture of growth factors produced according to U.S. Pat. Nos. 5,290,763, 5,371,191, and 5,563,124 (i.e., BP) have been identified. BP has been partially characterized as follows: HPLC fractions have been denatured, reduced with DTT (dithiothreitol), and separated by sodium dodecyl sulfate polyacrylamide gel electrophoresis (SDS-PAGE). One minute high performance liquid chromatography (HPLC) fractions taken at from 27 to 36 minutes are shown in FIG. 18. Size standards (ST) of 14, 21, 31, 45, 68 and 97 kDa were obtained as Low Range size standards from BIORADM and are shown at either end of the Coomassie blue stained gel (FIGS. 18 and 19). In the usual protocol, HPLC fractions 29 through 34 are pooled to produce BP (see box in FIGS. 18 and 19), as shown in a similarly prepared SDS-PAGE gel in FIG. 33B.

An SDS-PAGE gel of BP was also analyzed by Western immunoblot with a series of antibodies, as listed in FIG. 30. Visualization of antibody reactivity was by horse radish peroxidase conjugated to a second antibody and using a chemiluminescent substrate. The reactivities are as indicated in FIG. 30.

Figure 21:
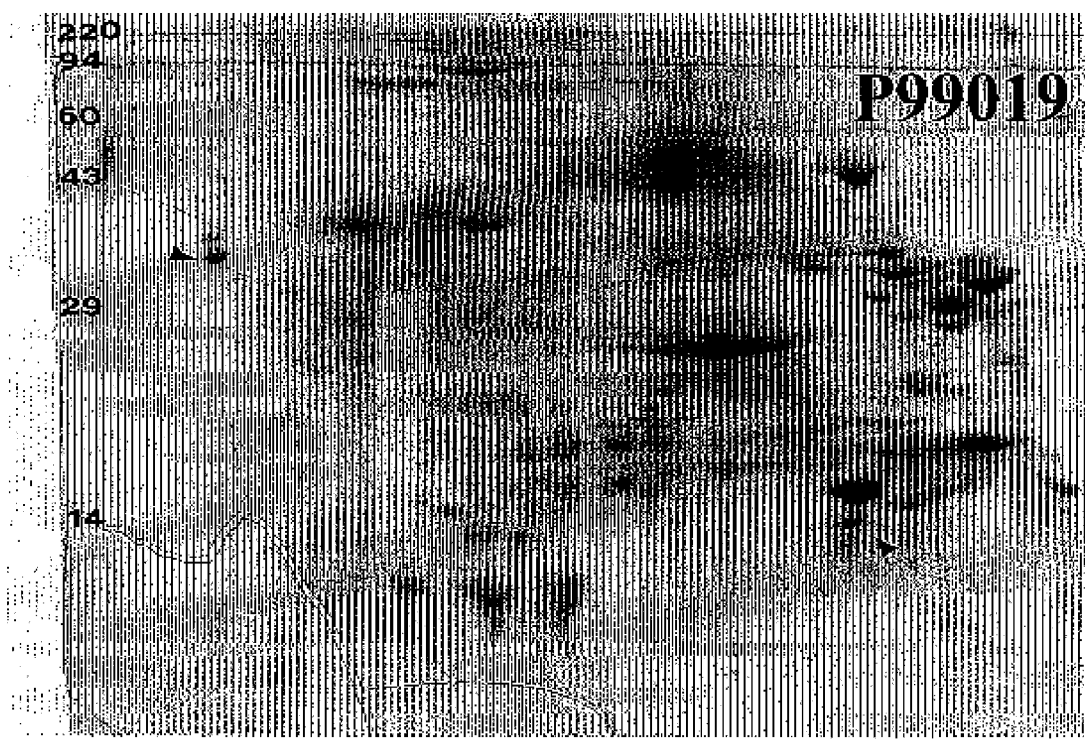
FIG. 21 is a 2-D (two-dimensional) SDS-PAGE gel with internal standards indicated by arrows.
Figure 22:
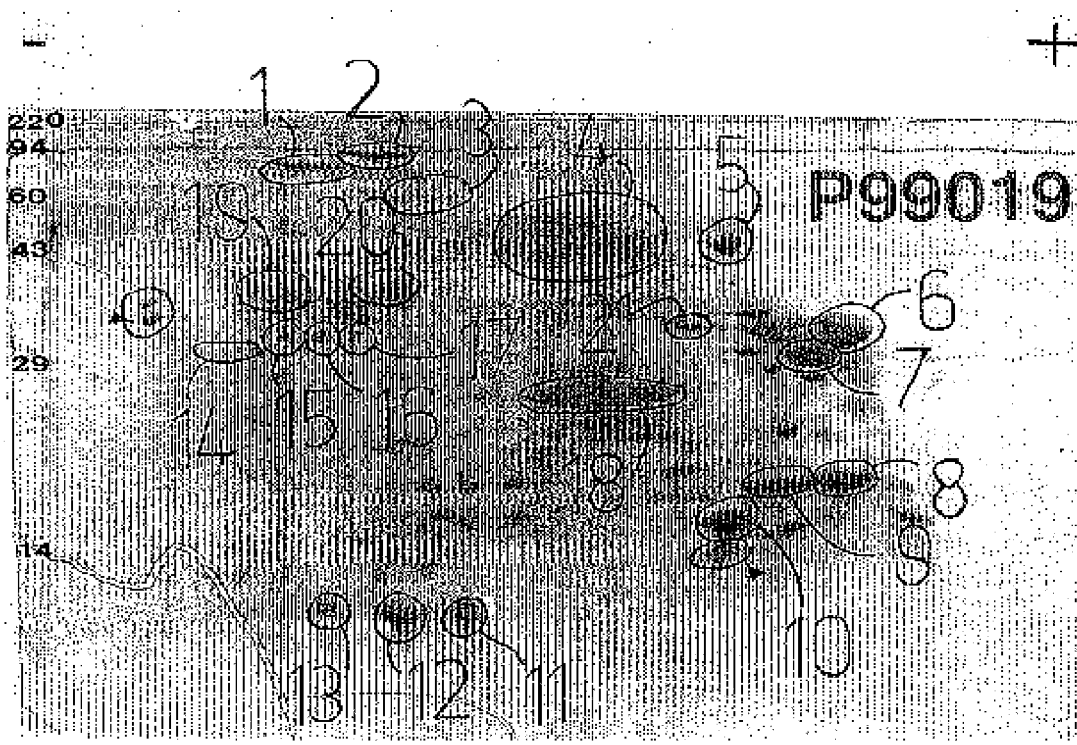
FIG. 22 is a 2-D SDS-PAGE gel with circled proteins (growth factors) identified as in legend.

The BP was further characterized by 2-D (two dimensional) gel electrophoresis, as shown in FIGS. 21 and 22. The proteins are separated in horizontal direction according to charge (pI) and in the vertical direction by size according to the method of O'Farrell et al. (*Cell*, 12:1133–1142, 1977). Internal standards, specifically tropomyosin (33 kDa, pI 5.2) and lysozyme (14.4 kDa, pI 10.5–11.0), are included and the 2-D gel was visualized by Coomassie blue staining. FIG. 21 shows the stained 2-D gel with size standards indicated on the left. Tropomyosin (left arrow) and lysozyme (right arrow) are also indicated.

The same gel is shown in FIG. 22 with several identified proteins indicated by numbered circles. The proteins were identified by mass spectrometry and amino acid sequencing of tryptic peptides, as described below. The identity of each of the labeled circles is provided in the legend of FIG. 22.

Figure 20:
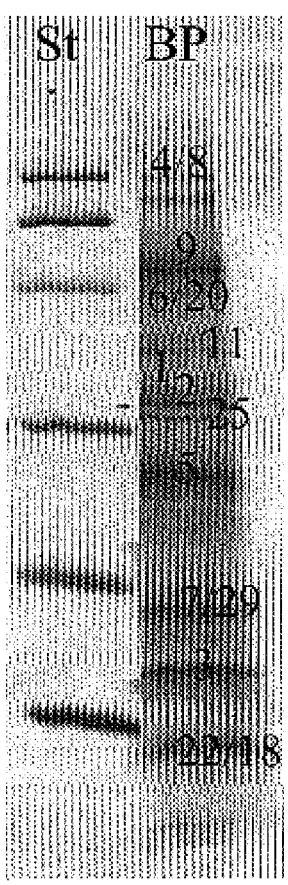
FIG. 20 is an SDS-PAGE gel of BP with identified bands indicated.

The various components of the BP were characterized by mass spectrometry and amino acid sequencing of tryptic fragments where there were sufficient levels of protein for analysis. The major bands in the 1-D (one dimensional) gels were excised, eluted, subjected to tryptic digestion, purified by HPLC and sequenced by methods known in the art. The major bands are identified by band number, as shown in FIGS. 19 and 20. The sequence data was compared against known sequences, and the fragments are identified as shown in FIG. 31. In some cases, the identification is tentative due to possible variation between the human and bovine sequences and/or possible post translational modifications, as discussed below.

The same tryptic protein fragments were analyzed by mass spectrometry and the mass spectrograms are shown in FIGS. 23A–230. The tabulated results are shown in the Table depicted in FIGS. 32A–32F, which provides identification information for each of the indicated bands, as identified in FIGS. 19 and 20. As above, assignment of band identity may be tentative based on species differences and post translational modifications.

Figure 33A:
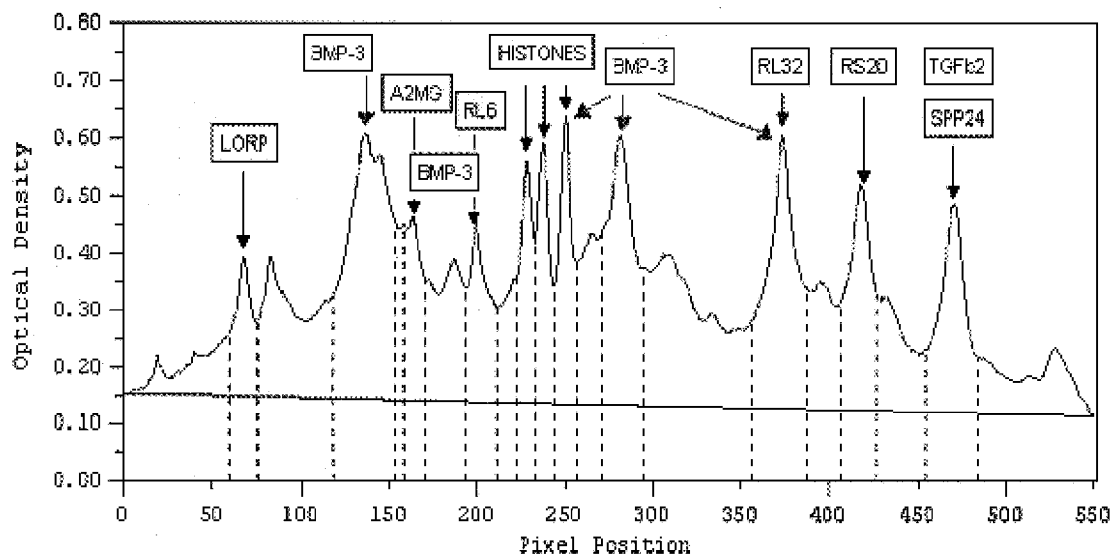
FIGS. 33A–33B are an SDS-gel of BP (FIG. 33B) and a scanning densitometer scan (FIG. 33A).
Figure 33B:
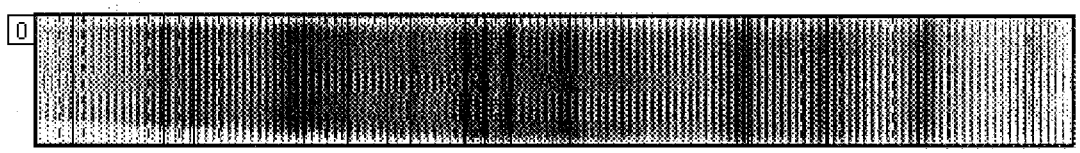

The identified components of BP were quantified as shown in FIGS. 33A and 33B. FIG. 33B is a stained SDS-PAGE gel of BP and FIG. 33A represents a scanning densitometer trace of the same gel. The identified proteins were labeled and quantified by measuring the area under the curve. These results are presented in FIG. 34 as a percentage of the total peak area.

As FIG. 34 indicates, there are 11 major bands in the BP SDS-PAGE gel representing about 60% of the protein in BP. Further, TGF-β1 was quantified using commercially pure TGF-β1 as a standard, and was determined to represent less than 1% of the BP protein. The identified proteins fall roughly into three categories: the ribosomal proteins, the histones, and growth factors, including active growth factors comprising members of the TGF-β superfamily of growth factors, which includes the bone morphogenic proteins (BMPs). It is believed that the ribosomal proteins and histone proteins may be removed from the BP without loss of activity, and the specific activity is expected to increase correspondingly.

Figure 24:
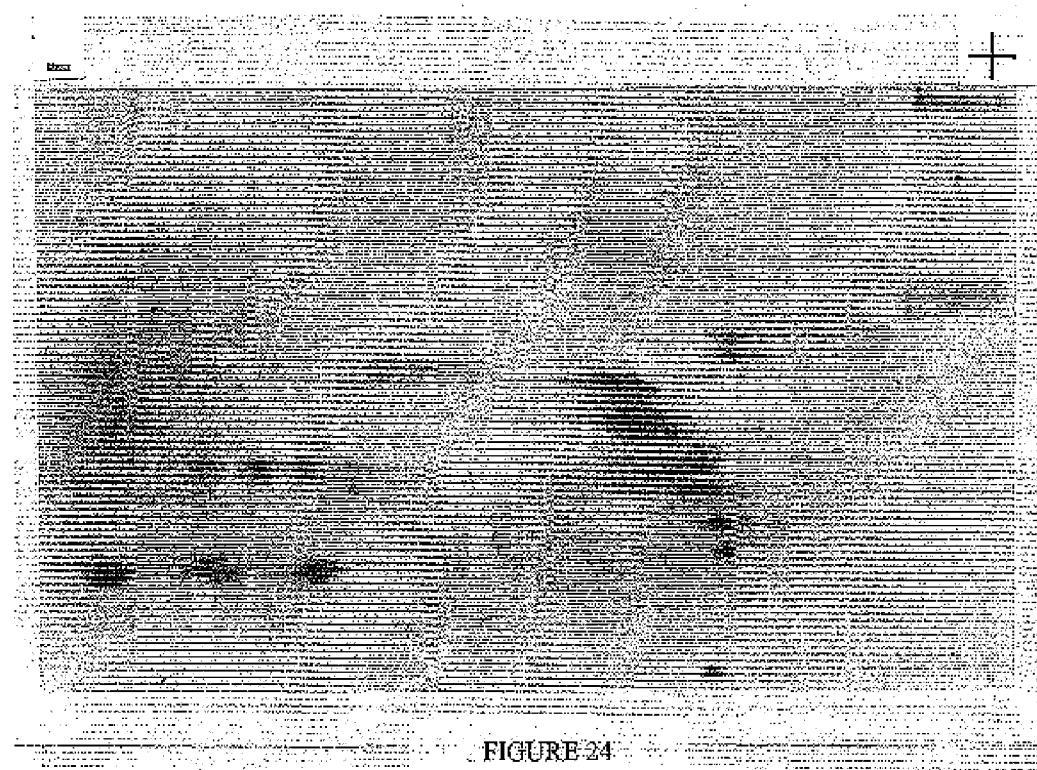
FIG. 24 is a 2-D gel Western blot with anti-phosphotyrosine antibody.
Figure 25A:
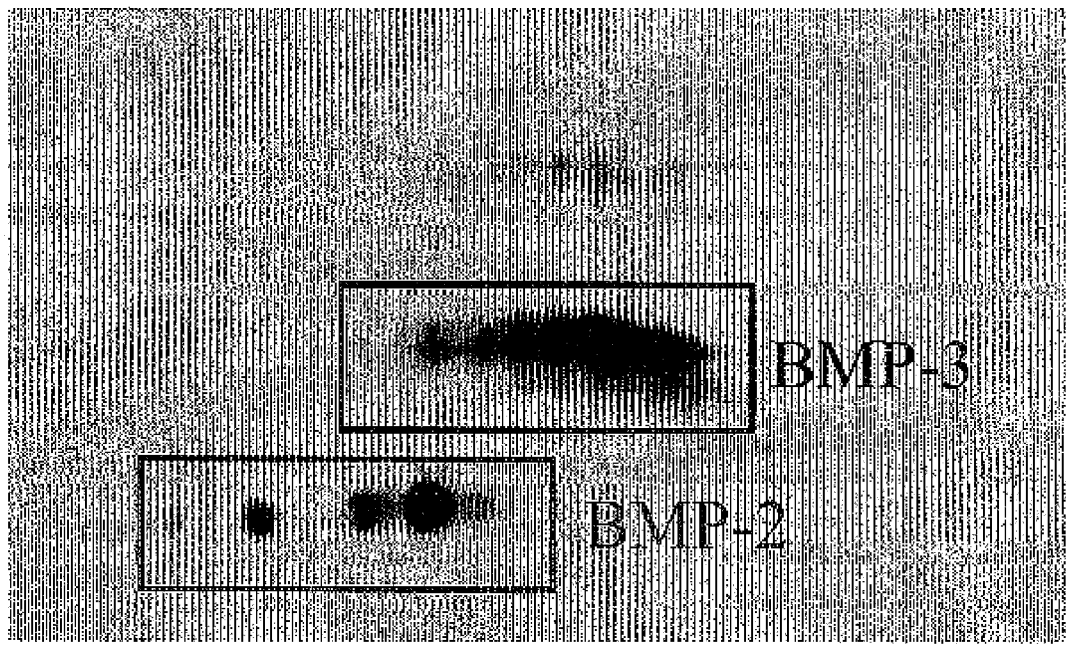
FIGS. 25A–25D are 2-D gel Western blots with antibodies for the indicated proteins. For FIG. 25A, the growth factors are BMP-3 and BMP-2; for FIG. 25B the growth factors are BMP-3 and BMP-7; for FIG. 25C the growth factors are BMP-7 and BMP-2; and for FIG. 25D the growth factors are BMP-3 and TGF-$\beta$1.
Figure 25B:
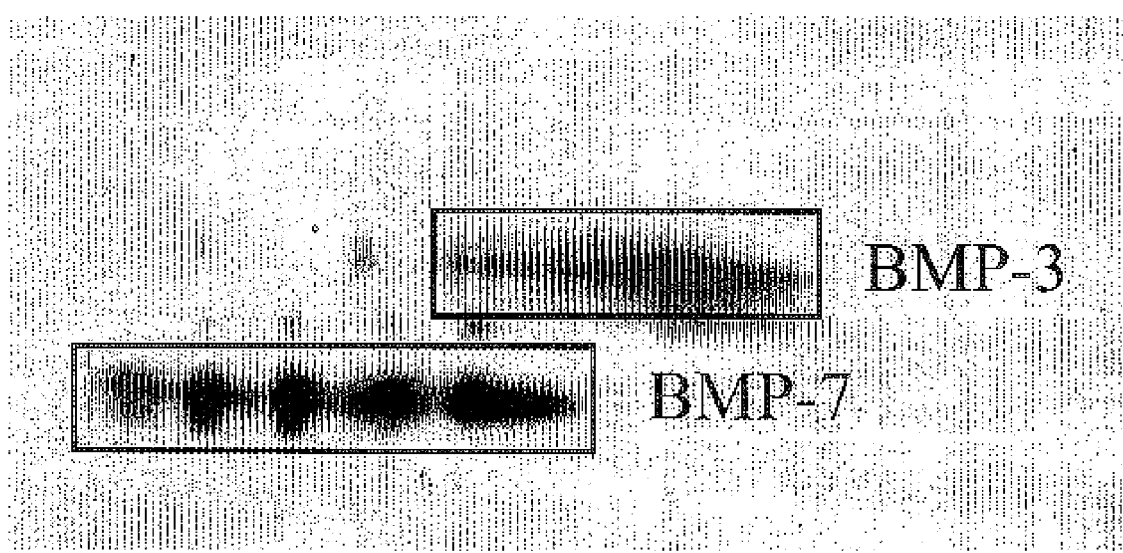
Figure 25C:
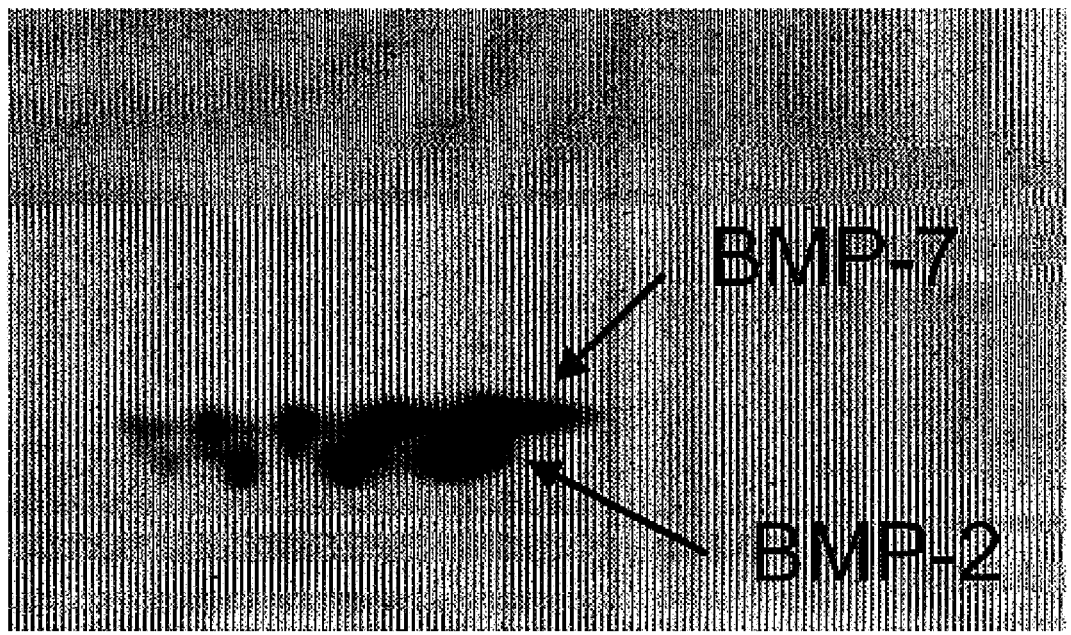
Figure 25D:
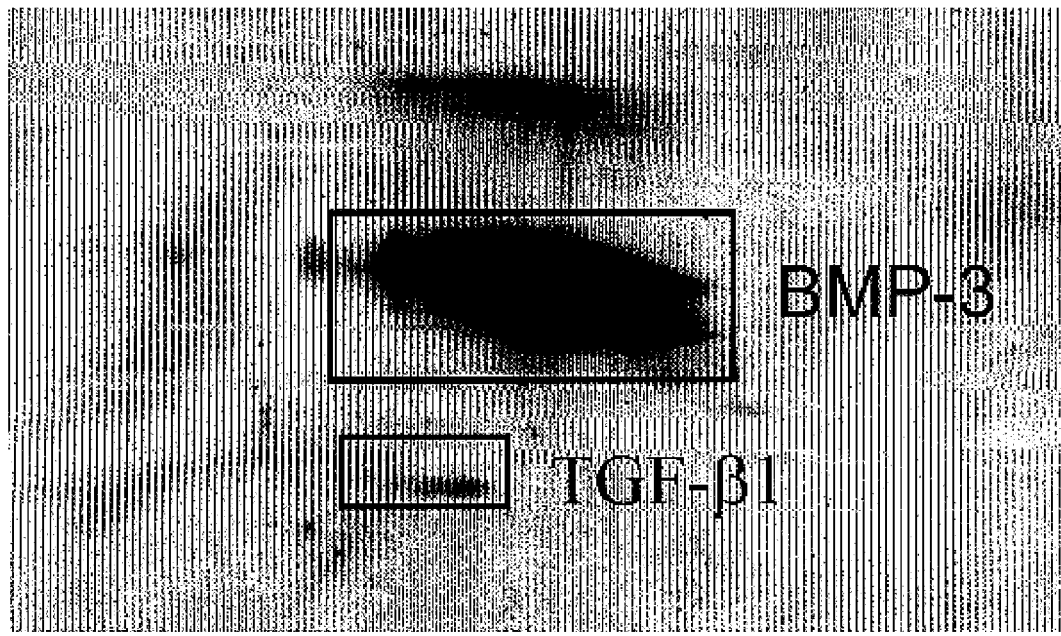

Because several of the proteins migrated at more than one size (e.g., BMP-3 migrating as 5 bands) investigations were undertaken to investigate the extent of post-translational modification of the BP components. Phosphorylation was measured by anti-phosphotyrosine immunoblot and by phosphatase studies. FIG. 24 shows a 2-D gel, electroblotted onto filter paper and probed with a phosphotyrosine mouse monoclonal antibody by SIGMA (#A-5964). Several proteins were thus shown to be phosphorylated at one or more tyrosine residues.

Similar 2-D electroblots were probed with BP component specific antibodies, as shown in FIGS. 25A–D. The filters were probed with BMP2, BMP-3 (FIG. 25A), BMP-3, BMP-7 (FIG. 25B), BMP-7, BMP-2 (FIG. 25C), and BMP-3 and TGF-β1 (FIG. 25 D). Each shows the characteristic, single-size band migrating at varying pI, as is typical of a protein existing in various phosphorylation states.

Native and phosphatase treated BP samples were also assayed for morphogenic activity by explant mass and ALP (alkaline phosphatase) score. The results showed that AcP treatment reduces the explant mass and ALP score from 100% to about 60%.

Figure 29A:
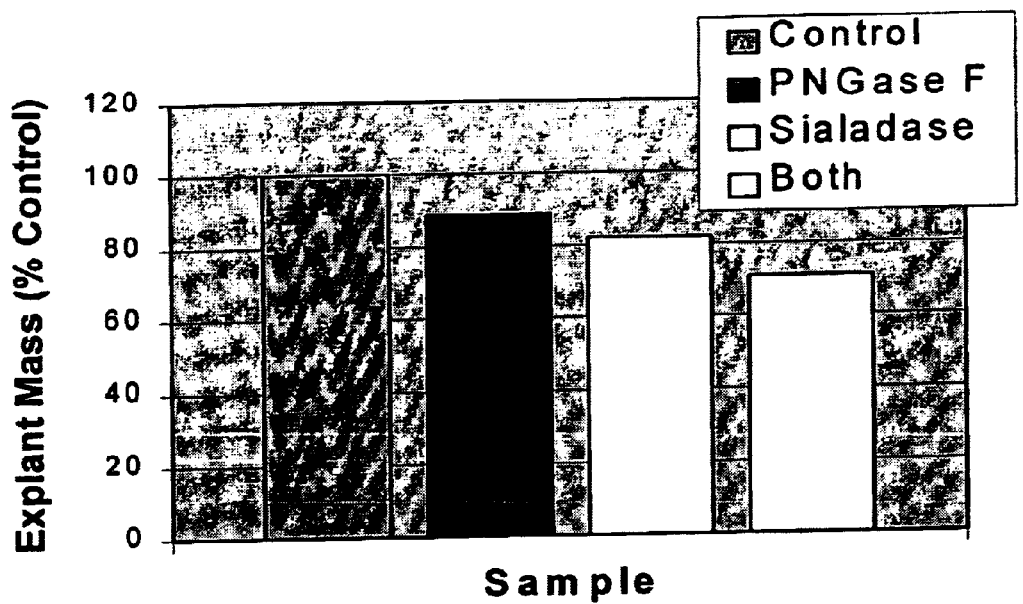
FIGS. 29A–29B are bar charts showing explant mass of glycosylated BP samples (FIG. 29A) and ALP Score (FIG. 29B) of the same samples.
Figure 29B:
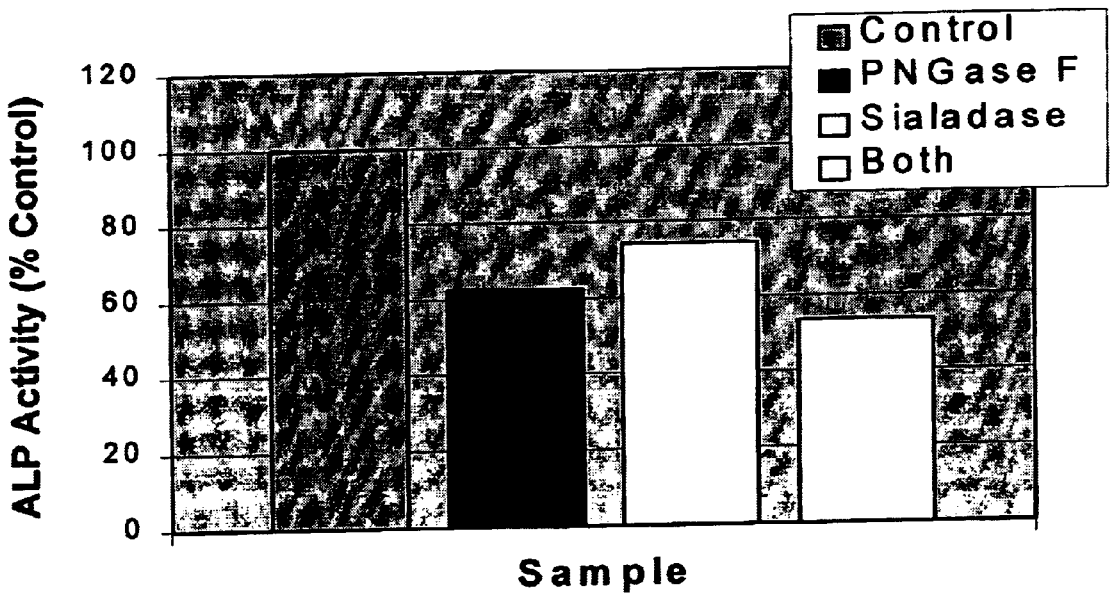

The BP was also analyzed for glycosylation. FIG. 26 shows an SDSPAGE gel stained with periodic acid schiff (PAS)—a non-specific carbohydrate stain, indicating that several of the BP components are glycosylated (starred protein identified as BMP-3). FIGS. 27 and 28 show two specific proteins (BMP-7, FIG. 27 and BMP-2, FIG. 28) treated with increasing levels of PNGase F (Peptide-N-Glycosidase F), and immunostained with the appropriate antibody. Both BMP-2 and BMP-7 show some degree of glycoslyation, but appear to have some level of protein that is resistant to PNGase F, as well (plus signs indicate increasing levels of enzyme). Functional activity of PNGase F and sialadase treated samples were assayed by explant mass and by ALP score, as shown in FIGS. 29A and 29B, indicating that glycosylation is required for full activity.

In summary, BMPs 2, 3 and 7 are modified by phosphorylation (~33%) and glycosylation (50%). These post-translation modifications do affect protein morphogenic activity.

Matrix compositions useful in treating intervertebral disc impairment in vertebrates, including humans, may be prepared according to the foregoing descriptions and examples. While various embodiments of the inventions have been described in detail, modifications and adaptations of those embodiments will be apparent to those of skill in the art in view of the present disclosure. However, such modifications and adaptations are within the spirit and scope of the present inventions, as set forth in the following claims.

What is claimed is:

1. A fluid matrix for treating intervertebral disc disease in a vertebrate, said fluid comprising cross-linked, decellularized nucleus pulposus tissue of a donor vertebrate.

2. The fluid matrix of claim 1 further comprising a growth factor.

3. The fluid matrix of claim 2 further comprising a plurality of living cells.

4. The fluid matrix of claim 3, wherein said plurality of living cells comprise chondrocytes other than the chondrocytes of the donor vertebrate.

5. The fluid matrix of claim 3, wherein said plurality of living cells comprise mesenchymal stem cells.

6. The fluid matrix of claim 3, wherein said plurality of living cells are human-derived.

7. The fluid matrix of claim 1, wherein said nucleus pulposus tissue is cross-linked with a photooxidative catalyst.

8. The fluid matrix of claim 7, wherein said catalyst is selected from the group consisting of: methylene blue, methylene green, rose bengal, riboflavin, proflavin, fluorescein, eosin, and pyridoxal-5-phosphate.

9. The fluid matrix of claim 1, wherein the donor vertebrate is a pig.

10. The fluid matrix of claim 1, wherein the donor vertebrate is a cow.

11. The fluid matrix of claim 1, wherein the donor vertebrate is a human.

* * * * *